(12) United States Patent
Bachels et al.

(10) Patent No.: US 8,173,749 B2
(45) Date of Patent: May 8, 2012

(54) PHOTOCROSSLINKABLE MATERIALS

(75) Inventors: Thomas Bachels, Grenzach-Wyhlen (DE); Zoubair Mohammed Cherkaoui, Niederdorf (CH); Guy Marck, Schlierbach (FR); Olivier Muller, Lautenbach (FR); Joachim Reichardt, Grenzach-Wyhlen (DE); Andreas Schuster, Freiburg (DE); Hubert Seiberle, Weil am Rhein (DE); Peggy Studer, Huningue (FR); Thomas Peglow, Lorrach (DE); Jean-Francois Eckert, Colmar (FR)

(73) Assignee: Rolic AG, Zug (CH)

( * ) Notice: Subject to any disclaimer, the term of this patent is extended or adjusted under 35 U.S.C. 154(b) by 783 days.

(21) Appl. No.: 12/096,719

(22) PCT Filed: Dec. 19, 2006

(86) PCT No.: PCT/CH2006/000713

§ 371 (c)(1),
(2), (4) Date: Jun. 9, 2008

(87) PCT Pub. No.: WO2007/071091

PCT Pub. Date: Jun. 28, 2007

(65) Prior Publication Data

US 2008/0293888 A1    Nov. 27, 2008

(30) Foreign Application Priority Data

Dec. 23, 2005  (EP) .................................. 05405723
May 23, 2006  (EP) .................................. 06114378

(51) Int. Cl.
*C08F 14/18*    (2006.01)

(52) U.S. Cl. ............ 525/200; 560/65; 560/44; 560/242; 560/248

(58) Field of Classification Search .................. 525/200, 525/65, 44; 526/242, 248; 560/65, 44
See application file for complete search history.

(56) References Cited

U.S. PATENT DOCUMENTS

| 6,027,772 | A | 2/2000 | Han |
| 6,066,606 | A | 5/2000 | Lu et al. |
| 6,340,506 | B1 | 1/2002 | Buchecker et al. |
| 6,831,148 | B2 | 12/2004 | Buchecker et al. |
| 2003/0039768 | A1* | 2/2003 | Buchecker et al. ............... 428/1 |
| 2010/0048849 | A1 | 2/2010 | Eckert et al. |

FOREIGN PATENT DOCUMENTS

| DE | 199 06 254 A1 | 9/1999 |
| EP | 0 860 455 A2 | 8/1998 |
| EP | 1 386 910 A1 | 2/2004 |
| WO | 99/15576 A1 | 4/1999 |
| WO | 99/49360 A1 | 9/1999 |
| WO | 99/51662 A1 | 10/1999 |
| WO | 00/59966 A1 | 10/2000 |
| WO | 01/53384 A1 | 7/2001 |
| WO | 2006/039824 A1 | 4/2006 |
| WO | 2009/080147 A1 | 7/2009 |
| WO | 2009/080271 A1 | 7/2009 |

OTHER PUBLICATIONS

USPTO search report, Feb. 22, 2011.*
Guglieiminetti et al., "Chiral Alpha Substituted Acrylates Side-Chain Polymers with a Cinnamate Core," Polymer Bulletin, Springer, Heidelberg, DE., vol. 16, No. 5, (1986), pp. 411-418.
Schadt et al., "Surface-Induced Parallel Alignment of Liquid Crystals by Linearly Polymerized Photopolymers," Jpn. Journ. Appl. Phys., vol. 31 (1992), pp. 2155-2164.
Schmitt et al., "Fast Time-Sequential Color Switch Based on Cholesteric Filters and DHF-LCDs," Proceedings of Euro-Display, (1999), 4 pgs.).
March J., REACTIONS, Advanced Organic Chemistry, pp. 363 and 365.
March J., REACTIONS, Advanced Organic Chemistry, (1977), pp. 1125-1126.

* cited by examiner

*Primary Examiner* — James J Seidleck
*Assistant Examiner* — Gregory Listvoyb
(74) *Attorney, Agent, or Firm* — Sughrue Mion, PLLC

(57) ABSTRACT

A diamine compound of formula (I) is proposed as well as polymers, copolymers, polyamic acids, polyamic acid esters, or polyimides based on such compound.

15 Claims, No Drawings

PHOTOCROSSLINKABLE MATERIALS

The invention relates to diamine compounds, represented by the general formula (I), and also relates to oligomers, polymers and copolymers from the class of polyamic acids, polyamic acid esters or polyimides (and any mixtures thereof) obtained by the reaction of a diamine compound represented by the general formula (I) and optionally of one or more additional other diamines, with one or more tetracarboxylic acid anhydrides, and to the use of these diamine compounds, oligomers, polymers and copolymers for the preparation of orientation layers for liquid crystals and in the construction of unstructured and structured optical elements and multi-layer systems.

Liquid crystal displays (LCDs) are becoming increasingly dominant in advanced visualization devices. LCDs offer favourable characteristics with respect to image quality (high luminance, high resolution, colour and grey scale capability), power consumption as well as dimensions and weight (flat panel displays). The use of commercial LCDs has become widespread, e.g. in automotive and telecommunication instruments, as well as in monitors of notebooks, desktop computers, television sets, etc. Today the need for LCDs in television applications is rapidly growing. Recently developed LCD modes possess high potentials in achieving fast response times, wide viewing angles and high luminance. Amongst other newly developed LCD modes, the MVA (multi-domain vertical alignment) mode appears to be the most promising for the use in modern television applications.

In the MVA mode the liquid crystal molecules are usually nearly vertically aligned with respect to the surface of the substrates. By using protrusions (or other alignment subdivisions) on the surface of the substrate, the liquid crystal molecules become locally pre-tilted within a single cell in more than one direction, leading to domains switchable in different directions. This multi-domain configuration exhibits very good display performance, with wide viewing angles of up to 160° in any direction, short response times (below 20 ms), high contrast ratios (up to 700:1) and high brightness. However, by means of using protrusions only, it is difficult to clearly define the domain space within a single pixel. Therefore the MVA mode demands additional manufacturing steps to ensure shape effects as well as electrical field effects on both the upper and lower substrate; hence all in all leading to complex manufacturing procedures.

In order to by-pass this technical challenge, the availability of an alignment layer would be desirable, which directly leads to pre-defined alignment directions within each pixel domain and having well controllable off-axis angles with respect to the normal axis of the substrate.

Methods for the preparation of orientation layers for liquid crystal materials are well known to the skilled person. Customarily used uniaxially rubbed polymer orientation layers, such as for example polyimides, however, do have a series of disadvantages, like the formation and deposition of dust during the rubbing process and concomitant partial destruction of the thin film transistors. Scratches due to brushing is another issue associated with this technique, which is particularly evident when the pixels are of the order of 10 microns or even lower, like e.g. in micro-display applications. Because of the strong optical magnification, which is required to visualize the displayed information, scratches easily become visible and are also the cause for the reduction of the contrast level. Furthermore, the rubbing process does not allow the production of structured layers.

The production procedure for obtaining orientation layers in which the direction of orientation is induced by irradiation with polarized light is not faced with the problems inherent to the rubbing process. With the irradiation technique it is furthermore also possible to create areas having different orientation and thus to structure the orientation layer as described for example in Jpn. J. Appl. Phys., 31 (1992), 2155-64 (Schadt et al).

Using the linearly photo-polymerizable alignment (LPP) technique, the possibility of realizing a four-domain vertical aligned nematic (VAN) LCD was demonstrated some years ago (K. Schmitt, M. Schadt; Proceedings of EuroDisplay 99, 6-9 Sep., 1999). The four-domain VAN-LCD exhibits an excellent off-state angular brightness performance.

Apart from the current display performance requirements to be fulfilled in modern TV applications, the use of appropriate LPP materials is furthermore also guided by the necessity to achieve specific optical and electro-optical properties, e.g. with respect to the compatibility with the TFT (thin film transistors). Other important characteristics of the materials must also be taken into consideration, i.e. those crucial parameters directly related to and dependent on the molecular properties of the material.

Primarily such characteristics are:

High voltage holding ratio (VHR), i.e. VHR of >90% (measured at 80° C.)

High stability of the induced pre-tilt angle against light and heat

Low alignment energy profile (short irradiation time and/or low irradiation energy)

In the case of LCDs of thin-film transistor type a certain amount of charge is applied over the course of a very short period of time to the electrodes of a pixel and must not subsequently drain away by means of the resistance of the liquid crystal. The ability to hold that charge and thus to hold the voltage drop over the liquid crystal is quantified by what is known as the "voltage holding ratio" (VHR). It is the ratio of the RMS-voltage (root mean square voltage) at a pixel within one frame period and the initial value of the voltage applied.

Photo-reactive materials for orientation layers with improved voltage holding ratios (VHR) are described in WO-A-99/49360, U.S. Pat. No. 6,066,696, U.S. Pat. No. 6,027,772, WO-A-99/15576 and WO-A-99/51662. In WO-A-99/49360, U.S. Pat. No. 6,066,696 and U.S. Pat. No. 6,027,772 blends of polymeric compounds are described, containing photo-reactive polymers and polyimides.

In WO-A-99/15576 and WO-A-99/51662 polyimides having photo-reactive cinnamate groups incorporated in their side chains are described. WO-A-99/15576 for instance discloses photo-active polymers which contain as side-chain specific photo-cross-linkable groups and of which a typical monomer unit is 6-{2-methoxy-4-[(1E)-3-methoxy-3-oxoprop-1-enyl]phenoxy}hexyl 3,5-diaminebenzoate.

In the above cited references it was generally demonstrated that in order to achieve the aforementioned important parameters, molecular structures combining firstly a polyamic/polyimide backbone (i.e. delivering molecular polarity) and secondly side chains with an incorporated photo-reactive group, such as a cinnamic acid residue, are suitable for the general concept of planar orientation [requiring only slight pretilt angles, like e.g. being used in TN (twisted nematic) devices]. However, these types of molecular structures, primarily developed for TN applications, cannot directly be utilized in MVA applications.

Thus, the present invention relates to diamine compound of formula (I):

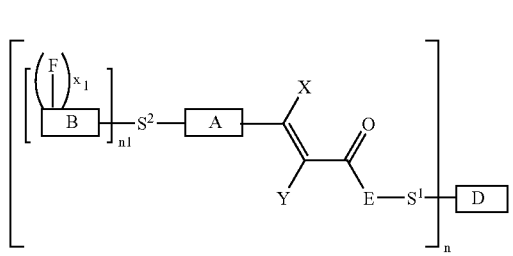

wherein,

A represents an unsubstituted or substituted carbocyclic or heterocyclic aromatic group selected from a monocyclic ring of five or six atoms, two adjacent monocyclic rings of five or six atoms, a bicyclic ring system of eight, nine or ten atoms, or a tricyclic ring system of thirteen or fourteen atoms;

and wherein the following compound residue of formula (I), the compound residue (Ia)

represents a straight-chain or branched $C_1$-$C_{16}$fluoralkyl group, wherein

F is fluorine, and $x_1$ is an integer from 1 to 15, preferably an integer from 1 to 10; more preferably 1, 2, 3, 4, 5, 6, 7, 8 or 9 and most preferred 3, 4, 5 or 7;

B represents a straight-chain or branched $C_1$-$C_{16}$alkyl group, which is in addition to its fluorine substituent(s) unsubstituted or substituted by di-($C_1$-$C_{16}$alkyl)amino, $C_1$-$C_6$alkyloxy, nitro, cyano and/or chlorine; and wherein one or more —$CH_2$— group may independently from each other be replaced by a linking group;

D represents an unsubstituted or substituted, aliphatic, aromatic and/or alicyclic diamine group having from 1 to 40 carbon atoms;

preferably D represents an unsubstituted or substituted, aliphatic, aromatic and/or alicyclic diamine group having from 1 to 40 carbon atoms, wherein the diamine group comprises an aliphatic group, which may comprise one or more heteroatom and/or bridging group;

and/or an aromatic group;

and/or an alicyclic group;

E represents an aromatic group, an oxygen atom, a sulphur atom, —NH—, —N($C_1$-$C_6$alkyl)-, —$CR^2R^3$, wherein $R^2$ and $R^3$ are independently from each other hydrogen or a cyclic, straight-chain or branched, substituted or unsubstituted $C_1$-$C_{24}$alkyl, wherein one or more —$CH_2$— group(s) may be independently from each other replaced by a linking group, and with the proviso that at least one of $R^2$ and $R^3$ is not hydrogen;

$S^1$, $S^2$ each independently from each other represents a spacer unit;

X, Y each independently from each other represents hydrogen, fluorine, chlorine, cyano, unsubstituted or with fluorine substituted $C_1$-$C_{12}$alkyl, in which one or more —$CH_2$— groups may be replaced by a linking group;

n, n1 each independently from each other represents 1, 2, 3 or 4, preferably n1 is 1 and n is 1 or 2;

with the proviso that if n is 2, 3, or 4, each A, B, $x_1$, E, $S^1$, $S^2$, X, Y are identical or different; and if n1 is 2, 3 or 4 each B, $x_1$ is identical or different;

preferably, wherein, if n>1, compound (I) has several side-chains [wherein side-chain has the meaning of structures (I) without the group D], which are linked to residue D at one atomic position within group D, e.g. two or three side chains linked to one single carbon atom within group D, or they can be linked to group D at different atomic positions within group D, e.g. at adjacent atomic positions within group D, or/and they can linked spaced further apart.

In a preferred embodiment the present invention relates to Diamine compound of formula (I):

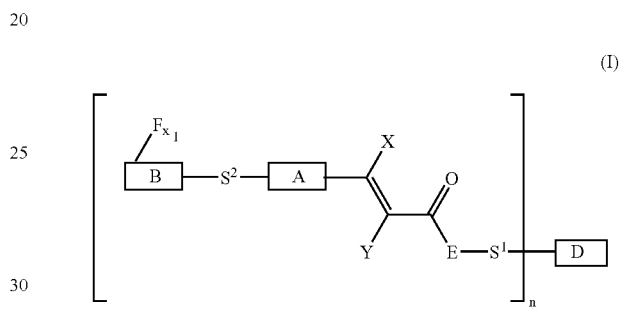

wherein,

A represents a unsubstituted or substituted carbocyclic or heterocyclic aromatic group selected from a monocyclic ring of five or six atoms, two adjacent monocyclic rings of five or six atoms, a bicyclic ring system of eight, nine or ten atoms, or a tricyclic ring system of thirteen or fourteen atoms;

F is fluorine, and $x_1$ is an integer from 1 to 15,

B represents a straight-chain or branched $C_1$-$C_{16}$alkyl, which is unsubstituted or substituted by di-($C_1$-$C_{16}$alkyl)amino, $C_1$-$C_6$alkyloxy, nitro, cyano and/or chlorine or fluorine; and wherein one or more —$CH_2$— group may independently be replaced by a linking group;

D represents unsubstituted or substituted aliphatic, aromatic or alicyclic diamine group having from 1 to 40 carbon atoms, E represents an aromatic group, an oxygen atom, a sulphur atom, —NH—, —N($C_1$-$C_6$alkyl)-, —$CR^2R^3$, wherein $R^2$ and $R^3$ are independently from each other hydrogen or a cyclic, straight-chain or branched, substituted or unsubstituted $C_1$-$C_{24}$alkyl, wherein one or more —$CH_2$— groups may be replaced by a linking group, and with the proviso that at least one of $R^2$ and $R^3$ is not hydrogen;

$S^1$, $S^2$ each independently from each other represents a spacer unit;

X, Y each independently from each other represents hydrogen, fluorine, chlorine, cyano, unsubstituted or with fluorine substituted $C_1$-$C_{12}$alkyl, in which one or more —$CH_2$— groups may be replaced by a linking group;

n is 1, 2, 3 or 4, with the proviso that if n is 2, 3, or 4, each A, B, $x_1$, D, E, $S^1$, $S^2$, X, Y may be identical or different.

The term "linking group", as used in the context of the present invention is preferably be selected from —O—, —CO, —CO—O—, —O—CO—,

—NR$^1$—, —NR$^1$—CO—, —CO—NR$^1$—, —NR$^1$—CO—O—, —O—CO—NR$^1$—, —NR$^1$—CO—NR$^1$—, —CH═CH—, —C≡C—, —O—CO—O—, and —Si(CH$_3$)$_2$—O—Si(CH$_3$)$_2$—, and wherein:
R$^1$ represents a hydrogen atom or C$_1$-C$_6$alkyl;
with the proviso that oxygen atoms of linking groups are not directly linked to each other.

The term "spacer unit" as used in the context of the present invention, is preferably a single bond, a cyclic, straight-chain or branched, substituted or unsubstituted C$_1$-C$_{24}$alkylen, wherein one or more, preferably non-adjacent, —CH$_2$— groups may independently from each other be replaced by a linking group as described above and/or a non-aromatic, aromatic, unsubstituted or substituted carbocyclic or heterocyclic group connected via bridging groups.

More preferably, the spacer unit is a cyclic, straight-chain or branched, substituted or unsubstituted C$_1$-C$_{24}$alkylen, wherein one or more, preferably non-adjacent, —CH$_2$— groups may independently from each other be replaced by a linking group and/or a non-aromatic, aromatic, unsubstituted or substituted carbocyclic or heterocyclic group connected via bridging groups.

A bridging group as used in the context of the present invention is preferably selected from —CH(OH)—, —CO—, —CH$_2$(CO)—, —SO—, —CH$_2$(SO)—, —SO$_2$—, —CH$_2$(SO$_2$)—, —COO—, —OCO—, —COCF$_2$—, —CF$_2$CO, —S—CO—, —CO—S—, —SOO—, —OSO—, —SOS—, —O—CO—O—, —CH$_2$—CH$_2$—, —OCH$_2$—, —CH$_2$O—, —CH═CH—, —C≡C—, —CH═CH—COO—, —OCO—CH═CH—, —CH═N—, —C(CH$_3$)═N—, —N═N— or a single bond; or a cyclic, straight-chain or branched, substituted or unsubstituted C$_1$-C$_{24}$alkylen, wherein one or more —CH$_2$— groups may independently from each other be replaced by a linking group as described above.

Alkyl, alkyloxy, alkylcarbonyloxy, acryloyloxyalkoxy, acryloyloxyalkyl, acryloyloxyalken, alkyloxycarbonyloxy, alkylacryloyloxy, methacryloyloxyalkoxy, methacryloyloxyalkyl, methacryloyloxyalken, alkylmethacryloyloxy, alkylmethacryloyloxy, alkylvinyl, alkylvinyloxy and alkylallyloxy and alkylene, as used in the context of the present invention denote with their alkyl residue, respectively their alkylene residue, a cyclic, straight-chain or branched, substituted or unsubstituted alkyl, respectively alkylene, in which one or more, preferably non-adjacent, —CH$_2$— group may be replaced by a linking group.

Further, the alkyl residue is for example C$_1$-C$_{40}$alkyl, especially C$_1$-C$_{30}$alkyl, preferably C$_1$-C$_{20}$alkyl, more preferably C$_1$-C$_{16}$alkyl, most preferably C$_1$-C$_{10}$alkyl and especially most preferably C$_1$-C$_6$alkyl. Accordingly alkylen is for example C$_1$-C$_{40}$alkylen, especially C$_1$-C$_{30}$alkylen, preferably C$_1$-C$_{20}$alkylen, more preferably C$_1$-C$_{16}$alkylen, most preferably C$_1$-C$_{10}$alkylen and especially most preferably C$_1$-C$_6$alkylen.

In the context of the present invention the definitions for alkyl given below, are applicable to alkylene in analogy.

C$_1$-C$_6$alkyl is for example methyl, ethyl, propyl, isopropyl, butyl, sec.-butyl, tert.-butyl, pentyl or hexyl.

C$_1$-C$_{10}$alkyl is for example methyl, ethyl, propyl, isopropyl, butyl, sec.-butyl, tert.-butyl, pentyl, hexyl, heptyl, octyl, nonyl, decyl.

C$_1$-C$_{16}$alkyl is for example methyl, ethyl, propyl, isopropyl, butyl, sec.-butyl, tert.-butyl, pentyl, hexyl, heptyl, octyl, nonyl, decyl, undecyl, dodecyl, tridecyl, tetradecyl, pentadecyl or hexadecyl.

C$_1$-C$_{20}$alkyl is for example methyl, ethyl, propyl, isopropyl, butyl, sec.-butyl, tert.-butyl, pentyl, hexyl, heptyl, octyl, nonyl, decyl, undecyl, dodecyl, tridecyl, tetradecyl, pentadecyl, hexadecyl, heptadecyl, octadecyl, nondecyl, eicosyl.

C$_1$-C$_{24}$alkyl is for example methyl, ethyl, propyl, isopropyl, butyl, sec.-butyl, tert.-butyl, pentyl, hexyl, heptyl, octyl, nonyl, decyl, undecyl, dodecyl, tridecyl, tetradecyl, pentadecyl, hexadecyl, heptadecyl, octadecyl, nondecyl, eicosyl.

C$_1$-C$_{30}$alkyl is for example methyl, ethyl, propyl, isopropyl, butyl, sec.-butyl, tert.-butyl, pentyl, hexyl, heptyl, octyl, nonyl, decyl, undecyl, dodecyl, tridecyl, tetradecyl, pentadecyl, hexadecyl, heptadecyl, octadecyl, nondecyl, eicosyl, heneicosyl, tricosyl, tetracosy, pentacosyl, hexacosdy, heptacosyl, octacosyl, nonacosy or triacontyl.

C$_1$-C$_{40}$alkyl is for example methyl, ethyl, propyl, isopropyl, butyl, sec.-butyl, tert.-butyl, pentyl, hexyl, heptyl, octyl, nonyl, decyl, undecyl, dodecyl, tridecyl, tetradecyl, pentadecyl, hexadecyl, heptadecyl, octadecyl, nondecyl, eicosyl, heneicosyl, tricosyl, tetracosy, pentacosyl, hexacosdy, heptacosyl, octacosyl, nonacosy, triacontyl or tetracontyl.

C$_1$-C$_{20}$acryloyloxyalkylene, prefererably C$_1$-C$_{10}$acryloyloxyalkylene, C$_1$-C$_6$ acryloyloxyalkylene is for example acryloyloxymethylen, acryloyloxyethylene, acryloyloxypropylene, acryloyloxyisopropylene, acryloyloxybutylene, acryloyloxy-sec.-butylene, acryloyloxypentylene, acryloyloxyhexylene, acryloyloxyheptylene, acryloyloxyoctylene, acryloyloxynonylene, acryloyloxydecylene, acryloyloxyundecylene, acryloyloxydodecane, acryloyloxytridecylene, acryloyloxytetradecylene, acryloyloxypentyldecane, acryloyloxyhexadecylene, acryloyloxyheptadecylene, acryloyloxyoctadecylene, acryloyloxynondecylene, acryloyloxyeicosylene.

C$_1$-C$_{20}$methacryloyloxyalkylene, preferably C$_1$-C$_{10}$methacryloyloxyalkylene, C$_1$-C$_6$ methacryloyloxyalkylene is for example methacryloyloxymethylen, methacryloyloxyethylene, methacryloyloxypropylene, methacryloyloxyisopropylene, methacryloyloxybutylene, methacryloyloxy-sec.-butylene, methacryloyloxypentylene, methacryloyloxyhexylene, methacryloyloxyheptylene, methacryloyloxyoctylene, methacryloyloxynonylene, methacryloyloxydecylene, methacryloyloxyundecylene, methacryloyloxydodecane, methacryloyloxytridecylene, methacryloyloxytetradecylene, methacryloyloxypentyldecane, methacryloyloxyhexadecylene, methacryloyloxyheptadecylene, methacryloyloxyoctadecylene, methacryloyloxynondecylene, methacryloyloxyeicosylene.

C$_1$-C$_{20}$acryloyloxyalkoxy, preferably C$_1$-C$_{10}$acryloyloxyalkoxy, C$_1$-C$_6$ acryloyloxyalkoxy is for example acryloyloxymethoxy, acryloyloxyethoxy, acryloyloxypropoxy, acryloyloxyisopropoxy, acryloyloxybutoxy, acryloyloxy-sec.-butoxy, acryloyloxypentoxy, acryloyloxyhexoxy, acryloyloxyheptoxy, acryloyloxyoctoxy, acryloyloxynonoxy, acryloyloxydecoxy, acryloyloxyundecoxy, acryloyloxydodecanoxy, acryloyloxytridecyloxy.

C$_1$-C$_{20}$methacryloyloxyalkoxy, preferably C$_1$-C$_{10}$methacryloyloxyalkoxy, C$_1$-C$_6$ methacryloyloxyalkoxy is for example methacryloyloxymethoxy, methacryloyloxyethoxy, methacryloyloxypropoxy, methacryloyloxyisopropoxy, methacryloyloxybutoxy, methacryloyloxy-sec.-butoxy, methacryloyloxypentoxy, methacryloyloxyhexoxy, methacryloyloxyheptoxy, methacryloyloxyoctoxy, methacryloyloxynonoxy, methacryloyloxydecoxy, methacryloyloxyundecoxy, methacryloyloxydodecanoxy, methacryloyloxytridecyloxy.

An aliphatic group is for example a saturated or unsaturated, mono-, bi-, tri-, tetra-, penta-, hexa-, hepta-, octa-, nona-, deca-valent alkyl, alkylene, alkyloxy, alkylcarbonyloxy, acryloyloxy, alkylacryl, alkylmethacryl, alkyl(en)acryl(en), alkyl(en)methacryl(en), alkyloxycarbonyloxy, alkyloxycarbonyloxy methacryloyloxy, alkylvinyl, alkylvinyloxy or alkylallyloxy, which may comprise one or more heteroatom and/or bridging group.

An alicyclic group is preferably a non-aromatic group or unit. Preferably an alicyclic group is a non-aromatic carbocyclic or heterocyclic group and represents for example ring systems, with 3 to 30 carbon atoms, as for example cyclopropane, cyclobutane, cyclopentane, cyclopentene, cyclohexane, cyclohexene, cyclohexadiene, decaline, tetrahydrofuran, dioxane, pyrrolidine, piperidine or a steroidal skeleton such as cholesterol.

The term "aromatic", as used in the context of the present invention, preferably denotes unsubstituted or substituted carbocyclic and heterocyclic groups, incorporating five, six, ten to 14 ring atoms, e.g. furan, benzene or phenylene, pyridine, pyrimidine, naphthalenen, which may form ring assemblies, such as biphenylene or triphenylen, which are uninterrupted or interrupted by at least a single heteroatom and/or at least a single bridging group; or fused polycyclic systems, such as phenanthrene, tetraline. Preferably aromatic group are benzene, phenylene, biphenylene or triphenylen. More preferred aromatic group are benzene, phenylene and biphenylene.

A carbocyclic or heterocyclic aromatic group incorporates preferably five, six, ten or 14 ring atoms, as for example furan, benzene, pyridine, triazine, pyrimidine, naphthalene, phenanthrene, biphenylene or tetraline units, preferably naphthalene, phenanthrene, biphenylene or phenylene, more preferably naphthalene, biphenylene or phenylene, and most preferably phenylene.

The carbocyclic or heterocyclic aromatic group is for example unsubstituted or mono- or poly-substituted. Preferred substitutents of carbocyclic or heterocyclic aromatic groups are at least one halogen, hydroxyl, a polar group, acryloyloxy, alkylacryloyloxy, alkoxy, alkylcarbonyloxy, alkyloxycarbonyloxy, alkyloxocarbonyloxy, methacryloyloxy, vinyl, vinyloxy and/or allyloxy group, wherein the alkyl residue has preferably from 1 to 20 carbon atoms, and more preferably having from 1 to 10 carbon atoms. Preferred polar groups are nitro, cyano or a carboxy group, and/or a cyclic, straight-chain or branched $C_1$-$C_{30}$alkyl, which is unsubstituted, mono- or poly-substituted. Preferred substitutents of $C_1$-$C_{30}$alkyl are methyl, fluorine and/or chlorine, wherein one or more, preferably non-adjacent, —$CH_2$— group may independently of each other be replaced by a linking group. Preferably, the linking group is selected from —O—, —CO—, —COO— and/or —OCO—.

A monocyclic ring of five or six atoms is for example furan, benzene, preferably phenylene, pyridine, pyrimidine.

A bicyclic ring system of eight, nine or ten atoms is for example naphthalene, biphenylene or tetraline.

A tricyclic ring system of thirteen or fourteen atoms is for example phenanthrene.

The term "phenylene", as used in the context of the present invention, preferably denotes a 1,2-, 1,3- or 1,4-phenylene group, which is optionally substituted. It is preferred that the phenylene group is either a 1,3- or a 1,4-phenylene group. 1,4-phenylene groups are especially preferred.

The term "halogen" denotes a chloro, fluoro, bromo or iodo substituent, preferably a chloro or fluoro substituent.

The term "polar group", as used in the context of the present invention primarily denotes a group like a nitro, cyano, or a carboxy group.

The term "heteroatom", as used in the context of the present invention primarily denotes oxygen, sulphur and nitrogen, preferably oxygen and nitrogen, in the latter case preferably in the form of —NH—.

The term "optionally substituted" as used in the context of the present invention primarily means substituted by lower alkyl, such as $C_1$-$C_6$alkyl, lower alkoxy, such as $C_1$-$C_6$alkoxy, hydroxy, halogen or by a polar group as defined above.

The term "diamine" or "diamine compound" is to be understood as designating a chemical structure which has at least two amino groups, i.e. which may also have 3 or more amino groups. The at least two amino groups are preferably able to react with e.g. anhydrides as outlined in more detail below.

The term "dinitro" or "dinitro compound" is to be understood as designating a chemical structure which has at least two nitro groups, i.e. which may also have 3 or more nitro groups, and wherein the dinitro group is a precursor compound of the "diamino compound". The dinitro compound is conventionally converted to the diamino compound by reduction methods known in the art.

With respect to straight chain or branched alkyl, alkylene, alkoxy, alkylcarbonyloxy, acryloyloxyalkoxy, acryloyloxyalkyl, acryloyloxyalkene, alkyloxycarbonyloxy, alkylacryloyloxy, methacryloyloxyalkoxy, methacryloyloxyalkyl, methacryloyloxyalkene, alkylmethacryloyloxy, alkylmethacryloyloxy, alkylvinyl, alkylvinyloxy, alkylallyloxy and alkylene groups it is repeatedly pointed out that some or several of the —$CH_2$— groups may be replaced e.g. by heteroatoms, but also by other groups, preferably bridging groups. In such cases it is generally preferred that such replacement groups are not directly linked to each other. It is alternatively preferred that heteroatoms, and in particular oxygen atoms are not directly linked to each other.

Preferably, A is unsubstituted or substituted phenanthrylene, naphthylene, biphenylene or phenylene, wherein the preferred substituent(s) is (are) a halogen atom, a hydroxy group and/or by a polar group, wherein the polar group is preferably nitro, cyano, carboxy; and/or by acryloyloxy, alkylacryl, alkylmethacryl, alkyl(en)acryl, alkyl(en)methacryl, acrylenacryl, methacrylenalkyl, methacryloyloxy, vinyl, vinyloxy, allyl, allyloxy, and/or by a cyclic, straight-chain or branched alkyl, which is unsubstituted, mono- or poly-substituted by fluorine and/or chlorine, having from 1 to 20 carbon atoms, wherein one or more, preferably non-adjacent, —$CH_2$— groups may independently be replaced by a linking group and or an aromatic or an alicyclic group, preferably the linking group is selected from —O—, —CO—, —CO—O—, —O—CO—.

More preferably A is substituted or unsubstituted naphthylene, biphenylene or phenylene, wherein the preferred substituent(s) is (are) halogen atom, hydroxy group and/or by acryloyloxy, alkylacryl, alkylmethacryl, acrylenacryl, methacrylenalkyl, methacryloyloxy, straight-chain or branched alkyl, alkoxy, alkylcarbonyloxy, and/or alkyloxycarbonyl groups, wherein the alkyl residue has from 1 to 20 carbon atoms.

Most preferably A is substituted or unsubstituted phenylene, preferably 1,4-phenylen, wherein the preferred substituent(s) is (are) a halogen atom, and/or by acryloyloxy or methacryloyloxy, and/or by an alkoxy, alkylacryl, alkylmethacryl, acrylenacryl, methacrylenalkyl, alkylcarbonyloxy, and/or alkyloxycarbonyl groups, wherein the alkyl residue has from 1 to 10 carbon atoms.

A preferred embodiment of the present invention concerns a diamine compound of formula (I) as described above, wherein the following compound residue (Ia)

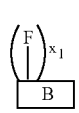
(Ia)

represents a straight-chain or branched $C_1$-$C_{16}$fluoralkyl group with terminal units selected from —$CF_2H$ and —$CF_3$, preferably selected from —$CF_2H$ or —$CF_3$, —$CF_2CF_3$, —$CF_2CHF_2$, —$(CF_2)_2CF_3$, —$(CF_2)_2CHF_2$, —$(CF_2)_3CHF_2$, —$(CF_2)_3CF_3$, —$CF(CF_3)_2$ and —$CF_2(CHF)CF_3$.

Preferably B is a straight-chain or branched $C_1$-$C_{12}$alkyl, wherein one or more, preferably non-adjacent, —$CH_2$— group(s) may independently from each other be replaced by a group selected from —O—, —CO, —CO—O—, —O—CO—, —$NR^1$—, —$NR^1$—CO—, —CO—$NR^1$—, —$NR^1$—CO—O—, —O—CO—$NR^1$—, —$NR^1$—CO—$NR^1$—, —CH=CH—, —C≡C—, —O—CO—O—, and —$Si(CH_3)_2$—O—$Si(CH_3)_2$—, an aromatic and an alicyclic group; and wherein:
$R^1$ represents a hydrogen atom or $C_1$-$C_6$alkyl;
with the proviso that oxygen atoms are not directly linked to each other.

More preferably, B is a straight-chain or branched $C_1$-$C_{12}$alkyl, wherein one or more, preferably non-adjacent, —$CH_2$— group(s) may be replaced by a group selected from from —O—, —CO, —CO—O—, —O—CO—, —$NR^1$—, —$NR^1$—CO—, —CO—$NR^1$— or —CH=CH— wherein:
$R^1$ represents a hydrogen atom or $C_1$-$C_6$alkyl;
with the proviso that oxygen atoms are not directly linked to each other.

Most preferably, B is a straight-chain or branched $C_1$-$C_8$alkyl, wherein one or more, preferably non-adjacent, —$CH_2$— group(s) may be replaced by a group selected from from —O—, —CO, —CO—O—, —O—CO—, —$NR^1$—, —$NR^1$—CO—, —CO—$NR^1$— or —CH=CH— wherein:
$R^1$ represents a hydrogen atom or $C_1$-$C_6$alkyl;
with the proviso that oxygen atoms are not directly linked to each other.

Especially most preferably, B is a straight-chain or branched $C_1$-$C_8$alkyl, wherein one or more, preferably non-adjacent, the —$CH_2$— group may be replaced by a group selected from —O—, —CO—, —CO—O—, —O—CO—, and —CH=CH—, with the proviso that oxygen atoms are not directly linked to each other.

Preferably the compound residue (Ia) is:
trifluoromethyl; 2,2,2-trifluoroethyl; difluoromethyl; pentafluoroethyl; 2,2-tetrafluoroethyl; 3,2-tetrafluoroethyl; 3,3,3-trifluoropropyl; 2,2,3,3-tetrafluoropropyl; 2,2,3,3,3-pentafluoropropyl; hexafluoropropyl; heptafluoropropyl; 4,4,4-trifluorobutyl; tetrafluorobutyl; 3,3,4,4,4-pentafluorobutyl; hexafluorobutyl; 2,2,3,3,4,4,4-heptafluorobutyl; 5,5,5-trifluoropentyl; tetrafluoropentyl; 4,4,5,5,5-pentafluoropentyl; hexafluoropentyl; 3,3,4,4,5,5,5-heptafluoropentyl; 6,6,6-trifluorohexyl; tetrafluorohexyl; 5,5,6,6,6-pentafluorohexyl; hexafluorohexyl; 4,4,5,5,6,6,6-heptafluorohexyl; nonafluorohexyl;
1-trifluoro-1,2,2,2-tertafluoroethoxy, 2-trifluoro-2,3,3,3-tertafluoropropoxy, 3-trifluoro-3,4,4,4-tertafluorobutoxy, 4-trifluoro-4,5,5,5-tertafluoropentoxy, 5-trifluoro-5,6,6,6-tertafluorohexoxy, 6-trifluoro-6,7,7,7-tertafluoroheptoxy, 7-trifluoro-7,8,8,8-tertafluorononoxy;
fluoroalkoxy derivatives, such as
trifluoromethoxy; 2,2,2-trifluoroethoxy; difluoromethoxy; pentafluoroethoxy; 1,1,2,2-tetrafluoroethoxy; 2,2,2,1-tetrafluoroethoxy; 3,3,3-trifluoropropoxy; 2,2,3,3-tetrafluoropropoxy; 2,2,3,3,3-pentafluoropropoxy; hexafluoropropoxyl; heptafluoropropoxy; 4,4,4-trifluorobutoxy; tetrafluorobutoxy; 3,3,4,4,4-pentafluorobutoxy; 2,2,3,3,4,4-hexafluorobutoxy; 2,2,3,3,4,4,4-heptafluorobutoxy; 5,5,5-trifluoropentoxy; tetrafluoropentoxy; 4,4,5,5,5-pentafluoropentoxy; hexafluoropentoxy; 3,3,4,4,5,5,5-heptafluoropentoxy; 6,6,6-trifluorohexoxy; tetrafluorohexoxy; 5,5,6,6,6-pentafluorohexoxy; hexafluorohexoxy; 4,4,5,5,6,6,6-heptafluorohexoxy; nonafluorohexoxy;
trifluoromethylen carbamate; 2,2,2-trifluoroethylen carbamate; difluoromethylen carbamate; pentafluoroethylen carbamate; 2,2-tetrafluorethylen carbamate; 3,2-tetrafluoroethylen carbamate; 3,3,3-trifluoropropylen carbamate; 2,2,3,3-tetrafluoropropylen carbamate; 2,2,3,3,3-pentafluoropropylen carbamate; hexafluoropropylen carbamate; heptafluoropropylen carbamate; 4,4,4-trifluorobutylen carbamate; tetrafluorobutylen carbamate; 3,3,4,4,4-pentafluorobutylen carbamate; hexafluorobutylen carbamate; 2,2,3,3,4,4,4-heptafluorobutylen carbamate; 5,5,5-trifluoropentylen carbamate; tetrafluoropentylen carbamate; 4,4,5,5,5-pentafluoropentylen carbamate; hexafluoropentylen carbamate; 3,3,4,4,5,5,5-heptafluoropentylen carbamate; 6,6,6-trifluorohexylen carbamate; tetrafluorohexylen carbamate; 5,5,6,6,6-pentafluorohexylen carbamate; hexafluorohexylen carbamate; 4,4,5,5,6,6,6-heptafluorohexylen carbamate; nonafluorohexylen carbamate;
fluoroalkyloyloxy derivatives, such as
trifluoromethyloyloxy; 2,2,2-trifluoroethyloyloxy; pentafluoroethyloyloxy; 1,1,2,2-tetrafluorethyloyloxy; 2,2,2,1-tetrafluorethyloyloxy; 3,3,3-trifluoropropyloyloxy; tetrafluoropropyloyloxy; 2,2,3,3,3-pentafluoropropyloyloxy; hexafluoropropyloyloxy; 1,1,2,2,3,3,3-heptafluoropropyloyloxy; 4,4,4-trifluorobutyloyloxy; tetrafluorobutyloyloxy; 3,3,4,4,4-pentafluorobutyloyloxy; hexafluorobutyloyloxy; 2,2,3,3,4,4,4-heptafluorobutyloyloxy; 5,5,5-trifluoropentyloyloxy; tetrafluoropentyloyloxy; 4,4,5,5,5-pentafluoropentyloyloxy; hexafluoropentyloyloxy; 3,3,4,4,5,5-heptafluoropentyloyloxy; 6,6,6-trifluorohexyloyloxy; tetrafluorohexyloyloxy; 5,5,6,6,6-pentafluorohexyloyloxy; hexafluorohexyloyloxy; 4,4,5,5,6,6,6-heptafluorohexyloyloxy;
trifluoroacetyl; nonafluorohexyloyloxy;
4,4,4-trifluorobut-2-enyl; 5,5,5-trifluoropent-1-enyl; 6,6,6-trifluorohex-1-enyl; 7,7,7-trifluorohept-1-enyl; trifluoroacetylaminomethoxy; trifluoroacetylaminoethoxy; trifluoroacetylaminopropoxy; trifluoroacetylaminobutoxy; 2-fluoroethyl; 3-fluoropropyl; 4-fluorobutyl; 5-fluoropentyl; 6-fluorohexyl; 2-fluoroethoxy; 3-fluoropropoxy; 4-fluorobutoxy; 5-fluoropentoxy; 6-fluorohexyloxy; 4-fluorobut-1-enyl; 5-fluoropent-1-enyl; 6-fluorohex-1-enyl; 7-fluorohept-1-enyl; 4,4,4-trifluoro-3-(trifluoromethyl)butoxy; 4,5,5-trifluoropent-4-enoxy; 4,5,5-trifluoropent-4-enoyloxy; 5,6,6-trifluorohex-5-enoxy or 5,6,6-trifluoropent-5-enoyloxy.

Especially preferred are fluoroalkoxy, preferably trifluor- and pentafluoro fluoroalkoxy derivatives, especially preferred are 5,5,5-trifluoropentoxy and 4,4,5,5,5-pentafluoropentoxy.

D is preferably selected from formula (III):

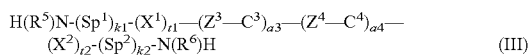

(III)

wherein:
R$^5$, R$^6$ each independently from each other represents a hydrogen atom or C$_1$-C$_6$alkyl;
Sp$^1$, Sp$^2$ each independently from each other represent an unsubstituted or substituted straight-chain or branched C$_1$-C$_{20}$alkylene, in which one or more —CH$_2$-group may independently from each other be replaced by a linking group, and
k$^1$, k$^2$ each independently is an integer having a value of 0 or 1; and
X$^1$, X$^2$ each independently represents a linking spacer, preferably selected from —O—, —S—, —NH—, N(CH$_3$)—, —CH(OH)—, —CO—, —CH$_2$(CO)—, —SO—, —CH$_2$(SO)—, —SO$_2$—, —CH$_2$(SO$_2$)—, —COO—, —OCO—, —OCO—O—, —S—CO—, —CO—S—, —SOO—, —OSO—, —SOS—, —CH$_2$—CH$_2$—, —OCH$_2$—, —CH$_2$O—, —CH=CH—, or —C≡C— or a single bond; and
t$^1$, t$^2$ each independently is an integer having a value of 0 or 1; and
C$^3$, C$^4$ each independently represents a non-aromatic, aromatic, substituted or unsubstituted carbocyclic or heterocyclic group, which may have a side chain T, and
Z$^3$ represents a bridging group; and
Z$^4$ represents a substituted or unsubstituted straight-chain or branched C$_1$-C$_{20}$alkylene group, in which one or more —CH$_2$— group may independently from each other be replaced by a non-aromatic, aromatic, unsubstituted or substituted carbocyclic or heterocyclic group; and/or a heteroatom and/or by a bridging group as described above; preferably, Z$^4$ has one of the meanings of Z$^3$ or represents an unsubstituted or substituted straight-chain or branched C$_1$-C$_{14}$alkylene group, in which one or more, preferably non-adjacent, —CH$_2$— group may be replaced by an oxygen atom and/or one or more carbon-carbon single bond is replaced by a carbon-carbon double or a carbon-carbon triple bond; and
a$_3$, a$_4$ are independently integers from 0 to 3, such that a$_3$+a$_4$≦4; and wherein
D is at least once linked to at least one group S$^1$ in formula (I) via group Sp$^1$ and/or Sp$^2$; and/or linked via at least one non-aromatic, aromatic, substituted or unsubstituted carbocyclic or heterocyclic group of C$^3$ and/or of group C$^4$, and/or linked via at least one side chain T of group C$^4$ and/or of group C$^3$; and/or linked via group Z$^4$; and at least one of k$^1$, k$^2$, a$^3$ and a$^4$ is not equal to zero; and wherein linking group and bridging group are as described above,
and preferably compound of formula (I), wherein preferably, if n>1, then the side chains [i.e. structures (I) without the group D] can either be linked to the group D at one atomic position within group D, e.g. two or three side chains connected to one single carbon atom within group D, or they can be linked to group D at different atomic positions within group D, e.g. at adjacent atomic positions within group D, but also spaced further apart.

The term "side chain", T, represents a substituted or unsubstituted straight-chain or branched C$_1$-C$_{20}$alkylene group(s), in which one or more —CH$_2$— group may independently from each other be replaced by a non-aromatic, aromatic, unsubstituted or substituted carbocyclic or heterocyclic group, or a heteroatom and/or by a bridging group, which is at least once linked to at least one group S$^1$ in formula (I).

Preferably D is selected from formula (III), wherein:
C$^3$, C$^4$ independently from each other are selected from a compound of group G$^2$, wherein group G$^2$ denotes:

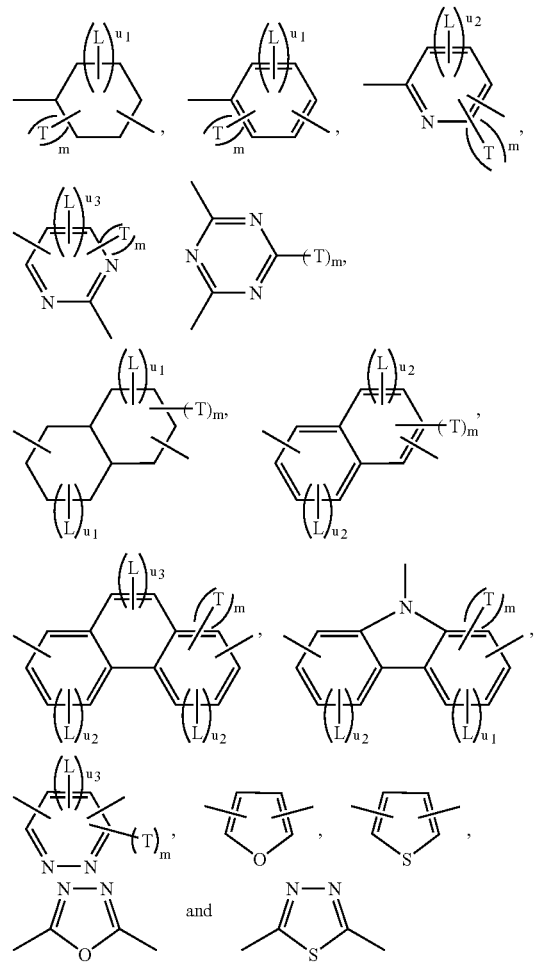

and wherein
"—" denotes the connecting bonds of C$^3$ and C$^4$ to the adjacent groups of compound of formula (III) as described above; and
L is —CH$_3$, —COCH$_3$, —OCH$_3$, nitro, cyano, halogen, CH$_2$=CH—, CH$_2$=C(CH$_3$)—, CH$_2$=CH—(CO)O—, CH$_2$=CH—O—, —NR$^5$R$^6$, CH$_2$=C(CH$_3$)—(CO)O—, CH$_2$=C(CH$_3$)—O—,
wherein:
R$^5$, R$^6$ each independently from each other represents a hydrogen atom or C$_1$-C$_6$alkyl;
T represents a substituted or unsubstituted straight-chain or branched C$_1$-C$_{20}$alkylene group, in which one or more —CH$_2$— group may independently from each other be replaced by a non-aromatic, aromatic, unsubstituted or substituted carbocyclic or heterocyclic group, or a heteroatom and/or by a bridging group;
m is an integer from 0 to 2; preferably 1 or 0; and more preferably 0;
u$_1$ is an integer from 0 to 4, with the proviso that m+u$_1$ is ≦4; and
u$_2$ is an integer from 0 to 3; with the proviso that m+u$_2$ is ≦3; and
u$_3$ is an integer from 0 to 2; with the proviso that m+u$_3$ is ≦2.

D is more preferably selected from the following group of structures: substituted or unsubstituted o-phenylenediamine, p-phenylenediamine, m-phenylenediamine, biphenyldiamine, aminophenylen-$Z^4$-phenylenamino, wherein $Z^4$ has the same meaning and preferences as given above; naphthylenediamine, benzidine, diaminofluorene, 3,4-diaminobenzoic acid, 3,4-diaminobenzyl alcohol dihydrochloride, 2,4-diaminobenzoic acid, L-(+)-threo-2-amino-1-(4-aminophenyl)-1,3-propanediol, p-aminobenzoic acid, [3,5-3h]-4-amino-2-methoxybenzoic acid, L-(+)-threo-2-(N,N-dimethylamino)-1-(4-aminophenyl)-1,3-propanediol, 2,7-diaminofluorene, 4,4'-diaminooctafluorobiphenyl, 3,3'-diaminobenzidine, 2,7-diamino-9-fluorenone, 3,5,3',5'-tetrabromo-biphenyl-4,4'-diamine, 2,2'-dichloro[1,1'-biphenyl]-4,4'-diamine, 3,9-diamino-1,11-dimethyl-5,7-dihydro-dibenzo(a,c)cyclohepten-6-one, dibenzo(1,2)dithiine-3,8-diamine, 3,3'-diaminobenzophenone, 3,3'-diaminodiphenylmethane, 4,4-bis-(3-amino-4-hydroxyphenyl)-valeric acid, 2,2-bis(3-amino-4-hydroxyphenyl)hexafluoropropane, 2,2-bis(3-amino-4-methylphenyl)hexafluoropropane, tetrabromo methylenedianiline, 2,7-diamino-9-fluorenone, 2,2-bis(3-aminophenyl)hexafluoropropane, bis-(3-amino-4-chlorophenyl)-methanone, bis-(3-amino-4-dimethylamino-phenyl)-methanone, 3-[3-amino-5-(trifluoromethyl)benzyl]-5-(trifluoromethyl)aniline, 1,5-diaminonaphthalene, benzidine-3,3'-dicarboxylic acid, 4,4'-diamino-1,1'-binaphthyl, 4,4'-diaminodiphenyl-3,3'-diglycolic acid, dihydroethidium, o-dianisidine, 2,2'-dichloro-5,5'-dimethoxybenzidine, 3-methoxybenzidine, 3,3'-dichlorobenzidine (diphenyl-d6), 2,2'-bis(trifluoromethyl)benzidine, 3,3'-bis(trifluoromethyl)benzidine, 3,3'-dichlorobenzidine-d6, tetramethylbenzidine, di-(aminophenyl)alkylen and from amino compounds listed below, which do not carry two amino groups and are taken as derivatives with at least one additional amino group: aniline, 4-amino-2,3,5,6-tetrafluorobenzoic acid, 4-amino-3,5-diiodobenzoic acid, 4-amino-3-methylbenzoic acid, 4-amino-2-chlorobenzoic acid, 4-aminosalicylic acid, 4-aminobenzoic acid, 4-aminophthalic acid, 1-(4-aminophenyl)ethanol, 4-aminobenzyl alcohol, 4-amino-3-methoxybenzoic acid, 4-aminophenyl ethyl carbinol, 4-amino-3-nitrobenzoic acid, 4-amino-3,5-dinitrobenzoic acid, 4-amino-3,5-dichlorobenzoic acid, 4-amino-3-hydroxybenzoic acid, 4-aminobenzyl alcohol hydrochloride, 4-aminobenzoic acid hydrochloride, pararosaniline base, 4-amino-5-chloro-2-methoxybenzoic acid, 4-(hexafluoro-2-hydroxyisopropyl)aniline, piperazine-p-amino benzoate, 4-amino-3,5-dibromobenzoic acid, isonicotinic acid hydrazide p-amino-salicylate salt, 4-amino-3,5-diiodosalicylic acid, 4-amino-2-methoxybenzoic acid, 2-[2-(4-aminophenyl)-2-hydroxy-1-(hydroxymethyl)ethyl]isoindoline-1,3-dione, 4-amino-2-nitrobenzoic acid, ethyl 2-(4-aminophenyl)-3,3,3-trifluoro-2-hydroxypropanoate, ethyl 2-(4-amino-3-methylphenyl)-3,3,3-trifluoro-2-hydroxypropanoate, ethyl 2-(4-amino-3-methoxyphenyl)-3,3,3-trifluoro-2-hydroxypropanoate, 4-aminonaphthalene-1,8-dicarboxylic acid, 4-amino-3-chloro-5-methylbenzoic acid, 4-amino-2,6-dimethylbenzoic acid, 4-amino-3-fluorobenzoic acid, 4-amino-5-bromo-2-methoxybenzenecarboxylic acid, 3,3'-tolidine-5-sulfonic acid, or their derivatives, again with the proviso that compounds listed which do not carry two amino groups are taken as derivatives with at least one additional amino group.

The diamine groups D are commercial available or accessible by known methods. The second amino group is accessible for example by substitution reaction.

D is further more preferably selected from the group of the following compounds:

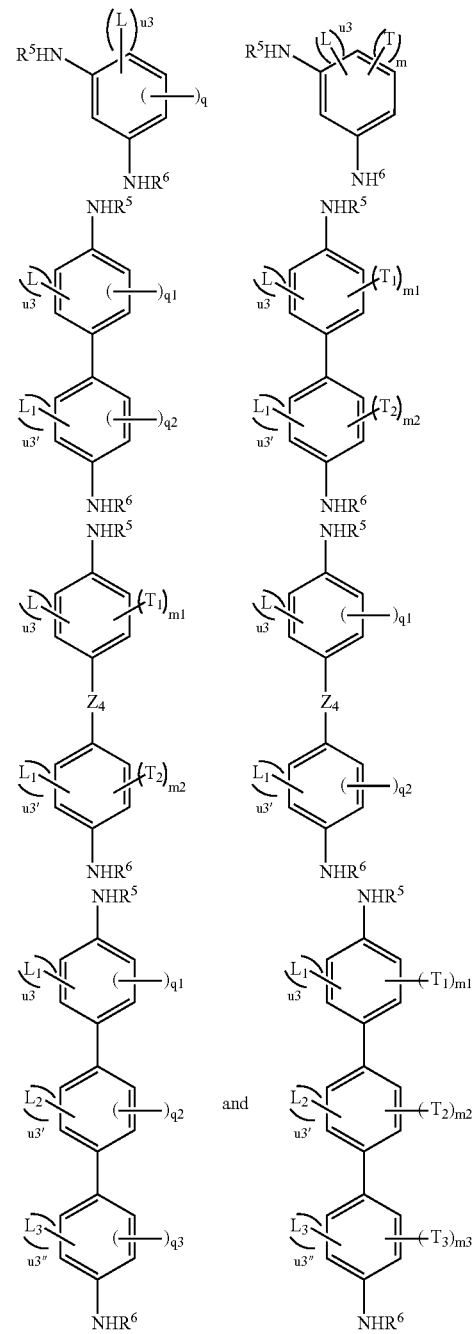

wherein
L, $L_1$, $L_2$ and $L_3$ are indepentyl from each other —$CH_3$, —$COCH_3$, —$OCH_3$, nitro, cyano, halogen, $CH_2$=CH—, $CH_2$=C($CH_3$)—, $CH_2$=CH—(CO)O—, $CH_2$=CH—O—, —$NR^5R^6$, $CH_2$=C($CH_3$)—(CO)O— or $CH_2$=C($CH_3$)—O—, T, $T_1$, $T_2$ and $T_3$ are independently from each other a substituted or unsubstituted straight-chain or branched $C_1$-$C_{20}$alkylene group, in which one or more —$CH_2$— group(s) may independently from each other be replaced by a non-aromatic, aromatic, unsubstituted or substituted carbocyclic or heterocyclic group, and/or a heteroatom and/or by a bridging group;

"—" is a single bond, q is an integer of 1 or 2; and q1, q2 and q3 are indepentyl from each other an integer from 0 to 2; preferably 1 or 2;

m is an integer of 1 or 2;

m1, m2 and m3 are indepentyl from each other an integer from 0 to 2; preferably 1 or 2;

$u_3$, $u_3'$ and $u_3''$ are indepentyl from each other an integer from 0 to 2;

$R^5$, $R^6$ and $Z^4$ are as described above; and wherein

D is at least once linked to at least one group $S^1$ in formula (I) via a single bond "—"; or via a side chain T, $T_1$, $T_2$ or $T_3$; or via group $Z^4$;

with the proviso that u3+q, or u3+m is ≦4;

u3+q1 and/or u3'+q2 or/and u3+m1, or/and u3'+m2, or/and u3"+q3, or/and u3"+m3 is ≦4;

q1+q2, and m1+m2; and q1+q2+q3, and m1+m2+m3 is ≧1.

Most preferred are diamine compounds according to the invention, wherein D is a selected from the group of the following compounds:

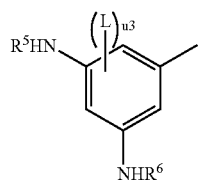
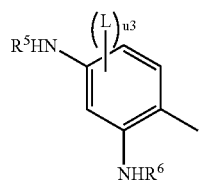

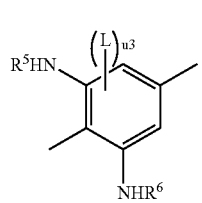
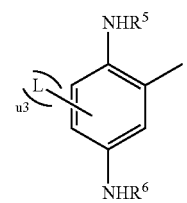

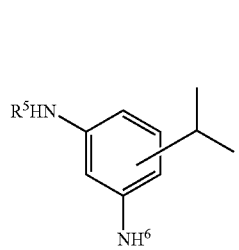
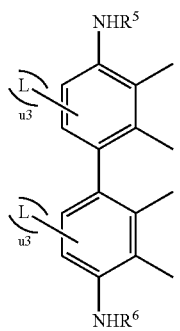

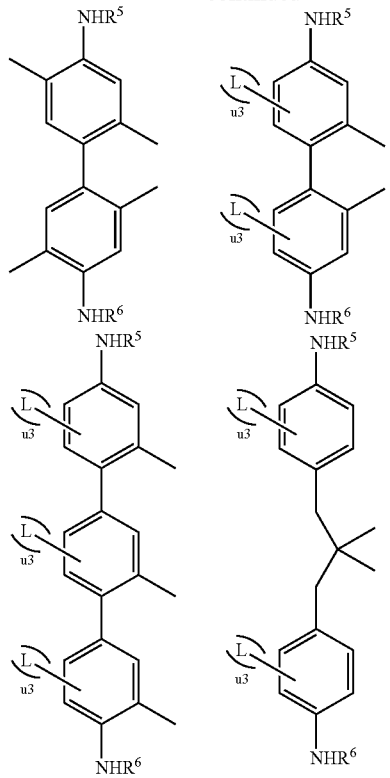

and

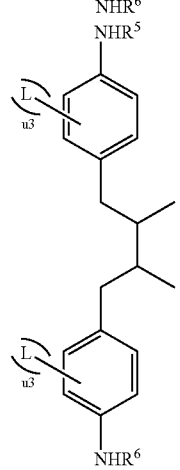

"—" denotes the linking(s) of D to $S^1$ in compound (I) and represents a single bond; and L is —$CH_3$, —$COCH_3$, —$OCH_3$, nitro, cyano, halogen, $CH_2$=CH—, $CH_2$=C($CH_3$)—, $CH_2$=CH—(CO)O—, $CH_2$=CH—O—, —$NR^5R^6$, $CH_2$=C($CH_3$)—(CO)O— or $CH_2$=C($CH_3$)—O—, wherein:

$R^5$, $R^6$ each independently from each other represents a hydrogen atom or $C_1$-$C_6$alkyl;

$u_3$ is an integer from 0 to 2.

E preferably represents an phenylene, an oxygen atom or a —N(H)— group, more preferred E is oxygen or a —N(H)— group, and most preferred E is oxygen.

Preferably, $S^1$, $S^2$ each independently from each other represents a single bond or a spacer unit, which is a cyclic, straight-chain or branched, substituted or unsubstituted $C_1$-$C_{24}$alkylen, in which one or more, preferably non-adjacent, —$CH_2$— group may be replaced by a linking group, and/or a non-aromatic, aromatic, unsubstituted or substituted carbocyclic or heterocyclic group of formula (IV):

$$—(Z^1—C^1)_{a1}—(Z^2—C^2)_{a2}—(Z^{1a})_{a3}— \quad (IV)$$

wherein:
$C^1$, $C^2$ each independently represents a non-aromatic, aromatic, optionally substituted carbocyclic or heterocyclic group, preferably connected to each other via the bridging groups $Z^1$ and $Z^2$ and/or $Z^{1a}$, preferably $C^1$ and $C^2$ are connected at the opposite positions via the bridging groups $Z^1$ and $Z^2$ and/or $Z^{1a}$, so that groups $S^1$ and/or $S^2$ have a long molecular axis, and $Z^1$, $Z^2$, $Z^{1a}$ each independently represents a bridging group, preferably selected from —CH(OH)—, —CH$_2$—, —O—, —CO—, —CH$_2$(CO)—, —SO—, —CH$_2$(SO)—, —SO$_2$—, —CH$_2$(SO$_2$)—, —COO—, —OCO—, —COCF$_2$—, —CF$_2$CO—, —S—CO—, —CO—S—, —SOO—, —OSO—, —SOS—, —CH$_2$—CH$_2$—, —OCH$_2$—, —CH$_2$O—, —CH═CH—, —C≡C—, —CH═CH—COO—, —OCO—CH═CH—, —CH═N—, —C(CH$_3$)═N—, —O—CO—O—, —N═N— or a single bond; and $a_1$, $a_2$, $a_3$ each independently represents an integer from 0 to 3, such that $a_1+a_2+a_3 \leq 6$, wherein preferably $S^2$ is linked to A via $Z^1$; preferably $a_3$ is 0 and $a_1+a_2 \leq 4$.

More preferred $S^1$ represents a straight-chain or branched $C_1$-$C_{24}$alkylen, wherein one or more —CH$_2$— group may independently be replaced by a linking group or/and a group represented by the formula (IV), wherein:

$C^1$, $C^2$ are selected from a compound of group $G^1$, wherein group $G^1$ is:

[chemical structures with labels (L)u$_1$, (L)u$_1$, (L)u$_2$, (L)u$_3$, (L)u$_1$, (L)u$_2$, (L)u$_3$, (L)u$_2$, (L)u$_2$, (L)u$_2$, (L)u$_1$, (L)u$_3$, and]

wherein:
"—" denotes the connecting bonds of $C^1$ and $C^2$ to the adjacent groups in formula (IV); and L is —CH$_3$, —OCH$_3$, —COCH$_3$, nitro, cyano, halogen, CH$_2$═CH—, CH$_2$═C(CH$_3$)—, CH$_2$═CH—(CO)O—, CH$_2$═CH—O—, CH$_2$═C(CH$_3$)—(CO)O—, or CH$_2$═C(CH$_3$)—O—, $u_1$ is an integer from 0 to 4; and
$u_2$ is an integer from 0 to 3; and
$u_3$ is an integer from 0 to 2; and $Z^1$, $Z^2$, $Z^{1a}$ each independently represents —O—, —CO—, —COO—, —OCO—, —COCF$_2$—, —CF$_2$CO—, —CH$_2$—CH$_2$—, —OCH$_2$—, —CH$_2$O—, —CH═CH—, —C≡C—, —CH═CH—COO—, —OCO—CH═CH— or a single bond; with the proviso that heteroatoms are not directly linked to each other, and $a_1$, $a_2$, $a_3$ each independently represents an integer from 0 to 3, such that $a_1+a_2+a_3 \leq 6$; preferably $a_3$ is 0 and $a^1+a^2 \leq 4$.

Most preferred $S^1$ represents a single bond or a spacer unit such as a straight-chain or branched $C_1$-$C_{14}$alkylen, wherein one or more, preferably non adjacent, —CH$_2$— group may independently be replaced by a linking group and/or a group represented by formula (IV), wherein:

$C^1$, $C^2$ each independently represents a 1,4-phenylene, 2-methoxy-1,4-phenylene, 1,4-cyclohexylene or a 4,4'-biphenylene group; and $Z^1$, $Z^2$, $Z^{1a}$ each independently represents —COO—, —OCO—, —CH$_2$—CH$_2$—, —OCH$_2$—, —CH$_2$O—, —CH═CH—, —C≡C—, —CH═CH—COO—, —OCO—CH═CH— or a single bond; and $a_1$, $a_2$, $a_3$ are independently 0 or 1, preferably $a_3$ is 0.

Especially most preferred $S^1$ represents a straight-chain $C_1$-$C_{12}$alkylen, wherein one or more —CH$_2$— groups may be replaced by —O—, —O(CO)—, —(CO)O—, —NR$_1$CO—, —CONR$_1$—, wherein R$_1$ is hydrogen or $C_1$-$C_6$alkyl or a group of formula (IV), wherein:

$C^1$, $C^2$ each independently represents 1,4-phenylene; and
$Z^1$, $Z^2$, $Z^{1a}$ each independently represents —COO—, —OCO—, —CH$_2$—CH$_2$—, —OCH$_2$—, —CH$_2$O—, —CH═CH—, —C≡C—, —CH═CH—COO—, —OCO—CH═CH—, or a single bond; and $a_1$, $a_2$, $a_3$ are independently 0 or 1, preferably $a_3$ is 0.

More preferred $S^2$ represents a spacer unit such as a straight-chain or branched $C_1$-$C_{24}$alkylen, wherein one or more —CH$_2$— groups is independently replaced by a group represented by the formula (IV), wherein:

$C^1$, $C^2$ are selected from group $G^1$, with the above given meaning; and $Z^1$, $Z^2$, $Z^{1a}$ each independently represents —O—, —CO—, —COO—, —OCO—, —COCF$_2$—, —CF$_2$CO—, —CH$_2$—CH$_2$—, —OCH$_2$—, —CH$_2$O—, —CH═CH—, —C≡C—, —CH═CH—COO—, —OCO—CH═CH— or a single bond; with the proviso that heteroatoms are not directly linked to each other, and $a_1$, $a_2$, $a_3$ are each independently represents an integer from 0 to 3, such that $a_1+a_2+a_3 \leq 6$, and preferably $a_1+a_2 \leq 4$ and $a_3$ is 0; and wherein preferably $S^2$ is linked to A via $Z^1$.

Most preferred $S^2$ represents a straight-chain or branched $C_1$-$C_{12}$alkylen, wherein one or more —CH$_2$— group is independently be replaced by a group represented by the formula (IV), and more most preferred $S^2$ represents a group of formula (IV), wherein $C^1$, $C^2$ each independently represents a 1,4-phenylene which is unsubstituted or mono or poly-substituted by a halogen atom, and/or by an alkoxy, alkylcarbonyloxy or an alkyloxycarbonyl group, having form 1 to 10 carbon atoms, 1,4-cyclohexylene or a 4,4'-biphenylene group; and $Z^1$, $Z^2$, $Z^{1a}$ each independently represents —COO—, —OCO—, —CH$_2$—CH$_2$—, —OCH$_2$—, —CH$_2$O—, —CH═CH—, —C≡C—, —CH═CH—COO—, —OCO—CH═CH— or a single bond; and $a_1$, $a_2$, $a_3$ are independently 0 or 1, wherein preferably $S^2$ is linked to A via $Z^1$.

Especially most preferred $S^2$ represents a group of formula (IVa)

   (IVa)

wherein:

$C^1$ represents a non-aromatic, aromatic, unsubstituted or substituted carbocyclic or heterocyclic group, preferably selected from a compound of group G1, and $Z^1$, $Z^{1a}$ each independently from each other represent —COO—, —OCO—, —OCO(C$_1$-C$_6$)alkyl, —COOCH$_2$(C$_1$-C$_6$)alkyl-, —CH$_2$—CH$_2$—, —OCH$_2$—, —CH$_2$O—, —CH═CH—, —C≡C—, —CH═CH—COO—, —OCO—CH═CH—, or a single bond, or a straight-chain or branched, substituted or unsubstituted C$_1$-C$_8$alkylen, wherein one or more —CH$_2$— group may independently from each other be replaced by a linking group, preferably by —O—, as described above;

$a_1$, $a_3$ represents independently from each other 1, wherein preferably $S^2$ is linked to A via $Z^1$.

Further, especially most preferred $S^2$ represents a group of formula (IVa)

   (IVa)

wherein:

$C^1$ represents a 1,4-phenylene which is unsubstituted or mono or poly-substituted by a halogen atom, and/or by an alkoxy, alkylcarbonyloxy or an alkyloxycarbonyl group, having form 1 to 10 carbon atoms, $Z^1$, $Z^{1a}$ each independently from each other represent —COO—, —OCO—, —CH$_2$—CH$_2$—, —OCH$_2$—, —CH$_2$O—, —CH═CH—, —C≡C—, —CH═CH—COO—, —OCO—CH═CH—, or a single bond, or a straight-chain or branched, substituted or unsubstituted C$_1$-C$_8$alkylen, wherein one or more —CH$_2$— group may independently from each other be replaced by a linking group as described above, preferably by —O—, —COO—, —OCO—, $a_1$, $a_3$ represents independently from each other 1, wherein preferably $S^2$ is linked to A via $Z^1$.

Another preferred embodiment of the present invention relates to a diamine compound (I), referring to any of the preceding definitions comprising these diamine compounds, wherein A represents phenanthrylene, biphenylene, naphthylene, or phenylene, which is unsubstituted or mono- or poly-substituted by a halogen atom, hydroxy group and/or by a polar group, preferably nitro, cyano, carboxy; and/or by acryloyloxy, methacryloyloxy, vinyl, vinyloxy, allyl, allyloxy, and/or by a cyclic, straight-chain or branched C$_1$-C$_{12}$alkyl residue, which is unsubstituted, mono- or poly-substituted by fluorine and/or chlorine, wherein one or more —CH$_2$— group may independently be replaced by a linking group and or an aromatic or an alicyclic group, and wherein the compound residue (Ia) of compound of formula (I) as described above

   (Ia)

represents a straight-chain or branched C$_1$-C$_{12}$fluoralkyl group, wherein

F is fluorine, and $x_1$ is an integer from 1 to 10,

B represents a straight-chain or branched C$_1$-C$_{12}$alkyl group, which is unsubstituted or in addition to its fluorine substituent(s) substituted by di-(C$_1$-C$_{16}$alkyl)amino, C$_1$-C$_6$alkyloxy, nitro, cyano and/or chlorine; and wherein one or more —CH$_2$— group may independently from each other be replaced by a linking group selected from —O—, —CO—, —CO—O—, —O—CO—, —NR$^1$—, —NR$^1$—CO—, —CO—NR$^1$— and —CH═CH—, wherein:

$R^1$ represents a hydrogen atom or C$_1$-C$_6$alkyl;

with the proviso that oxygen atoms are not directly linked to each other;

and wherein the C$_1$-C$_{12}$fluoralkyl group has terminal units selected from —CF$_2$H and —CF$_3$, preferably selected from —CF$_2$H or —CF$_3$, —CF$_2$CF$_3$, —CF$_2$CHF$_2$, —(CF$_2$)$_2$CF$_3$, —(CF$_2$)$_2$CHF$_2$, —(CF$_2$)$_3$CHF$_2$, —(CF$_2$)$_3$CF$_3$, —CF(CF$_3$)$_2$ and —CF$_2$(CHF)CF$_3$, D represents an optionally substituted aliphatic, aromatic or alicyclic diamine group having from 1 to 40 carbon atoms selected from formula (III),

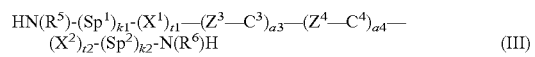   (III)

wherein $k^1$, $k^2$ are 0 or 1, and $t^1$, $t^2$ are 0, and $R^5$, $R^6$ are identical and represent a hydrogen atom, a methyl, an ethyl or an isopropyl group; and $C^3$, $C^4$ independently from each other are selected from compound of a group $G^2$ as described above;

$Z^3$ represents a group selected from —CH(OH)—, —CH(CH$_3$)—, —C(CH$_3$)$_2$—, —CO—, —COO—, —OCO—, —COCF$_2$—, —CF$_2$CO— or a single bond; and $Z^4$ has one of the meanings of $Z^3$ or represents a substituted or unsubstituted straight-chain or branched C$_1$-C$_{20}$alkylene, in which one or more, preferably non-adjacent, —CH$_2$— group may independently from each other be replaced by cyclohexylen, phenylen, aromatic or non-aromatic N-heterocycle; or by a heteroatom and/or by an oxygen atom; and/or one or more carbon-carbon single bond is replaced by a carbon-carbon double or a carbon-carbon triple bond;

$a^3$, $a^4$ each independently represents an integer from 0 to 2 such that $a^3+$-$a^4$≦3;

$Sp^1$, $Sp^2$, $X^1$, $X^2$ have the same meaning as described above;

E represents an phenylene, an oxygen atom or a —N(H)— group;

$S^1$ represents a single bond or a cyclic, straight-chain or branched, substituted or unsubstituted C$_1$-C$_{24}$alkylen, wherein one or more —CH$_2$— group may independently from each other be replaced by a linking group as described above;

$S^2$ represents a non-aromatic, aromatic, unsubstituted or substituted carbocyclic or heterocyclic group of formula (IV):

$$—(Z^1—C^1)_{a1}—(Z^2—C^2)_{a2}—(Z^{1a})_{a3}— \quad (IV)$$

wherein:
$C^1$, $C^2$ each independently represents a non-aromatic, aromatic, unsubstituted or substituted carbocyclic or heterocyclic group, and
$Z^1$, $Z^2$, $Z^{1a}$ each independently represents a bridging group, and
$a^1$, $a^2$, $a^3$ each independently represents an integer from 0 to 3, such that $a^1+a^2+a^3 \leqq 6$, preferably $a^1+a^2 \leqq 4$ and $a^3$ is 0; wherein the bridging groups $Z^1$, $Z^{1a}$ and $Z^2$ are as described above,
X, Y are hydrogen atoms, and
n is 1, 2 or 3, and n1 is 1 or 2; preferably n1 is 1.
with the proviso that if n is 2 or 3 each A, B, $x_1$, D, E, $S^1$ and $S^2$ may be identical or different, and if n1 is 2 each B, x1 may be identical or different.

A more preferred embodiment of the present invention relates to diamine compounds (I), referring to any of the preceding definitions, and to alignment materials comprising these diamine compounds wherein
A represents a biphenylene, naphthylene or phenylene group, which is unsubstituted or mono- or poly-substituted by a halogen atom, a hydroxy group, and/or by acryloyloxy, and/or methacryloyloxy groups, and/or by straight-chain or branched alkyl, alkoxy, alkylcarbonyloxy, and/or alkyloxycarbonyl groups having from 1 to 20 carbon atoms, and
wherein the compound residue (Ia) of compound of formula (I) as described in claim 1

(Ia)

represents a straight-chain or branched $C_1$-$C_8$fluoralkyl group, wherein
F is fluorine, and
$x_1$ is an integer from 1 to 9,
B represents a straight-chain or branched $C_1$-$C_8$alkyl group, which is unsubstituted or in addition to its fluorine substituent(s) substituted by di-($C_1$-$C_{16}$alkyl)amino, $C_1$-$C_6$alkyloxy, nitro, cyano and/or chlorine; and wherein one or more —$CH_2$— group may independently from each other be replaced by a linking group selected from —O—, —CO—, —CO—O—, —O—CO—, —$NR^1$—, —$NR^1$—CO—, —CO—$NR^1$— and —CH=CH—, wherein:
$R^1$ represents a hydrogen atom or $C_1$-$C_8$alkyl; with the proviso that oxygen atoms are not directly linked to each other; and
D represents an optionally substituted aliphatic, aromatic or alicyclic diamine group having from 1 to 40 carbon atoms, represented by formula (III) and is most preferably selected from the following group of structures: substituted or unsubstituted o-phenylenediamine, p-phenylenediamine, m-phenylenediamine, aminophenylen-$Z^4$-phenylenamino; or m-phenylenediamine with a substituted or unsubstituted straight-chain or branched $C_1$-$C_{20}$alkylene group, in which one or more —$CH_2$— group may independently from each other be replaced by a non-aromatic, aromatic, unsubstituted or substituted carbocyclic or heterocyclic group, or a heteroatom and/or by a bridging group; wherein $Z^4$ has the above given meaning; benzidine, diaminofluorene, 3,4-diaminobenzoic acid, 3,4-diaminobenzyl alcohol dihydrochloride, 2,4-diaminobenzoic acid, L-(+)-threo-2-amino-1-(4-aminophenyl)-1,3-propanediol, p-aminobenzoic acid, [3, 5-3h]-4-amino-2-methoxybenzoic acid, L-(+)-threo-2-(N,N-dimethylamino)-1-(4-aminophenyl)-1,3-propanediol, 2,7-diaminofluorene, 4,4'-diaminooctafluorobiphenyl, 3,3'-diaminobenzidine, 2,7-diamine-9-fluorenone, 3,5,3',5'-tetrabromo-biphenyl-4,4'-diamine, 2,2'-dichloro[1,1'-biphenyl]-4,4'-diamine, 3,9-diamine-1,11-dimethyl-5,7-dihydro-dibenzo(a,c)cyclohepten-6-one, dibenzo(1,2) dithiine-3,8-diamine, 3,3'-diaminobenzophenone, 3,3'-diaminediphenylmethane, 4,4-bis-(3-amino-4-hydroxyphenyl)-valeric acid, 2,2-bis(3-amino-4-hydroxyphenyl)hexafluoropropane, 2,2-bis(3-amino-4-methylphenyl)hexafluoropropane, tetrabromo methylenedianiline, 2,7-diamine-9-fluorenone, 2,2-bis(3-aminophenyl)hexafluoropropane, bis-(3-amino-4-chlorophenyl)-methanone, bis-(3-amino-4-dimethylamino-phenyl)-methanone, 3-[3-amino-5-(trifluoromethyl)benzyl]-5-(trifluoromethyl)aniline, 1,5-diaminonaphthalene, benzidine-3,3'-dicarboxylic acid, 4,4'-diamino-1,1'-binaphthyl, 4,4'-diaminediphenyl-3,3'-diglycolic acid, dihydroethidium, o-dianisidine, 2,2'-dichloro-5,5'-dimethoxybenzidine, 3-methoxybenzidine, 3,3'-dichlorobenzidine (diphenyl-d6), 2,2'-bis(trifluoromethyl)benzidine, 3,3'-bis (trifluoromethyl)benzidine, 3,3'-dichlorobenzidine-d6, tetramethylbenzidine, di-(aminophenyl)alkylen
and
from amino compounds listed below, which do not carry two amino groups and are taken as derivatives with at least one additional amino group: aniline, 4-amino-2,3, 5,6-tetrafluorobenzoic acid, 4-amino-3,5-diiodobenzoic acid, 4-amino-3-methylbenzoic acid, 4-amino-2-chlorobenzoic acid, 4-aminosalicylic acid, 4-aminobenzoic acid, 4-aminophthalic acid, 1-(4-aminophenyl)ethanol, 4-aminobenzyl alcohol, 4-amino-3-methoxybenzoic acid, 4-aminophenyl ethyl carbinol, 4-amino-3-nitrobenzoic acid, 4-amino-3,5-dinitrobenzoic acid, 4-amino-3,5-dichlorobenzoic acid, 4-amino-3-hydroxybenzoic acid, 4-aminobenzyl alcohol hydrochloride, 4-aminobenzoic acid hydrochloride, pararosaniline base, 4-amino-5-chloro-2-methoxybenzoic acid, 4-(hexafluoro-2-hydroxyisopropyl)aniline, piperazine-p-amino benzoate, 4-amino-3,5-dibromobenzoic acid, isonicotinic acid hydrazide p-amino-salicylate salt, 4-amino-3,5-diiodosalicylic acid, 4-amino-2-methoxybenzoic acid, 2-[2-(4-aminophenyl)-2-hydroxy-1-(hydroxymethyl)ethyl]isoindoline-1,3-dione, 4-amino-2-nitrobenzoic acid, ethyl 2-(4-aminophenyl)-3,3,3-trifluoro-2-hydroxypropanoate, ethyl 2-(4-amino-3-methylphenyl)-3,3,3-trifluoro-2-hydroxypropanoate, ethyl 2-(4-amino-3-methoxyphenyl)-3,3,3-trifluoro-2-hydroxypropanoate, 4-aminonaphthalene-1,8-dicarboxylic acid, 4-amino-3-chloro-5-methylbenzoic acid, 4-amino-2,6-dimethylbenzoic acid, 4-amino-3-fluorobenzoic acid, 4-amino-5-bromo-2-methoxybenzenecarboxylic acid, 3,3'-tolidine-5-sulfonic acid, or their derivatives, again with the proviso that compounds listed which do not carry two amino groups are taken as derivatives with at least one additional amino group, and
E represents an oxygen atom or a —N(H)— group;
$S^1$ represents a spacer unit such a straight-chain or branched $C_1$-$C_{14}$alkylene groups, wherein one or more —$CH_2$— groups may independently be replaced by a group represented by formula (IV) as defined above, wherein:

$C^1$, $C^2$ each independently represents a 1,4-phenylene, 2-methoxy-1,4-phenylene, 1,4-cyclohexylene or a 4,4'-biphenylene group; and $Z^1$, $Z^2$, $Z^{1a}$ each independently represents —COO—, —OCO—, —CH$_2$—CH$_2$—, —OCH$_2$—, —CH$_2$O—, —CH=CH—, —C≡C—, —CH=CH—COO—, —OCO—CH=CH— or a single bond; and $a^1$, $a^2$, $a^3$ are independently 0 or 1; preferably $a^3$ is 0, $S^2$ represents a spacer unit of formula (IV) as defined above, wherein preferably $S^2$ is linked to A via $Z^1$; and wherein $C^1$, $C^2$ each independently represents a 1,4-phenylene which is unsubstituted or mono or poly-substituted by a halogen atom, and/or by an alkoxy, alkylcarbonyloxy or an alkyloxycarbonyl group, having form 1 to 10 carbon atoms, 1,4-cyclohexylene or a 4,4'-biphenylene group; and $Z^1$, $Z^2$, $Z^{1a}$ each independently represents —O—, —COO—, —OCO—, —CH$_2$—CH$_2$—, —OCH$_2$—, —CH$_2$O—, —CH=CH—, —C≡C—, —CH=CH—COO—, —OCO—CH=CH— or a single bond; and $a^1$, $a^2$, $a^3$ are independently 0 or 1; preferably $a^3$ is 0, n is 1 or 2, and n1 is 1, or 2, preferably 1;

with the proviso that if n is 2 or 3 each A, B, $x_1$, D, E, $S^1$, $S^2$, X, Y may be identical or different; and if n1 is 2 each B, $x_1$ is identical or different.

Another preferred embodiment of the present invention relates to a diamine compound represented by one of the general formula (I), referring to any of the preceding definitions, and preferably to alignment materials comprising this diamine compound wherein A represents 1,4-phenylene, which is unsubstituted or mono- or poly-substituted by a halogen atom, and/or by acryloyloxy or methacryloyloxy, and/or by an alkoxy, alkylcarbonyloxy or an alkyloxycarbonyl group, having from 1 to 10 carbon atoms, and wherein the compound residue (Ia) of compound of formula (I) as described above

(Ia)

represents a straight-chain or branched $C_1$-$C_8$fluoralkyl group, wherein

F is fluorine, and $x_1$ is an integer from 1 to 9,

B represents a straight-chain or branched $C_1$-$C_8$alkyl group, which is unsubstituted or in addition to its fluorine substituent(s) substituted by di-($C_1$-$C_{16}$alkyl)amino, $C_1$-$C_6$alkyloxy, nitro, cyano and/or chlorine; and wherein one or more —CH$_2$— group may independently from each other be replaced by a linking group selected from —O—, —CO—, —CO—O—, —O—CO—, —NR$^1$—, —NR$^1$—CO—, —CO—NR$^1$— and —CH=CH—, wherein:

$R^1$ represents a hydrogen atom or $C_1$-$C_6$alkyl;

with the proviso that oxygen atoms are not directly linked to each other; and wherein the $C_1$-$C_{12}$fluoralkyl group has terminal units selected from —CF$_2$H and —CF$_3$, preferably selected from —CF$_2$H or —CF$_3$, —CF$_2$CF$_3$, —CF$_2$CHF$_2$, —(CF$_2$)$_2$CF$_3$, —(CF$_2$)$_2$CHF$_2$, —(CF$_2$)$_3$CHF$_2$, —(CF$_2$)$_3$CF$_3$, —CF(CF$_3$)$_2$ and —CF$_2$(CHF)CF$_3$, D represents an unsubstituted o-phenylenediamine, p-phenylenediamine, m-phenylenediamine, biphenyldiamine, aminophenylen-$Z^4$-phenylenamino, naphthylenediamine, or a m-phenylenediamine with a substituted or unsubstituted straight-chain or branched $C_1$-$C_{20}$alkylene group, in which one or more —CH$_2$— group may independently from each other be replaced by a non-aromatic, aromatic, unsubstituted or substituted carbocyclic or heterocyclic group, or a heteroatom and/or by a bridging group;

wherein $Z^4$ is as defined above;

E represents an oxygen atom;

$S^1$ represents a single bond or a straight-chain $C_1$-$C_8$alkylene group, wherein one —CH$_2$— group may be may be replaced by —O—, —OCO—, —COO—, —NR$_1$CO—, —CONR$_1$—, wherein $R_1$ is hydrogen or $C_1$-$C_6$alkyl, $S^2$ is replaced by a group of formula (IVa) as described above, wherein:

$C^1$ represents a 1,4-phenylene which is unsubstituted or mono or poly-substituted by a halogen atom, and/or by an alkoxy, alkylcarbonyloxy or an alkyloxycarbonyl group, having form 1 to 10 carbon atoms, $Z^1$, $Z^{1a}$ represents —O—, —COO—, —OCO—, —COO($C_1$-$C_6$)alkylen, —OCO($C_1$-$C_6$)alkylen, —CH$_2$—CH$_2$—, —OCH$_2$—, —CH$_2$O—, —CH=CH—, —C≡C—, —CH=CH—COO—, —OCO—CH=CH—, or a single bond;

X, Y are hydrogen atoms, and n is 1 or 2, and n1 is 1 or 2 and preferably 1;

with the proviso that if n or n1 is 2 each A, B, $x_1$, D, E, $S^1$ and $S^2$ may be identical or different; and if n1 is 2 each B, $x_1$ is identical or different.

Most preferred embodiment of the present invention relates to diamine compounds represented by one of the general formula (I), referring to any of the preceding definitions, and to alignment materials comprising these diamine compounds wherein $S^2$ is replaced by a group of formula (IV), wherein:

$C^1$ represents 1,4-phenylene; and $Z^1$, $Z^{1a}$ represent each independently from each other —COO—, —OCO—, —CH$_2$—CH$_2$—, —OCH$_2$—, —CH$_2$O—, —CH=CH—, —C≡C—, —CH=CH—COO—, —OCO—CH=CH—, or a single bond;

$a_1$ represents 1, and $a_3$ represents 0

$S^2$ is linked to A via $Z^1$.

Especially most preferred embodiment of the present invention relates to Diamine compounds of formulae (VI), (VII), (VIII), (IX), (X), (XI), (XIa) and (XIb)

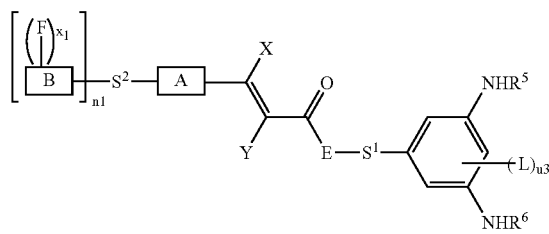
(VI)
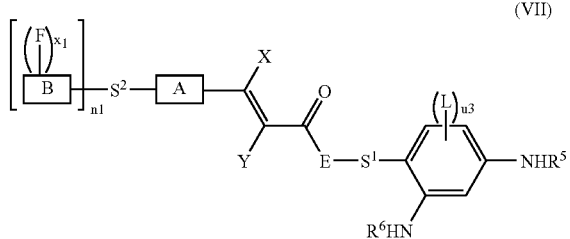
(VII)
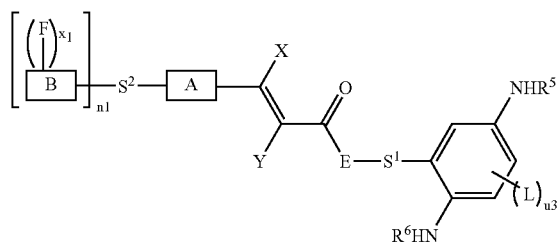
(VIII)
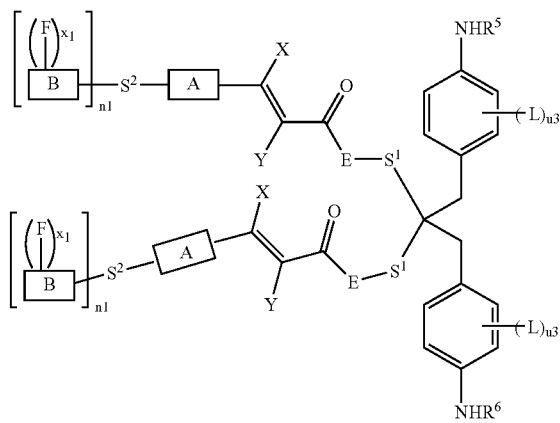
(IX)
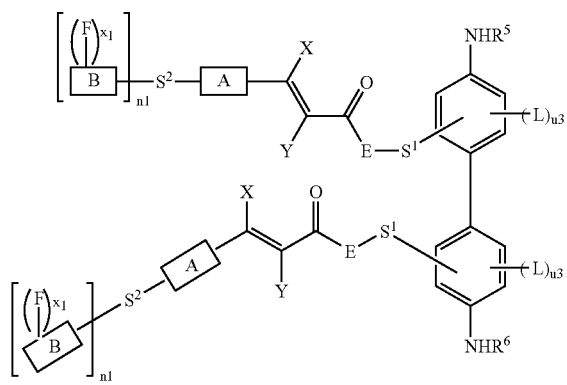
(X)
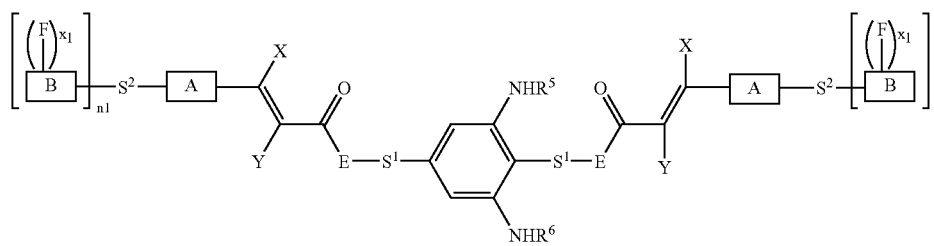
(XI)

-continued (XIa)

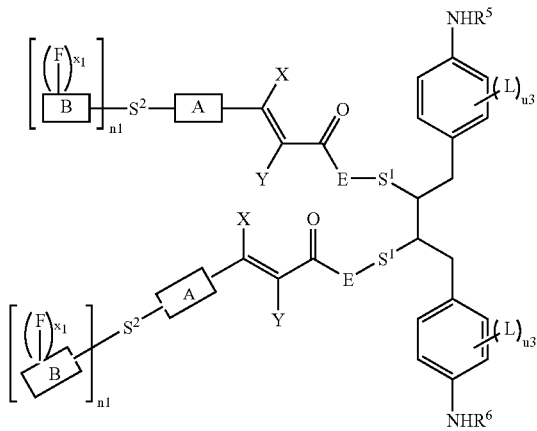

(XIb)

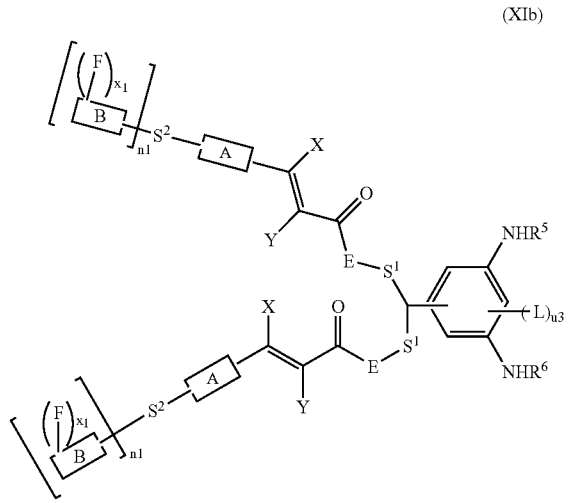

wherein
A, B, $x_1$, n, n1, D, E, $S^2$, $S^1$, X and Y, $R^5$, $R^6$ and $Z^4$ have the above given meanings and preferences as given above; preferably n1 is 1;

L is —CH$_3$—, —OCH$_3$, —COCH$_3$, nitro, cyano, halogen, CH$_2$=CH—, CH$_2$=C(CH$_3$)—, CH$_2$=CH—(CO)O—, CH$_2$=CH—O—, CH$_2$=C(CH$_3$)—(CO)O—, or CH$_2$=C(CH$_3$)—O—, u3 is an integer from 0 to 2.

Further, especially most preferred embodiment of the present invention relates to diamine compounds of formula (XII)

(XII)

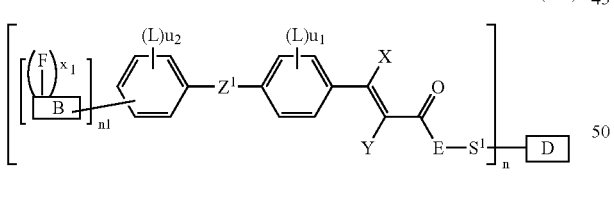

wherein $x_1$, n, n1, D, E, $S^1$, X, Y, $Z^1$, L, $u_1$ and $u_2$ have the above given meanings and preferences.

Preferred diamine compounds of formula (XII) are compounds, wherein $Z^1$ is —COO—, —OCO—, —OCO(C$_1$-C$_6$)alkylen or —COO(C$_1$-C$_6$)alkylen, or a single bond, or a straight-chain or branched, substituted or unsubstituted C$_1$-C$_8$alkylen, wherein one or more —CH$_2$— group may independently from each other be replaced independently from each other by a linking group, preferably by —O—.

Further, especially most preferred diamine is compound of formula (XIIa)

(XIIa)

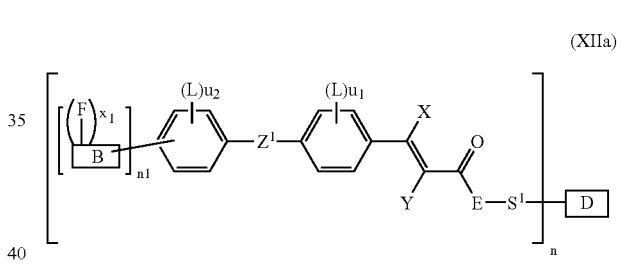

wherein n, n1, D, E, $S^1$, $Z^1$, L, $u_1$ and $u_2$ X and Y have the above given meanings and preferences as above, and wherein the following compound residue

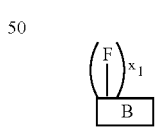

represents a straight-chain or branched C$_1$-C$_8$fluoralkyl group, wherein
F is fluorine, and
$x_1$ is an integer from 1 to 9,
B represents a straight-chain or branched C$_1$-C$_8$alkyl group, which is unsubstituted or in addition to its fluorine substituent(s) substituted by di-(C$_1$-C$_{16}$alkyl)amino, C$_1$-C$_6$alkyloxy, nitro, cyano and/or chlorine; and wherein one or more —CH$_2$— group may independently be replaced by a linking group selected from —O—, —CO—, —CO—O—, —O—CO—, —NR$^1$—, —NR$^1$—CO—, —CO—NR$^1$— and —CH=CH—, wherein:

$R^1$ represents a hydrogen atom or $C_1$-$C_6$alkyl;
with the proviso that oxygen atoms are not directly linked to each other;
and
wherein the $C_1$-$C_{12}$fluoralkyl group has terminal units selected from —$CF_2H$ and —$CF_3$, preferably selected from
—$CF_2H$ or —$CF_3$, —$CF_2CF_3$, —$CF_2CHF_2$, —$(CF_2)_2CF_3$, —$(CF_2)_2CHF_2$, —$(CF_2)_3CHF_2$, —$(CF_2)_3CF_3$, —$CF(CF_3)_2$ and —$CF_2(CHF)CF_3$.

Most preferred diamine is and
wherein the following compound residue

represents a straight-chain or branched $C_1$-$C_8$fluoralkyl group, wherein

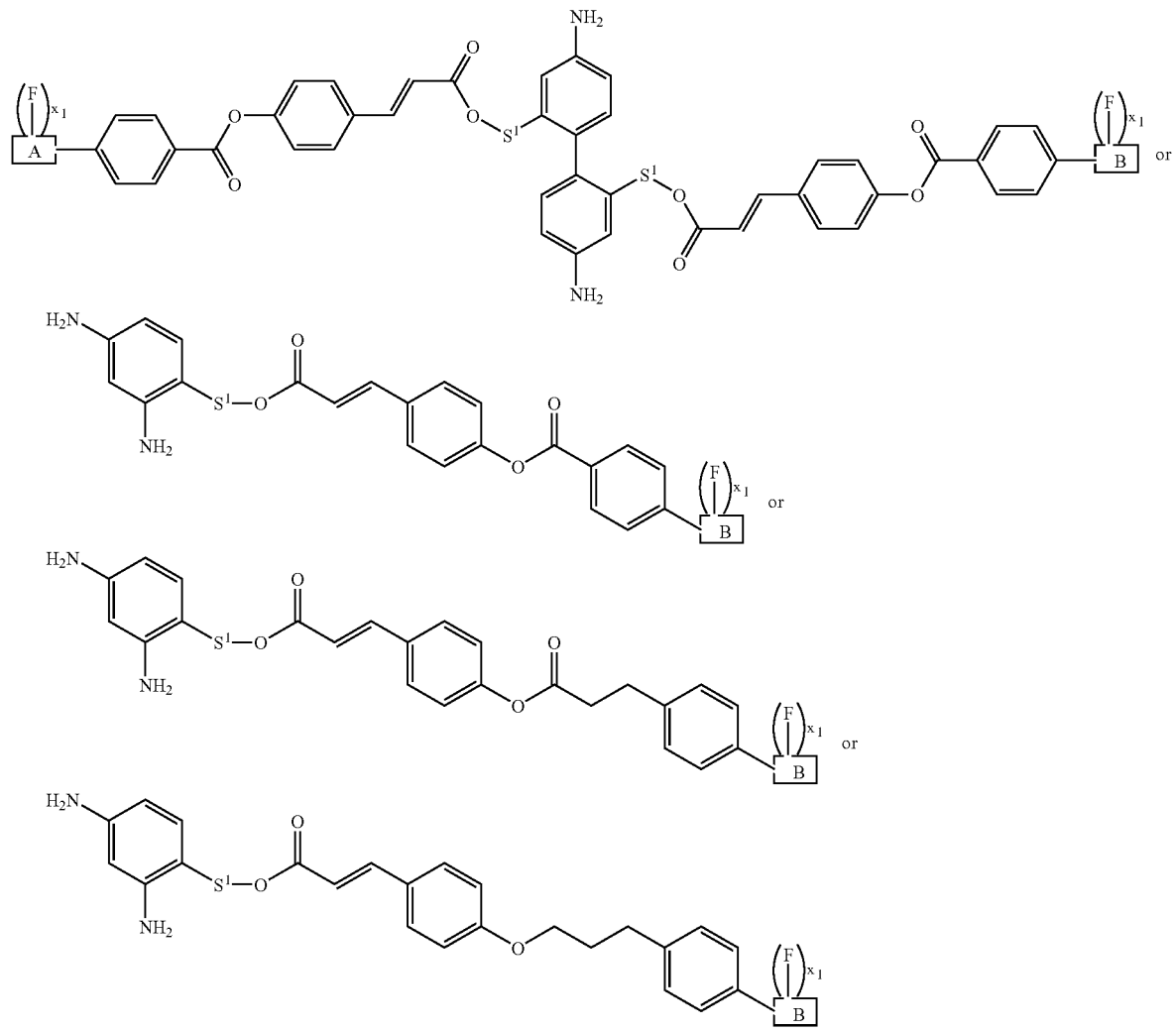

wherein $S^1$ has the above given meanings and preferences as above;
especially most preferred $S^1$ represents a straight-chain $C_1$-$C_{12}$alkylen, wherein one or more —$CH_2$— group may be replaced by —O—, —O(CO)—, —(CO)O—, —$NR_1$CO—, —$CONR_1$—, wherein $R_1$ is hydrogen or $C_1$-$C_6$alkyl or a group of formula (IV), wherein:
$C^1$, $C^2$ each independently represents 1,4-phenylene; and
$Z^1$, $Z^2$, $Z^{1a}$ each independently represents —COO—, —OCO—, —$CH_2$—$CH_2$—, —$OCH_2$—, —$CH_2O$—, —CH=CH—, —C≡C—, —CH=CH—COO—, —OCO—CH=CH—, or a single bond; and
$a_1$, $a_2$, $a_3$ are independently 0 or 1, preferably $a_3$ is 0;

F is fluorine, and
$x_1$ is an integer from 1 to 9,
B represents a straight-chain or branched $C_1$-$C_8$alkyl group, which is unsubstituted or in addition to its fluorine substituent(s) substituted by di-($C_1$-$C_{16}$alkyl)amino, $C_1$-$C_6$alkyloxy, nitro, cyano and/or chlorine; and wherein one or more —$CH_2$— group may independently be replaced by a linking group selected from —O—, —CO—, —CO—O—, —O—CO—, —$NR^1$—, —$NR^1$—CO—, —CO—$NR^1$— and —CH=CH—, wherein:
$R^1$ represents a hydrogen atom or $C_1$-$C_6$alkyl;
with the proviso that oxygen atoms are not directly linked to each other;

and wherein the $C_1$-$C_8$ fluoralkyl group has terminal units selected from —$CF_2H$ and —$CF_3$, preferably selected from
—$CF_2H$ or —$CF_3$, —$CF_2CF_3$, —$CF_2CHF_2$, —$(CF_2)_2CF_3$, —$(CF_2)_2CHF_2$, —$(CF_2)_3CHF_2$, —$(CF_2)_3CF_3$, —$CF(CF_3)_2$ and —$CF_2(CHF)CF_3$.

Another preferred embodiment of the present invention relates to diamine compounds represented by the general formula (I), which may be used in the subsequent manufacturing processes as such or in combination with one or more additional other diamines, preferably those of formula (L) as given below.

The diamine (L) represents an optionally substituted aliphatic, aromatic or alicyclic diamino group having from 1 to 40 carbon atoms and preferably made from or selected from the following group of structures: aniline, p-phenylenediamine, m-phenylenediamine, benzidine, diaminofluorene, or their derivatives, with the proviso that compounds listed which do not carry two amino groups are taken as derivatives with at least one additional amino group, and more preferably made from or selected from the following commercially available amino compounds (example of suppliers: Aldrich, ABCR, ACROS, Fluka) which can also be used as comonomers:

4-amino-2,3,5,6-tetrafluorobenzoic acid
4-amino-3,5-diiodobenzoic acid, 3,4-diaminobenzoic acid
4-amino-3-methylbenzoic acid,
4-amino-2-chlorobenzoic acid
4-aminosalicylic acid
4-aminobenzoic acid
4-aminophthalic acid
1-(4-aminophenyl)ethanol
4-aminobenzyl alcohol
4-amino-3-methoxybenzoic acid
4-aminophenyl ethyl carbinol
4-amino-3-nitrobenzoic acid
4-amino-3,5-dinitrobenzoic acid
4-amino-3,5-dichlorobenzoic acid
4-amino-3-hydroxybenzoic acid
4-aminobenzyl alcohol hydrochloride
4-aminobenzoic acid hydrochloride
pararosaniline base
4-amino-5-chloro-2-methoxybenzoic acid
4-(hexafluoro-2-hydroxyisopropyl)aniline
piperazine-p-amino benzoate
4-amino-3,5-dibromobenzoic acid
isonicotinic acid hydrazide p-aminosalicylate salt
4-amino-3,5-diiodosalicylic acid
4-amino-2-methoxybenzoic acid
2-[2-(4-aminophenyl)-2-hydroxy-1-(hydroxymethyl)ethyl]isoindoline-1,3-dione
4-amino-2-nitrobenzoic acid
2,4-diaminobenzoic acid
p-aminobenzoic acid,
[3, 5-3h]-4-amino-2-methoxybenzoic acid
L-(+)-threo-2-amino-1-(4-aminophenyl)-1,3-propanediol
L-(+)-threo-2-(N,N-dimethylamino)-1-(4-aminophenyl)-1,3-propanediol
ethyl 2-(4-aminophenyl)-3,3,3-trifluoro-2-hydroxypropanoate
ethyl 2-(4-amino-3-methylphenyl)-3,3,3-trifluoro-2-hydroxypropanoate
ethyl 2-(4-amino-3-methoxyphenyl)-3,3,3-trifluoro-2-hydroxypropanoate
3,4-diaminobenzyl alcohol dihydrochloride
4-aminonaphthalene-1,8-dicarboxylic acid
4-amino-3-chloro-5-methylbenzoic acid
4-amino-2,6-dimethylbenzoic acid
4-amino-3-fluorobenzoic acid
4-amino-5-bromo-2-methoxybenzenecarboxylic acid
2,7-diaminofluorene
4,4'-diaminooctafluorobiphenyl
3,3'-diaminobenzidine
3,3',5,5'-tetramethylbenzidine
3,3'-dimethoxybenzidine
o-tolidine
3,3'-dinitrobenzidine
2-nitrobenzidine
3,3'-dihydroxybenzidine
o-tolidine sulfone
benzidine,
3,3'-dichlorobenzidine
2,2',5,5'-tetrachlorobenzidine,
benzidine-3,3'-dicarboxylic acid
4,4'-diamino-1,1'-binaphthyl
4,4'-diaminodiphenyl-3,3'-diglycolic acid
dihydroethidium
o-dianisidine
2,2'-dichloro-5,5'-dimethoxybenzidine
3-methoxybenzidine
3,3'-dichlorobenzidine (diphenyl-d6),
2,7-diamino-9-fluorenone
3,5,3',5'-tetrabromo-biphenyl-4,4'-diamine
2,2'-bis(trifluoromethyl)benzidine
2,2'-dichloro[1,1'-biphenyl]-4,4'-diamine
3,9-diamino-1,11-dimethyl-5,7-dihydro-dibenzo(a,c)cyclohepten-6-one
3,3'-bis(trifluoromethyl)benzidine
dibenzo(1,2)dithiine-3,8-diamine
3,3'-tolidine-5-sulfonic acid
3,3'-dichlorobenzidine-d6 tetramethylbenzidine
3,3'-diaminobenzophenone, 3,3'-diaminodiphenylmethane,
4,4-bis-(3-amino-4-hydroxyphenyl)-valeric acid
2,2-bis(3-amino-4-hydroxyphenyl)hexafluoropropane
2,2-bis(3-amino-4-methylphenyl)hexafluoropropane tetrabromo methylenedianiline
2,7-diamino-9-fluorenone
2,2-bis(3-aminophenyl)hexafluoropropane
bis-(3-amino-4-chloro-phenyl)-methanone
bis-(3-amino-4-dimethylamino-phenyl)-methanone
3-[3-amino-5-(trifluoromethyl)benzyl]-5-(trifluoromethyl)aniline
1,5-diaminonaphthalene
or their derivatives, again with the proviso that compounds listed which do not carry two amino groups are taken as derivatives with at least one additional amino group.

Preferred examples of additional other diamines (L) are: ethylenediamine, 1,3-propylenediamine, 1,4-butylenediamine, 1,5-pentylenediamine, 1,6-hexylenediamine, 1,7-heptylenediamine, 1,8-octylenediamine, 1,9-nonylenediamine, 1,10-decylenediamine, 1,11-undecylenediamine, 1,12-dodecylenediamine, α,α'-diamino-m-xylene, α,α'-diamino-p-xylene, (5-amino-2,2,4-trimethylcyclopentyl)methylamine, 1,2-diaminocyclohexane, 4,4'-diaminodicyclohexylmethane, 1,3-bis(methylamino)cyclohexane, 4,9-dioxadodecane-1,12-diamine, 3,5-diaminobenzoic acid methyl ester, 3,5-diaminobenzoic acid hexyl ester, 3,5-diaminobenzoic acid dodecyl ester, 3,5-diaminobenzoic acid isopropyl ester, 4,4'-methylenedianiline, 4,4'-ethylenedianiline, 4,4'-diamino-3,3'-dimethyldiphenylmethane, 3,3',5,5'-tetramethylbenzidine, 4,4'-diaminodiphenyl sulfone, 4,4'-diaminodiphenyl ether, 1,5-diaminonaphthalene,3,3'-dimethyl-4,4'-diaminobiphenyl, 3,4'-diaminodiphenyl ether, 3,3'-diaminobenzophenone, 4,4'-diaminobenzophenone, 4,4'-diamino-2,2'-dimethylbibenzyl, bis[4-(4-aminophenoxy)phenyl]sulfone, 1,4-bis(4-aminophenoxy)benzene, 1,3-bis(4-aminophenoxy)benzene, 1,3-bis(3-aminophenoxy)benzene, 2,7-diaminofluorene, 9,9-bis(4-aminophenyl)fluorene, 4,4'-methylenebis(2-chloroaniline), 4,4'-bis(4-aminophenoxy)biphenyl, 2,2',5,5'-tetrachloro-4,4'-diaminobiphenyl, 2,2'-dichloro-4,4'-diamino-5,5'-dimethoxybiphenyl, 3,3'-dimethoxy-4,4'-diaminobiphenyl, 4,4'-(1,4-phenyleneisopropylidene)bisaniline, 4,4'-(1,3-phenyleneisopropylidene)bisaniline, 2,2-bis[4-(4-aminophenoxy)phenyl]propane, 2,2-bis[3-(4-aminophenoxy)phenyl]hexafluoropropane, 2,2-bis[3-amino-4-methylphenyl]hexafluoropropane, 2,2-bis(4-aminophenyl)hexafluoropropane, 2,2'-bis[4-(4-amino-2-trifluoromethylphenoxy)phenyl]hexafluoropropane, 4,4'-diamino-2,2'-bis(trifluoromethyl)biphenyl, and 4,4'-bis[(4-amino-2-trifluoromethyl)phenoxy]-2,3,5,6,2',3',5',6'-octafluorobiphenyl;

as well as diamines (L) disclosed in U.S. Pat. No. 6,340,506, WO 00/59966 and WO 01/53384, all of which are explicitly incorporated herein by reference;

The diamine compounds (L) according to the present invention may be prepared using methods that are known to a person skilled in the art.

In addition, preferred diamines (L) are the commercially available ones listed below:
Polymers
Poly(3,3',4,4'-benzophenonetetracarboxylic dianhydride-co-4,4'-oxydianiline/1,3-phenylenediamine), amic acid solution
Poly(3,3',4,4'-benzophenonetetracarboxylic dianhydride-co-4,4'-oxydianiline/1,3-phenylenediamine), amic acid solution
Poly(pyromellitic dianhydride-co-4,4'-oxydianiline), amic acid solution
Aromatic diamine
2,7-diaminofluorene
1,5-diaminoanthraquinone
2,6-diaminoanthraquinone
pararosaniline hydrochloride
3,6-acridinediamine
4,4'-diaminooctafluorobiphenyl
2,2'-dithiodianiline
3,3',5,5'-tetramethylbenzidine
3,3'-diaminodiphenyl sulfone
4,4'-diamino-2,2'-dimethylbibenzyl
4,4'-diaminodiphenyl ether
4,4'-dithiodianiline
4,4'-diaminodiphenyl sulfone
4,4'-diaminodiphenylmethane
4,4'-ethylenedianiline
3,3'-dimethoxybenzidine
2,2'-dithiobis(1-naphthylamine)
3,7-diamino-2-methoxyfluorene
3,6-diamino-10-methylacridinium chloride
propidium iodide
o-dianisidine dihydrochloride
2,7-diaminofluorene dihydrochloride
pararosaniline acetate
3,6-diamino-10-methylacridinium chloride hydrochloride
proflavine dihydrochloride
o-tolidine dihydrochloride
3,3',5,5'-tetramethylbenzidine dihydrochloride
3,3'-diaminobenzidine tetrahydrochloride
4,4'-diaminostilbene dihydrochloride
4,4'-diaminodiphenylamine sulfate
proflavine hemisulfate
2,2'-ethylenedianiline diphosphate
1,5-diamino-4,8-dihydroxyanthraquinone
o-tolidine
3,3'-diaminobenzophenone
3,3'-diaminodiphenylmethane
3,4'-diaminodiphenylmethane
2,2-bis[4-(4-aminophenoxy)phenyl]hexafluoropropane
4,4'-diamino-1,1'-dianthramide
3,3'-dinitrobenzidine
4,4'-diamino-5,5'-dimethyl-2,2'-biphenyldisulfonic acid
4,4'-diaminostilbene-2,2'-disulfonic acid
3-amino-4-hydroxyphenyl sulfone
4,4-bis-(3-amino-4-hydroxyphenyl)-valeric acid
2,2'-diamino-4,4'-difluorobibenzyl
2-amino-4-chlorophenyl disulfide
3,3'-(decamethylenedioxy)dianiline
3,3'-(pentamethylenedioxy)dianiline
4-(p-aminoanilino)-3-sulfoaniline
4-[3-(4-aminophenoxy)propoxy]aniline
2-nitrobenzidine
benzidine-3-sulfonic acid
4,4'-diaminodiphenyl sulfide
4,4'-diaminobenzanilide
n,n'-bis(3-aminophenylsulfonyl)ethylenediamine
2,2'-biphenyldiamine
3,4'-diaminodiphenyl ether
proflavine hemisulphate
phenosafranin
4,4'-diaminobenzophenone
2,2-bis(4-aminophenyl)hexafluoropropane
2,2-bis(3-amino-4-hydroxyphenyl)hexafluoropropane
2,2-bis(3-amino-4-methylphenyl)hexafluoropropane
3,3'-dihydroxybenzidine
3,3'-diamino-4,4'-dihydroxybiphenyl
4,4'-bis(4-aminophenoxy)biphenyl
2,2-bis[4-(4-aminophenoxy)phenyl]propane
1,4-bis(4-aminophenoxy)benzene
1,3-bis(4-aminophenoxy)benzene
bis[4-(4-aminophenoxy)phenyl]sulfone
9,9-bis(4-aminophenyl)fluorene
o-tolidine sulfone
benzidine
3,3'-dichlorobenzidine dihydrochloride
benzidine dihydrochloride
3,6-thioxanthenediamine-10,10-dioxide
4,4'-diamino-2,2'-biphenyldisulfonic acid
4,4'-azodianiline
2,5-bis-(4-aminophenyl)-(1,3,4)oxadiazole
3,3'-dimethylnaphthidine
benzidine sulfate
1,3-bis(3-aminophenoxy)benzene
3,3'-dichlorobenzidine
2,2',5,5'-tetrachlorobenzidine
4,4'-diamino-1,1'-binaphthyl
diamine bordeaux
benzoflavin
chrysaniline
2,2'-thiobis(5-aminobenzenesulfonic acid)
4,4'-methylene-bis(2-chloroaniline)
tetrabromo methylenedianiline
4,4'-diamino-3,3'-dinitrodiphenyl ether
benzidine pyrophosphate
3,6-diaminothioxanthene-10-dioxide, dihcl
4,4"-diamino-p-terphenyl
1,8-diamino-4,5-dihydroxyanthraquinone
bis(p-aminophenoxy)dimethylsilane
bis[4-(3-aminophenoxy)phenyl]sulfone
4,4'-methylenedi-2,6-xylidine 2-aminobenzaldehyde-ethylene-diimine
3-methylbenzidine dihydrochloride
3,3'-diethylbenzidine dihydrochloride
3,6-diaminoacridine hydrochloride
4,4'-diamino-5,5'-dimethyl-2,2'-biphenyl disulfonic acid disodium salt
4,4'-methylenebis(3-chloro-2,6-diethylaniline)
4,4'-methylene-bis-(2,6-diethylaniline)
4,4'-methylenebis-(2,6-diisopropylaniline)
toluoylenediamine
3,8-diamino-6-phenylphenanthridine
thionin perchlorate
dihydroethidium
thionin
4,4-diamino benzene sulfonyl anilide
o-dianisidine hcl
2,2'-dichloro-5,5'-dimethoxybenzidine
3-methoxybenzidine
2,2'-(hexamethylenedioxy)dianiline
2,2'-(pentamethylenedioxy)dianiline
2,2'-(ethylenedioxy)dianiline
4-[4-(4-aminophenoxy)butoxy]aniline
2,2'-diamino-4'-methoxy-4-methylbenzanilide
5,5'-dimethyl-2,2'-dinitrobenzidine
n,n'-bis(2-aminophenyl)-1,3-propanediamine
3,4'-diaminochalcone
2,3',4,5',6-pentaphenyl-3,4'-biphenyldiamine
2-([1-(4-(1-[(2-aminophenyl)thio]-2-nitroethyl)phenyl)-2-nitroethyl]thio)anilin
2-((2-[(2-aminophenyl)thio]ethyl)thio)aniline
2-((4-[(2-aminophenyl)thio]but-2-enyl)thio)aniline
4,4'-diamino-3,3'-dimethyldiphenyl methane
2,2'-diamino-bibenzyl
trimethylene bis(4-aminobenzoate)
fluoresceinamine
benzidines mixture
3-nitro-4,4'-methylenedianiline
4,4-diamino-2,2'-dichlorodiphenyl disulfide
1,6-diaminopyrene
1,8-diaminopyrene
3,6-diaminocarbazole
4,4'(5')-diamino-[2,4]-dibenzo-18-crown-6,dihydrochloride
4,4'-diaminostilbene-2,2'-disulfonic acid, disodium salt
(r)-(+)-2,2'-diamino-1,1'-binaphthyl
proflavine hemisulfate dihydrate
3,6-diaminoacridine hemisulfate hemihydrate
dimidium bromide monohydrate
o-tolidine dihydrochloride hydrate
3,3',5,5'-tetramethylbenzidine dihydrochloride hydrate
3,3'-diaminobenzidine tetrahydrochloride dihydrate
3,6-[bis(4-amino-3-(sodiumsulphonato)phenylamino)]-2,5-dichloro 4-benzoquinone
2,2'-dimethylbenzidine hydrochloride
2,2'-(phenylmethylenebis)bis(4-methylaniline)
3,4'-diaminobiphenyl
2,7-diamino-9-fluorenone
n,n'-bis(2-aminophenyl)oxamide
2-[2-(2-aminophenyl)diaz-1-enyl]aniline
3,5,3',5'-tetrabromo-biphenyl-4,4'-diamine
n,n'-bis(4-aminophenyl)-1,3-bis(aminomethyl)benzene dihydrochloride
4',4"(5")-diaminodibenzo-15-crown-5
2,2'-bis(trifluoromethyl)benzidine
bis(4-amino-2,3-dichlorophenyl)methane
alpha,alpha'-bis(4-aminophenyl)-1,4-diisopropylbenzene
2,2-bis(3-aminophenyl)hexafluoropropane
3,10-diamino-6,13-dichlorobenzo[5,6][1,4]oxazino[2,3-b]phenoxazine-4,11-dis ulfo
n1-(2-amino-4-methylphenyl)-2-aminobenzamide
n1-(2-amino-4-chlorophenyl)-2-aminobenzamide
2,2'-dichloro[1,1'-biphenyl]-4,4'-diamine
4,4'(5')-diaminodibenzo-15-crown-5 dihydrochloride
rcl s19, 413-1
bis-(4-amino-3-nitro-phenyl)-methanone
bis-(3-amino-4-chloro-phenyl)-methanone
bis-(3-amino-4-dimethylamino-phenyl)-methanone
n,n'-bis-(4-amino-2-chloro-phenyl)-isophthalamide
n,n'-bis-(4-amino-2-chloro-phenyl)-terephthalamide
3,9-diamino-1,11-dimethyl-5,7-dihydro-dibenzo(a,c)cyclo-hepten-6-one
2-aminobenzaldehyde n-[(z)-(2-aminophenyl)methylidene]hydrazone
3,3'-bis(trifluoromethyl)benzidine
dicarboxidine 2 hcl
4,4'-(1,3-phenylenediisopropylidene)bisaniline
1,4-phenylenebis[[4-(4-aminophenoxy)phenyl]methanone]
2-((5-[(2-aminophenyl)thio]-3,4-dinitro-2-thienyl)thio)aniline
n'1-(2-aminobenzoyl)-2-aminobenzene-1-carbohydrazide
2-[4-(5-amino-1h-benzimidazol-2-yl)phenyl]-1h-benzimidazol-5-amine
4-[4-(4-aminophenoxy)-2,3,5,6-tetrafluorophenoxy]aniline
3,3'-dinitro-4,4'-diaminodiphenyl sulfone
3,3',4,4'-tetraaminodiphenylsulfone
4-[1-(4-aminophenyl)-1-methylethyl]aniline
3,3-diamino diphenyl urea
bis(4-aminophenyl)acetylene
dibenzo(1,2)dithiine-3,8-diamine
ethidium homodimer-2
4,4'-bis-(2-aminobenzenesulfonyl)bis-phenolester
neopentyl glycol bis(4-aminophenyl)ether
2,2'-oxydianiline
4,4'-diaminodiphenylamine-2,2-disulphonic acid
4,4-diamino diphenyl urea
3,3'-tolidine-5-sulfonic acid
n1-(3-[(2-aminobenzoyl)amino]propyl)-2-aminobenzamide
2-((6-[(2-aminophenyl)sulfanyl]-5-nitro-2-pyridyl)sulfanyl)aniline
2-((6-[amino-1,3-benzothiazol-2-yl)dithio)-1,3-benzothiazol-6-ylamine
tetramethylbenzidine
2-([6-[(2-aminophenyl)sulfanyl]-3,5-di(trifluoromethyl)-2-pyridyl]sulfanyl)anil
3,6-diaminothioxanthene-10-dioxide dihydrochloride
m-tolidine dihydrochloride hydrate
2-amino-n-[2-amino-4-(trifluoromethyl)phenyl]-5-methyl-benzamide
2-([2-[(2-aminophenyl)thio]-6-nitro-4-(trifluoromethyl)phenyl]thio)aniline
2-[(3-([(2-aminophenyl)thio]methyl)-2,4,6-trimethylbenzyl)thio]aniline
3-[3-amino-5-(trifluoromethyl)benzyl]-5-(trifluoromethyl)aniline
2-((5-[(2-aminophenyl)thio]-4-chloro-2-nitrophenyl)thio)aniline
4-(1-(4-aminophenyl)-2-[4-(dimethylamino)phenyl]vinyl)aniline
1,5-bis(4-aminophenoxy)pentane
2,3'-dichlorobenzidine dihydrochloride
3,3'-diamono-4,4'-dichlorodiphenyl sulfone
3-(bis-(4-amino-phenyl)-methyl)-2,3-dihydro-isoindol-1-one
4,4-diamino diphenyl-2-sulphonic acid 4,4'-diamino-diphenylene-cycylohexane
4,5'-diamino-(1,1')bianthracenyl-9,10,9',10'-tetraone
Alicyclic Diamines
4,4'-methylenebis(cyclohexylamine)
4,4'-methylenebis(2-methylcyclohexylamine)
Aliphatic Diamines
1,8-diamino-p-menthane
4,4'-methylenebis(cyclohexylamine)
d-cystine
l-cystine dimethyl ester dihydrochloride
neamine
bis(2-aminopropyl)amine
(h-cys-beta-na)2 2 hcl
l-cystine dibenzyl ester ditosylate
1,4-diaminocyclohexane
(h-cys-pna)2
dl-2-aminopropionic anhydride
l-cystine(di-b-naphthylamide)hydrochloride
l-cystine-bis-p-nitroanilide dihydrobromide
l-cystine diethyl ester dihydrochloride
trans-1,4-cyclohexanediamine
4,4'-methylenebis(2-methylcyclohexylamine)
l-leucinethiol, oxidized dihydrochloride
1,3-diaminoadamantane dihydrochloride
l-leucinethiol disulfide 2 hcl
l-cystine disodium salt, monohydrate
l-homocystine methylester hydrochloride
1,3-adamantanediamine
tetracyclo[8.2.1.1(8,11).0(2,7)]tetradeca-2,4,6-triene-10,11-diamine
tricyclo[3.3.1.0(3,7)]nonane-3,7-diamine From the class of commercially available diamines (L) preferred are the below listed ones:
Alicyclic Diamines
4,4'-methylenebis(cyclohexylamine)
4,4'-methylenebis(2-methylcyclohexylamine)
Aliphatic Diamines
4,4'-methylenebis(cyclohexylamine)
1,4-diaminocyclohexane
trans-1,4-cyclohexanediamine
4,4'-methylenebis(2-methylcyclohexylamine)
1,3-adamantanediamine
Aromatic Diamines
2,7-diaminofluorene
2,6-diaminoanthraquinone
4,4'-diaminooctafluorobiphenyl
4,4'-diaminodiphenyl ether
4,4'-dithiodianiline
4,4'-diaminodiphenylmethane
4,4'-ethylenedianiline
3,3'-dimethoxybenzidine
o-tolidine
3,3'-diaminobenzophenone
3,3'-diaminodiphenylmethane
3,4'-diaminodiphenylmethane
2,2-bis[4-(4-aminophenoxy)phenyl]hexafluoropropane
4-[3-(4-aminophenoxy)propoxy]aniline
4,4'-diaminodiphenyl sulfide
4,4'-diaminobenzophenone
2,2-bis(4-aminophenyl)hexafluoropropane
4,4'-bis(4-aminophenoxy)biphenyl
2,2-bis[4-(4-aminophenoxy)phenyl]propane
1,4-bis(4-aminophenoxy)benzene
1,3-bis(4-aminophenoxy)benzene
bis[4-(4-aminophenoxy)phenyl]sulfone
9,9-bis(4-aminophenyl)fluorene
benzidine
4,4'-azodianiline
1,3-bis(3-aminophenoxy)benzene
4,4'-diamino-1,1'-binaphthyl
4,4''-diamino-p-terphenyl
bis(p-aminophenoxy)dimethylsilane
4-[4-(4-aminophenoxy)butoxy]aniline
3,4'-diaminochalcone
trimethylene bis(4-aminobenzoate)
3,4'-diaminobiphenyl
2,7-diamino-9-fluorenone
4',4''(5'')-diaminodibenzo-15-crown-5
2,2'-bis(trifluoromethyl)benzidine
alpha,alpha'-bis(4-aminophenyl)-1,4-diisopropylbenzene
3,3'-bis(trifluoromethyl)benzidine
4,4'-(1,3-phenylenediisopropylidene)bisaniline
1,4-phenylenebis[[4-(4-aminophenoxy)phenyl]methanone]
4-[4-(4-aminophenoxy)-2,3,5,6-tetrafluorophenoxy]aniline
4-[1-(4-aminophenyl)-1-methylethyl]aniline
neopentyl glycol bis(4-aminophenyl)ether
4,4-diamino diphenyl ur
1,5-bis(4-aminophenoxy)pentane From the class of commercially available diamines (L) more preferred are the below listed ones:
Aromatic Diamines
2,7-diaminofluorene
4,4'-diaminooctafluorobiphenyl
4,4'-diaminodiphenyl ether
4,4'-diaminodiphenylmethane
4,4'-ethylenedianiline
3,3'-diaminobenzophenone
4-[3-(4-aminophenoxy)propoxy]aniline
4,4'-diaminodiphenyl sulfide
4,4'-diaminobenzophenone
2,2-bis(4-aminophenyl)hexafluoropropane
4,4'-bis(4-aminophenoxy)biphenyl
2,2-bis[4-(4-aminophenoxy)phenyl]propane
1,4-bis(4-aminophenoxy)benzene
1,3-bis(4-aminophenoxy)benzene
9,9-bis(4-aminophenyl)fluorene
benzidine
bis(p-aminophenoxy)dimethylsilane
4-[4-(4-aminophenoxy)butoxy]aniline
3,4'-diaminochalcone
trimethylene bis(4-aminobenzoate)
3,4'-diaminobiphenyl
2,7-diamino-9-fluorenone
4',4''(5'')-diaminodibenzo-15-crown-5
4-[4-(4-aminophenoxy)-2,3,5,6-tetrafluorophenoxy]aniline
4-[1-(4-aminophenyl)-1-methylethyl]aniline
1,5-bis(4-aminophenoxy)pentane
Aliphatic Diamines
4,4'-methylenebis(cyclohexylamine)
1,4-diaminocyclohexane
Alicyclic Diamines
4,4'-methylenebis(cyclohexylamine)

A further embodiment of the present invention is a composition comprising at least one diamine (I) and optionally at least one further diamine, which is different from (I) or/and an additive.

Preferably, the further diamine is of formula (L).

Additives such as silane-containing compounds and epoxy-containing crosslinking agents may be added.

Suitable silane-containing additives are described in Plast. Eng. 36 (1996), (Polyimides, fundamentals and applications), Marcel Dekker, Inc.

Suitable epoxy-containing cross-linking additives include 4,4'-methylene-bis-(N,N-diglycidylaniline), trimethylolpropane triglycidyl ether, benzene-1,2,4,5-tetracarboxylic acid 1,2,4,5-N,N'-diglycidyldiimide, polyethylene glycol diglycidyl ether, N,N-diglycidylcyclohexylamine and the like.

Additional additives are photo-sensitizers, photo-radical generators, cationic photo-initiators.

Suitable photo-active additives include 2,2-dimethoxyphenylethanone, a mixture of diphenylmethanone and N,N-dimethylbenzenamine or ethyl 4-(dimethylamino)-benzoate, xanthone, thioxanthone, Irgacure® 184, 369, 500, 651 and 907 (Ciba), Michler's ketone, triaryl sulfonium salt and the like.

Further the present invention relates to a process for the preparation of a diamine compound (XII) as defined above comprising contacting a compound of formula (XIV)

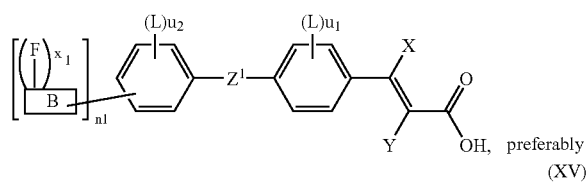

(XIV)

preferably

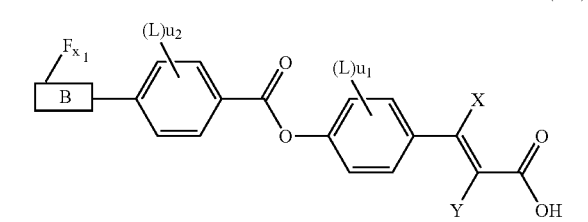

(XV)

with a dinitro compound of formula (XVI)

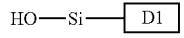

(XVI)

and then converting the obtained dinitro compound of formula (XVIa)

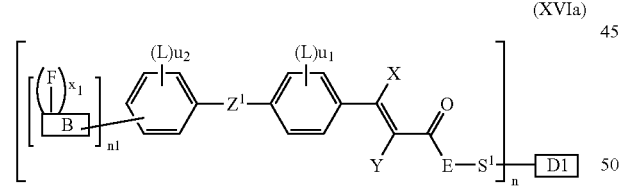

(XVIa)

in the corresponding diamino compound of formula (XII)

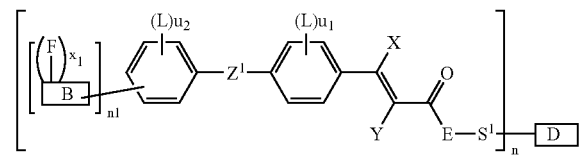

wherein F, $x_1$, $n_1$, n, B, D, X, Y, $Z^1$, L, $u_1$, $u_2$ and $S^1$ have the same meanings and preferences as given above, and wherein D1 has the same meaning and preferences as D as given above, with the proviso that the two amino groups of D are replaced by two nitro groups.

The reaction between compounds (XIV) and (XVI) can be conducted in many known ways (see J. March, Advanced Organic Chemistry, second edition, pages 363 and 365).

Usually, compounds (XIV) and (XVI) are contacted with a dehydrating agent.

Commonly known dehydrating agents can be used. Preferred are EDC, 1-(3-dimethylaminopropyl)-3-ethylcarbodiimide hydrochloride or DCC, dicyclohexylcarbodiimide, trifluoroacetic anhydride, $H_3BO_3$—$H_2SO_4$, polymer-protected $AlCl_3$, pyridinium salts-$Bu_3N$ or N,N-carbonyldiimidazole.

In general, the reaction of compounds (XIV) and (XVI) is conducted in a solvent.

Usually organic solvents, such as for example toluene, xylene, pyridine, halogenalkane, such as dichlormethan, trichlorethan, acetone or dimethylformamide are used.

The conversion of nitro compounds to amino compounds is commonly known and for example described J. March, Advanced Organic Chemistry, 1977, pages 1125 and 1126). Further, the conversion can be conducted in analogy to the process described in WO 98/13331 and WO 96/36597.

Further, the present invention relates to compounds of formulae (XIV) and (XVI), and (XVIa) as given above.

In addition, the present invention relates to polymer, copolymer and oligomer comprising diamine (I) as one of the basic building blocks.

Preferred polymer, copolymer and oligomer comprise diamine (I) and a tetracarboxylic acid anhydride as basic building blocks.

Preferably, the polymer, copolymer or oligomer is comprising diamine (I) as one basic building block are in the context of the invention a polyamic acid, polyamic ester, polyimide or a mixture thereof, preferably a mixture of polyamic acid and polyamic ester and/or polyimide. More preferred is a mixture of polyamic acid and polyimide.

In the context of the present invention the term "polyimide" has the meaning of partially or complete imidisated polyamic acid or polyamic ester. In analogy, the term "imidisation" has in the context of the present invention the meaning of partially or complete imidisation.

Preferably, the tetracarboxylic acid anhydride is of formula (V)

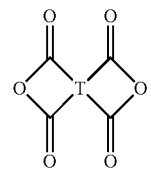

(V)

wherein:
T represents a tetravalent organic radical.

The tetravalent organic radical T is preferably derived from an aliphatic, alicyclic or aromatic tetracarboxylic acid dianhydride.

Preferred examples of aliphatic or alicyclic tetracarboxylic acid dianhydrides are:
1,1,4,4-butanetetracarboxylic acid dianhydride,
ethylenemaleic acid dianhydride,
1,2,3,4-cyclobutanetetracarboxylic acid dianhydride,
1,2,3,4-cyclopentanetetracarboxylic acid dianhydride,
2,3,5-tricarboxycyclopentylacetic acid dianhydride,
3,5,6-tricarboxynorbornylacetic acid dianhydride,
2,3,4,5-tetrahydrofurantetracarboxylic acid dianhydride, rel-[1S,5R,6R]-3-oxabicyclo[3.2.1]octane-2,4-dione-6-spiro-3'-(tetrahydrofuran2',5'-dione),
4-(2,5-dioxotetrahydrofuran-3-yl)tetrahydronaphthalene-1,2-dicarboxylicacid dianhydride,
5-(2,5-dioxotetrahydrofuran-3-yl)-3-methyl-3-cyclohexene-1,2-dicarboxylicacid dianhydride,
bicyclo[2.2.2]oct-7-ene-2,3,5,6-tetracarboxylic acid dianhydride,
bicyclo[2.2.2]octane-2,3,5,6-tetracarboxylic acid dianhydride,
1,8-dimethylbicyclo[2.2.2]oct-7-ene-2,3,5,6-tetracarboxylic acid dianhydride, pyromellitic acid dianhydride,
3,3',4,4'-benzophenonetetracarboxylic acid dianhydride,
4,4'-oxydiphthalic acid dianhydride,
3,3',4,4'-diphenylsulfonetetracarboxylic acid dianhydride,
1,4,5,8-naphthalenetetracarboxylic acid dianhydride,
2,3,6,7-naphthalenetetracarboxylic acid dianhydride,
3,3',4,4'-dimethyldiphenylsilanetetracarboxylic acid dianhydride,
3,3',4,4'-tetraphenylsilanetetracarboxylic acid dianhydride,
1,2,3,4-furantetracarboxylic acid dianhydride,
4,4'-bis(3,4-dicarboxyphenoxy)diphenyl sulfide dianhydride,
4,4'-bis(3,4-dicarboxyphenoxy)diphenyl sulfone dianhydride,
4,4'-bis(3,4-dicarboxyphenoxy)diphenylpropane dianhydride,
3,3',4,4'-biphenyltetracarboxylic acid dianhydride,
ethylene glycol bis(trimellitic acid) dianhydride,
4,4'-(1,4-phenylene)bis(phthalic acid) dianhydride,
4,4'-(1,3-phenylene)bis(phthalic acid) dianhydride,
4,4'-(hexafluoroisopropylidene)diphthalic acid dianhydride,
4,4'-oxydi(1,4-phenylene)bis(phthalic acid) dianhydride, and
4,4'-methylenedi(1,4-phenylene)bis(phthalic acid) dianhydride.

Preferred examples of aromatic tetracarboxylic acid dianhydrides are:
pyromellitic acid dianhydride,
3,3',4,4'-benzophenonetetracarboxylic acid dianhydride,
4,4'-oxydiphthalic acid dianhydride,
3,3',4,4'-diphenylsulfonetetracarboxylic acid dianhydride,
1,4,5,8-naphthalenetetracarboxylic acid dianhydride,
2,3,6,7-naphthalenetetracarboxylic acid dianhydride,
3,3',4,4'-dimethyldiphenylsilanetetracarboxylic acid dianhydride,
3,3',4,4'-tetraphenylsilanetetracarboxylic acid dianhydride,
1,2,3,4-furantetracarboxylic acid dianhydride,
4,4'-bis(3,4-dicarboxyphenoxy)diphenyl sulfide dianhydride,
4,4'-bis(3,4-dicarboxyphenoxy)diphenyl sulfone dianhydride,
4,4'-bis(3,4-dicarboxyphenoxy)diphenylpropane dianhydride,
3,3',4,4'-biphenyltetracarboxylic acid dianhydride,
ethylene glycol bis(trimellitic acid) dianhydride,
4,4'-(1,4-phenylene)bis(phthalic acid) dianhydride,
4,4'-(1,3-phenylene)bis(phthalic acid) dianhydride,
4,4'-(hexafluoroisopropylidene)diphthalic acid dianhydride,
4,4'-oxydi(1,4-phenylene)bis(phthalic acid) dianhydride,
4,4'-methylenedi(1,4-phenylene)bis(phthalic acid) dianhydride,
and the like.

More preferably the tetracarboxylic acid dianhydrides used to form the tetravalent organic radical T are selected from:
1,2,3,4-cyclobutanetetracarboxylic acid dianhydride,
1,2,3,4-cyclopentanetetracarboxylic acid dianhydride,
2,3,5-tricarboxycyclopentylacetic acid dianhydride,
5-(2,5-dioxotetrahydrofuran-3-yl)-3-methyl-3-cyclohexene-1,2-dicarboxylic acid dianhydride,
4-(2,5-dioxotetrahydrofuran-3-yl)tetrahydronaphthalene-1,2-dicarboxylic acid dianhydride,
4,4'-(hexafluoroisopropylidene)diphthalic acid dianhydride and bicyclo[2.2.2]oct-7-ene-2,3,5,6-tetracarboxylic acid dianhydride.

The polymer, copolymer or oligomer, especially the polyamic acid, polyamic acid ester and polyimide and mixtures thereof may be prepared in line with known methods, such as those described in Plast. Eng. 36 (1996), (Polyimides, fundamentals and applications), Marcel Dekker, Inc.

For example, the amidisation, poly-condensation reaction for the preparation of the polyamic acids is carried out in solution in a polar aprotic organic solvent, such as γ-butyrolactone, N,N-dimethylacetamide, N-methylpyrrolidone or N,N-dimethyl-formamide. In most cases equimolar amounts of the anhydride and the diamine are used, i.e. one amino group per anhydride group. If it is desired to stabilize the molecular weight of the polymer, copolymer or oligomer, it is possible for that purpose to either add an excess or a less-than-stoichiometric amount of one of the two components or to add a mono-functional compound in the form of a dicarboxylic acid monoanhydride or in the form of a monoamine. Examples of such mono-functional compounds are maleic acid anhydride, phthalic acid anhydride, aniline and the like. Preferably the reaction is carried out at temperatures of less than 100° C.

The imidisation, cyclisation of the polyamic acids to form the polyimides can be carried out by heating, i.e. by condensation with removal of water or by other imidisation reactions using appropriate reagents.

Partially imidisation is achieved for example, if the imidisation is carried out purely thermally, the imidisation of the polyamic acids may not always be complete, i.e. the resulting polyimides may still contain proportions of polyamic acid.

Complete imidisation reactions are carried out at temperatures between 60 and 250° C., preferably at temperatures of less than 200° C.

In order to achieve imidisation at lower temperatures additional reagents that facilitate the removal of water are added to the reaction mixture. Such reagents are, for example, mixtures consisting of acid anhydrides, such as acetic acid anhydride, propionic acid anhydride, phthalic acid anhydride, trifluoroacetic acid anhydride or tertiary amines, such as triethylamine, trimethylamine, tributylamine, pyridine, N,N-dimethylaniline, lutidine, collidine etc. The amount of aforementioned additional reagents that facilitate the removal of water is preferably at least four equivalents of acid anhydride and two equivalents of amine per equivalent of polyamic acid to be condensed.

The imidization degree of each polymer used in the liquid crystal alignment agent of the invention can be arbitrarily adjusted by controlling the catalyst amount, reaction time and reaction temperature employed in production of the polymer. In the present description, "imidization degree" of polymer refers to a proportion (expressed in %) of the number of recurring units of polymer forming an imide ring or an isoimide ring to the number of total recurring units of polymer. In the present description, the imidization degree of a polyamic acid not subjected to dehydration and ring closure is 0%. The imidization degree of each polymer is determined by dissolving the polymer in deuterated dimethyl sulfoxide, subjecting the resulting solution to $^1$H-NMR measurement at a room temperature using tetramethylsilane as a standard substance, and calculating from the following formula.

Imidization degree(%)=1−($A^1$/$A^2$×$B$)×100

$A^1$: Peak area based on protons of NH groups (in the vicinity of 10 ppm)
$A^2$: Peak area based of one proton of acrylate double bond (in the vicinity of 6.5 ppm).
B: Proportion of the number of acrylate protons to one proton of NH group in the polymer precursor The imidization degree is usually in the range of 1 to 99%, preferably 5 to 50%, more preferably 10 to 40%.

The present invention concerns a process for the preparation of a polymer, copolymer or oligomer comprising polymerisation of a diamine (I).

Preferably the polymerisation of a diamine (I) comprises
    a) amidisation of at least one diamine (I) to polyamic acid or a polyamic ester, and
    b) imidisation of the obtained polyamic acid or ester, to a polyimide, or
    c) imidisation of the diamine (I) to polyimide.

In a more preferred embodiment of the invention, the polymersiation of the diamine comprises the amidsation of at least one diamine (I) with tetracarboxylic acid anhydride, preferably tetracarboxylic acid anhydride (V), and/or the imidisation, preferably by elevated temperature.

In a further more preferred embodiment of the invention, the polymersiation of the diamine comprises the amidsation of a diamine (I) with tetracarboxylic acid anhydride, preferably tetracarboxylic acid anhydride (V), and/or the imidisation, preferably by elevated temperature, and wherein the amidisation and/or imidisation is optionally conducted
    in the presence of additives as given above, and/or
    in the presence of a further diamine, which is different from that of formula (I), preferably in the presence of at least one diamine (L) and/or
    in the presence of a further polymer, copolymer or oligomer comprising as one basic building block a diamine (L), or a further polymer, copolymer or oligomer, which is different from a polyamic acid, polyamic ester or a polyimide, more preferably a further polymer, copolymer or oligomer, which is selected from the group of which is selected from the group of polymers include polyacrylates, polymethacrylates, polyacrylamides, polymethacrylamides, polyvinylether and polyvinylester, polyallylether and ester, polystyrenes, polysiloxanes, polyimides, polyamic acids and their esters, polyamidimides, polymaleic acids, polyfumaric acids polyurethanes and derivatives thereof.

Preferably, the further polymer, copolymer or oligomer comprises as basic building block a diamine (L) and a tetracarboxylic acid anhydride, preferably a tetracarboxylic acid anhydride of formula (V).

This polymer, copolymer or oligomer is prepared in analogy to the polymer, copolymer or oligomer of the invention comprising diamine (I).

The imidation is conducted after or during amidisation. In general, the imidisation is conducted after amidisation.

Preferred is the partially imidisation of polyamic acid or polyamic ester.

If the polymer is prepared only by imidisation, diamine (I) will be contacted with an imidisation compound, with at least two polymerisable functional groups, such as for example, carbonyl groups or halogen groups.

More preferably, the present invention concerns a process for the preparation of a polymer, copolymer or oligomer comprising polymerisation of a diamine (I) and tetracarboxylic acid anhydride, preferably tetracarboxylic acid anhydride (V).

Another embodiment of the present invention relates to a copolymer comprising diamine (I). Preferred is a copolymer, comprising at least two diamines (I).

A further embodiment of the present invention relates to a polymer, copolymer or oligomer, or to blends obtainable according to the processes and preferred processes of the invention.

Preferably, blends are obtainable by reaction of at least two different diamine (I), or by reaction of at least one diamine (I) with a polymer, copolymer or oligomer comprising as basic building block at least one diamine (L).

Preferably, the present invention concerns polymer, copolymer or oligomer, comprising in their polymer-, copolymer- or oligomer-side-chains at least one photo-reactive group. Preferably, the photo-reactive group of the side chains are photo-isomerized and/or crosslinked, more preferably photo-dimerized, by exposure to aligning light.

The term photoreactive groups has the meaning of groups, which are able to react by interaction with light.

The treatment with aligning light may be conducted in a single step or in several separate steps. In a preferred embodiment of the invention the treatment with aligning light is conducted in a single step.

In the context of the present invention photo-reactive group has preferably the meaning of a dimerizable, isomerizable, polymerizable and/or cross-linkable group.

In the context of the present invention, aligning light is light of wavelengths, which can initiate photoalignment. Preferably, the wavelengths are in the UV-A, UVB and/or UV/C-range, or in the visible range. It depends on the photoalignment compound, which wavelengths are appropriate. Preferably, the photo-reactive groups are sensitive to visible and/or UV light. A further embodiment of the invention concerns the generating of aligning light by laser light.

The instant direction of the aligning light may be normal to the substrate or at any oblique angle.

For generating tilt angles, preferably the aligning light is exposed from oblique angles.

More preferably, aligning light is at least partially linearly polarized, elliptically polarized, such as for example circulary polarized, or non-polarized; most preferably at least circulary or partially linearly polarized light, or non-polarized light exposed obliquely. Especially, most preferred aligning light denotes substantially polarised light, especially linearly polarised light; or aligning light denotes non-polarised light, which is applied by an oblique irradiation.

In a more preferred embodiment of the invention the polymer, copolymer or oligomer is treated with polarised light, especially linearly polarised light, or by oblique radiation with non-polarised light.

Further preferred are polymers, copolymers or oligomers of the present invention,
    wherein at least 30%, preferably at least 75% of the repeating units include a side chain with a photo-reactive group; and/or
    wherein, the photo-reactive groups are able to undergo photo-dimerisation, preferably photo-cyclisation, in particular [2+2]-photo-cyclisation; and/or
    wherein the polymer or oligomer is a polymer gel or a polymer network, or an oligomer gel or an oligomer network, respectively; and/or wherein the polymer, copolymer or oligomer has an intrinsic viscosity in the range of 0.05 to 10 dL/g, preferably in the range of 0.05 to 5 dL/g; and/or wherein the polymer, copolymer or oligomer contains from 2 to 2000 repeating units, especially from 3 to 200 repeating units; and/or wherein the polymer, copolymer or oligomer is in the form of a homopolymer or of a copolymer, preferably of a statistical copolymer; and/or wherein the polymer, copolymer or oligomer is cross-linkable or cross-linked;

A further preferred embodiment of the present invention concerns polymers, copolymers or oligomers, having an intrinsic viscosity preferably in the range of 0.05 to 10 dL/g, more preferably in the range of 0.05 to 5 dL/g. Herein, the intrinsic viscosity ($\eta_{inh}=\ln \eta_{rel}/C$) is determined by measuring a solution containing a polymer or an oligomer in a concentration of 0.5 g/100 ml solution for the evaluation of its viscosity at 30° C. using N-methyl-2-pyrrolidone as solvent.

In addition, a preferred embodiment of the present invention concerns polymers, copolymers or oligomers, containing from 2 to 2000 repeating units, especially from 3 to 200 repeating units.

The side-chain polymers or oligomers according the invention can be present in the form of homopolymers as well as in the form of copolymers. The term "copolymers" is to be understood as meaning especially statistical copolymers.

Further, the present invention concerns a composition, especially a blend, comprising a polymer, copolymer or oligomer according to definition and preferences of the invention, comprising at least a diamine (I) as basic building block, or a polymer, copolymer or oligomer according to definition and preferences of the invention, obtainable by the processes of the invention, and preferably in addition comprising and a further diamine, which is different from diamine (I), preferably a diamine (L).

The further polymer, copolymer or oligomer comprising as one basic building block a diamine (L) has the same preferences as given above.

Preferably, the present invention concerns a composition, especially a blend, comprising a polymer, copolymer or oligomer according to definition and preferences of the invention, comprising at least a diamine (I) as basic building block, or a polymer, copolymer or oligomer according to definition and preferences of the invention, obtainable by the processes of the invention, and/or a further polymer, copolymer or oligomer comprising as one basic building block a further diamine, which is different from diamine (I), preferably a diamine (L), or a further polymer, copolymer or oligomer, which is different from a polyamic acid, polyamic ester or a polyimide, more preferably a further polymer, copolymer or oligomer, which is selected from the group of polyacrylate, polystyrol, polyester, polyurethane, polyethylene, poylpopylen, polyvinylchloride, polytetrafluoroethylen, polycabonate, polyterephthalate and dendrimere.

Further preferably, the present invention concerns a composition, especially a blend, comprising a polymer, copolymer or oligomer according to definition and preferences of the invention, comprising at least a diamine (I) as basic building block, or a polymer, copolymer or oligomer according to definition and preferences of the invention, obtainable by the processes of the invention, and optionally a further diamine, which is different from diamine (I), preferably a diamine (L), and an additive, preferably silane-containing compounds, and/or a further polymer, copolymer or oligomer comprising as one basic building block a further diamine, which is different from diamine (I), preferably at least one diamine (L), and/or a further polymer, copolymer or oligomer, which is different from a polyamic acid, polyamic ester or a polyimide, more preferably a further polymer, copolymer or oligomer, which is selected from the group of polymers include polyacrylates, polymethacrylates, polyacrylamides, polymethacrylamides, polyvinylether and polyvinylester, polyallylether and ester, polystyrenes, polysiloxanes, polyimides, polyamic acids and their esters, polyamidimides, polymaleic acids, polyfumaric acids polyurethanes and derivatives thereof, and/or photo-active polymers, photo-active oligomers and/or photo-active monomers, and/or cross-linking agents, preferably epoxy-containing cross-linking agents, most preferably selected from the group:

4,4'-methylene-bis-(N,N-diglycidylaniline), trimethylolpropane triglycidyl ether, benzene-1,2,4,5-tetracarboxylic acid 1,2,4,5-N,N'-diglycidyldiimide, polyethylene glycol diglycidyl ether, N,N-diglycidylcyclohexylamine.

The polymers or oligomers according to the invention may be used in form of polymer layers or oligomer layers alone or in combination with other polymers, oligomers, monomers, photo-active polymers, photo-active oligomers and/or photo-active monomers, depending upon the application to which the polymer or oligomer layer is to be added. Therefore it is understood that by varying the composition of the polymer or oligomer layer it is possible to control specific and desired properties, such as an induced pre-tilt angle, good surface wetting, a high voltage holding ratio, a specific anchoring energy, etc.

Polymer or oligomer layers may readily be prepared from the polymers or oligomers of the present invention and a further embodiment of the invention relates to a polymer or oligomer layer comprising a polymer or oligomer according to the present invention, which is preferably prepared by treatment with aligning light. Preferably, the invention relates to a polymer or oligomer layer comprising a polymer or oligomer according to the present invention in a cross-linked and/or isomerized form.

The polymer or oligomer layer is preferably prepared by applying one or more polymers or oligomers according to the invention to a support and, after imidisation or without imidisation, treating, preferably cross-linking and/or isomerising, the polymer or oligomer or polymer mixture or oligomer mixture by irradiation with aligning light.

In general, transparent support such as glass or plastic substrates, optionally coated with indium tin oxide (ITO) are used.

Further, it is possible to vary the direction of orientation and the tilt angle within the polymer or oligomer layer by controlling the direction of the irradiation of the aligning light. It is understood that by selectively irradiating specific regions of the polymer or oligomer layer very specific regions of the layer can be aligned. In this way, layers with a defined tilt angle can be provided. The induced orientation and tilt angle are retained in the polymer or oligomer layer by the process, especially by the process of cross-linking.

Method for the preparation of a polymer, copolymer or oligomer according to the invention, wherein in a polycondensation reaction a diamine (I) is reacted with one or more tetracarboxylic acid anhydrides of the general formula (V), optionally in the presence of one or more additional other diamines.

Further, the present invention preferably concerns a method, wherein a polycondensation reaction for the preparation of the polyamic acids is carried out in solution in a polar aprotic organic solvent, preferably selected from γ-butyrolactone, N,N-dimethylacetamide, N-methylpyrrolidone or N,N-dimethylformamide.

Preferably, the present invention concerns a method, wherein subsequent to the polycondensation cyclisation with removal of water is carried out thermally under formation of a polyimide.

More preferably, the present invention concerns a method, wherein imidisation is carried out prior or after the application of the polymer, copolymer or oligomer to a support.

Further preferred methods of the invention relates to
a method for the preparation of a polymer layer or oligomer layer, which are vertically aligned;
a method for the preparation of multi-domain vertical alignment of a polymer layer or oligomer layer;
a method for the preparation of a polymer layer or oligomer layer with tilted optical axis.

A further embodiment of the present invention concerns a polymer, copolymer or oligomer layer, in particular orientation layer, comprising at least one polymer, copolymer or oligomer according to the present invention.

It is understood that the polymer or oligomer layers of the present invention (in form of a polymer gel, a polymer network, a polymer film, etc.) can also be used as orientation layers for liquid crystals. A further preferred embodiment of the invention relates to an orientation layer comprising one or more polymers or oligomers according to the invention, preferably in a cross-linked form. Such orientation layers can be used in the manufacture of unstructured or structured optical- or electro-optical elements, preferably in the production of hybrid layer elements.

In addition, the present invention concerns a method for the preparation of a polymer layer or oligomer layer, wherein one or more polymers, copolymers or oligomers according to the present invention is applied to a support, preferably from a solution of the polymer or oligomer material and subsequent evaporation of the solvent, and wherein, after any imidisation step which may be necessary, the polymer or oligomer or polymer mixture or oligomer mixture treated with aligning light, and preferably isomerized and/or cross-linked by irradiation with aligning light.

A preferred method of the present invention concerns a method, wherein the direction of orientation and the tilt angle within the polymer layer or oligomer layer is varied by controlling the direction of the irradiation with aligning light, and/or wherein by selectively irradiating specific regions of the polymer layer or oligomer layer specific regions of the layer are aligned.

The orientation layers are suitably prepared from a solution of the polymer or oligomer material. The polymer or oligomer solution is applied to a support optionally coated with an electrode [for example a glass plate coated with indium-tin oxide (ITO)] so that homogeneous layers of 0.05 to 50 μm thickness are produced. In this process different coating techniques like spin-coating, meniscus-coating, wire-coating, slot-coating, offset-printing, flexo-printing, gravur-printing may be used. Then, or optionally after a prior imidisation step, the regions to be oriented are irradiated, for example, with a high-pressure mercury vapour lamp, a xenon lamp or a pulsed UV laser, using a polarizer and optionally a mask for creating images of structures.

Further, the present invention concerns the use of a polymer layer, copolymer or oligomer layer according to the present invention, preferably in cross-linked form, as an orientation layer for liquid crystals.

Further, the present invention concerns preferably the use of a polymer layer, copolymer or oligomer layer for the induction of vertical alignment of adjacent liquid crystalline layers, in particular for operating a cell in MVA mode.

The irradiation time is dependent upon the output of the individual lamps and can vary from a few seconds to several hours. The photo-reaction (dimerisation, polymersiation, cross-linking) can also be carried out, however, by irradiation of the homogeneous layer using filters that, for example, allow only the radiation suitable for the cross-linking reaction to pass through.

It is understood that the polymer or oligomer layers of the invention may be used in the production of optical or electro-optical devices having at least one orientation layer as well as unstructured and structured optical elements and multi-layer systems.

The present invention concerns the use of a polymer layer, copolymer or oligomer layer as an orientation layer for liquid crystals.

Preferred is the use for the induction of vertical alignment of adjacent liquid crystalline layers.

A further embodiment of the invention relates to an optical or electro-optical device comprising one or more polymers or oligomers according to the present invention in cross-linked form. The electro-optical devices may comprise more than one layer. The layer, or each of the layers may contain one or more regions of different spatial orientation.

Preferably, the present invention concerns an optical and electro-optical unstructured or structured constructional elements, preferably liquid crystal display cells, multi-layer and hybrid layer elements, comprising at least one polymer layer, copolymer or oligomer layer according to the present invention.

More preferably, the present invention concerns an orientation layer, comprising at least one polymer layer, copolymer or oligomer layer according to the present invention.

The advantages of the present invention could not be foreseen by a skilled person. It has surprisingly been found, that in addition to the polyamic/polyimide backbone, the introduction of an organofluorine group into a peripheral position of the polymer side groups having specific molecular architecture plays a predominant role in obtaining MVA materials having optimised properties, such as the required high voltage holding ratios, the adjustable pre-tilt angles required for the MVA mode and their stability to light and heat.

EXAMPLE 1

Synthesis

Preparation of (2E)-3-(4-{[4-(4,4,4-trifluorobutoxy)benzoyl]oxy}phenyl)acrylic acid

1.1 Preparation of 4-(4,4,4-trifluorobutoxy)benzoic acid

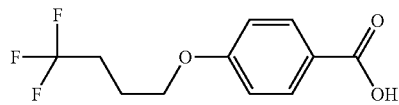

55.00 g (0.408 Mol) 4,4,4-trifluorobutan-1-ol arre dissolved in 550 ml tetrahydrofurane, 142 ml (0.102 Mol) triethylamine are added at room temperature 38 ml (0.490 Mol) methanesulfonyl chloride were added dropwise under nitrogen. The mixture is stirred for 1 h at 0-5° C. The beige suspension is Hyflo-filtrated and washed with tetrahydrofurane. The filtrate is concentrated. The residue is dissolved in 1.4 l 1-methyl-2-pyrrolidone 62.70 g (0.408 Mol) of methyl 4-hydroxybenzoate and 226.00 g (1.43 Mol) of potassium carbonate are added to the lightly brown solution. The reaction suspension is allowed to react at 80° C. for 14 h. 1 l (1.0 Mol) of a 1N NaOH solution is added to the above mixture. The suspension is heated at reflux temperature for 30 min until the reaction is completed. The reaction mixture is allowed to cool at room temperature and thrown in cold water. The solution is carefully acidified with a 25% HCl solution and is stirred for 15 min. The product is filtrated off, washed with water and dried overnight at room temperature under vacuum to give 99.00 g (98%) of 4-(4,4,4-trifluorobutoxy) benzoic acid as a white solid.

1.2 Preparation of 4-Formylphenyl-4-(4,4,4-trifluorobutoxy)benzoate

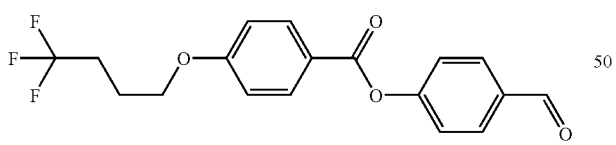

6.89 g (56.4 mmol) of 4-hydroxybenzaldehyd, 14.0 g (56.4 mmol) of 4-(4,4,4-trifluorobutoxy)benzoic acid, 0.69 g (5.6 mmol) of 4-Dimethylaminopyridine are dissolved in 100 ml of dichloromethane. 11.89 g (62.0 mmol) of N-(3-Dimethylaminopropyl)-N'-ethylcarbodiimide hydrochloride (EDC hydrochloride) are added at 0° C. The solution is stirred for 1 h at 0° C. and allowed to stir at room temperature overnight. After 22 hours at room temperature the reaction mixture was partitioned between dichloromethane and water; the organic phase is washed repeatedly with water, dried over sodium sulphate, filtered and concentrated by rotary evaporation. Crystallization form 2-propanol at 0° C. give 17.1 g 4-formylphenyl-4-(4,4,4-trifluorobutoxy)benzoate as colourless crystals.

1.3 Preparation of (2E)-3-(4-{[4-(4,4,4-trifluorobutoxy)benzoyl]oxy}phenyl)acrylic acid

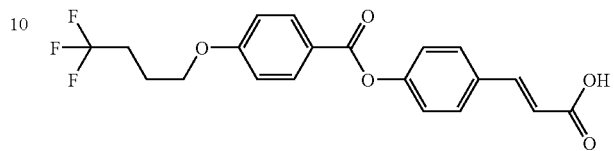

5.00 g (14.2 mMol) of 4-formylphenyl 4-(4,4,4-trifluorobutoxy)benzoate and 3.00 g (28.4 mMol) of Malonic acid are dissolved in 18 ml (227.1 mMol) of Pyridin. 1.21 g (14.2 mMol) of Piperidin are added to the suspension which is allowed to react at 100° C. under argon for 1.5 h. The yellow solution is then thrown on ice. The solution is carefully acidified to pH=1-2 with a 25% HCl solution and is stirred for 15 min. The product is filtrated off and dried at room temperature under vacuum for 10 h to give 5.2 g of (2E)-3-(4-{[4-(4,4,4-trifluorobutoxy)benzoyl]oxy}phenyl)acrylic acid as white powder.

(2E)3-{4-[(4-(4,4,5,5,5-pentafluoropentyloxy)benzoyl)oxy]phenyl}acrylic acid is prepared analogous to example 1 using 4,4,5,5,5-pentafluoropentan-1-ol instead of 4,4,4-trifluorobutan-1-ol.

The following acrylic acid are synthesized in an analogous manner:

(2E)3-{4-[(4-trifluoromethoxybenzoyl)oxy]phenyl}acrylic acid
(2E)3-{4-[(4-(2,2,2-trifluoroethoxy)benzoyl)oxy]phenyl}acrylic acid
(2E)3-{4-[(4-(2,2,2-trifluoropropoxy)benzoyl)oxy]phenyl}acrylic acid
(2E)3-{4-[(4-(5,5,5-trifluoropentyloxy)benzoyl)oxy]phenyl}acrylic acid
(2E)3-{4-[(4-(1,1,2,2-tetrafluoroethoxy)benzoyl)oxy]phenyl}acrylic acid
(2E)3-{4-[(4-(1,1,2,2-tetrafluoropropoxy)benzoyl)oxy]phenyl}acrylic acid
(2E)3-{4-[(4-(4,4,5,5,6,6,6-heptafluorohexyloxy)benzoyl)oxy]phenyl}acrylic acid

EXAMPLE 2

Synthesis

Preparation of 6-{[((2E)-3-{4-[(4-(4,4,4-trifluorobutoxy)benzoyl)oxy]phenyl}prop-2-enoyl)oxy]}hexyl 3,5-diaminobenzoate

2.1 Preparation of (2E)-3-{4-[(ethoxycarbonyl)oxy]phenyl}acrylic acid

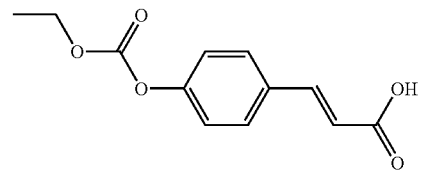

67 g (0.41 mol) p-cumaric acid are added to a mixture of 50.4 g (0.90 mol) potassium hydroxide and 600 ml water. 53.1 g (0.50 mol) ethyl chloroformate are added dropwise at 0° C. The reaction temperature rises to 10° C. The reaction mixture is subsequently allowed to react for 2 hours at 25° C. and acidified to pH=1 with 200 ml hydrochloric acid 7N. The product is filtered off, washed with water and dried under vacuum to give 95.3 g of (2E)-3-{4-[(ethoxycarbonyl)oxy]phenyl}acrylic acid as white powder.

2.2 Preparation of 6-hydroxyhexyl 3,5-dinitrobenzoate

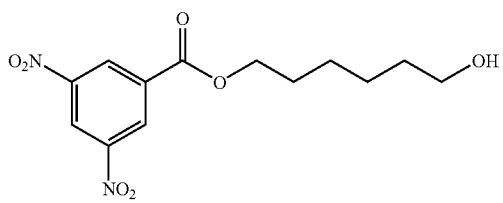

357.70 g (1.686 Mol) of 3,5-dinitrobenzoic acid are suspended in 750 ml of 1-methyl-2-pyrrolidone. The suspension is stirred up to 50° C. 386.36 g (4.599 Mol) of sodium hydrogen carbonate are added and the mixture was heated up to 90° C. 22.50 g (0.150 Mol) of sodium iodide and 204.0 ml (1.533 Mol) of 6-chlorohexanol are added to the reaction mixture which is heated to 100° C. for 1 h. After 1 h of reaction, the reaction is complete and the orange suspension is thrown on 2 l of ice and 1 l of water. The product is filtrated, washed water and dried at 50° C. under vacuum for 24 h to give 425.0 g (91%) of 6-hydroxyhexyl 3,5-dinitrobenzoate as a rose powder.

2.3 Preparation of 6-[((2E)-{4-[(ethoxycarbonyl)oxy]phenyl}prop-2-enoyl)oxy]hexyl 3,5-dinitrobenzoate

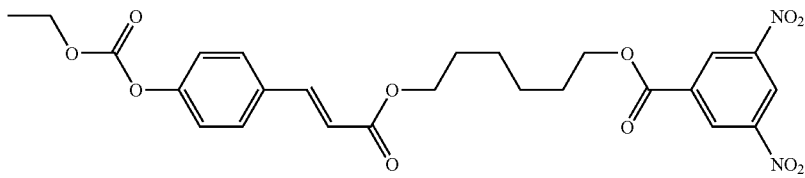

4.53 g (0.0145 Mol) of 6-hydroxyhexyl 3,5-dinitrobenzoate, 3.44 g (0.0145 Mol) of 4-ethylcarbonatecinnamic acid, 0.177 g (0.0015 Mol) of 4-Dimethylaminopyridine are dissolved in 40 ml of dichloromethane. 3.04 g (0.0159 Mol) of N-(3-Dimethylaminopropyl)-N'-ethylcarbodiimide hydrochloride (EDC hydrochloride) are added at 0° C. The solution is stirred for 1 h at 0° C. and allowed to stir at room temperature overnight. After 22 hours at room temperature the reaction mixture is partitioned between dichloromethane and water; the organic phase is washed repeatedly with water, dried over sodium sulphate, filtered and concentrated by rotary evaporation. The residue is dissolved ethyl acetate. The product is precipitated with Hexane at 0° C. The precipitated is filtrated and dried under vacuum overnight to give 4.2 g (55%) of 6-[((2E)-{4-[(ethoxycarbonyl)oxy]phenyl}prop-2-enoyl)oxy]hexyl 3,5-dinitrobenzoate as a light-yellow powder.

2.4 Preparation of 6-[((2E)-{4-hydroxyphenyl}prop-2-enoyl)oxy]hexyl 3,5-dinitrobenzoate

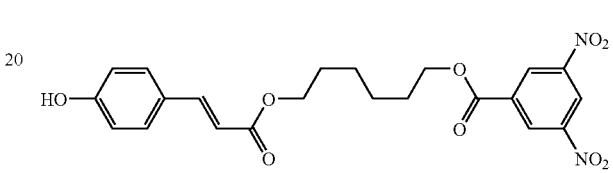

43.20 g (0.081 Mol) of 6-[((2E)-{4-[(ethoxycarbonyl)oxy]phenyl}prop-2-enoyl)oxy]hexyl 3,5-dinitrobenzoate are dissolved in 66 ml (0.815 Mol) of pyridine and 400 ml of acetone at room temperature. 61 ml (0.815 Mol) of ammonium hydroxide solution 25% are added dropwise to the solution at room temperature. After 12 h reaction, the mixture is thrown on water and acidified by the addition of HCl 25% (up to pH=3-4). A paste is obtained which is filtrated and dissolved in ethyl acetate and extracted with water. The organic phase is dried with sodium sulfate, filtered, concentrated by rotary evaporation. Filtration of the residue over silica gel with tert-Butyl methyl ether as eluant and crystallization of the residue in 200 ml of ethyl acetate and 1200 ml of hexane at 0° C. give 15.84 g of 6-[((2E)-{4-hydroxyphenyl}prop-2-enoyl)oxy]hexyl 3,5-dinitrobenzoate as yellow crystals.

2.5 Preparation of 6-{[((2E)-3-{4-[(4-(4,4,4-trifluorobutoxy)benzoyl)oxy]phenyl}prop-2-enoyl)oxy]}hexyl 3,5-dinitrobenzoate

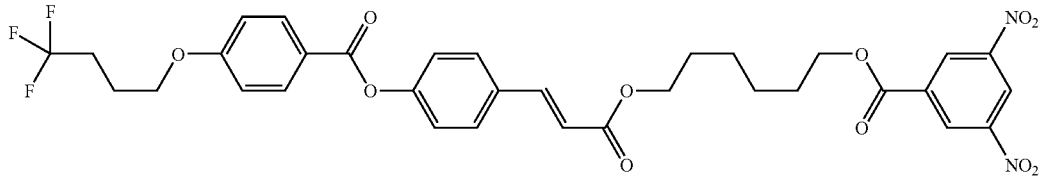

8.61 g (0.0347 Mol) of 4-(4,4,4-trifluorobutoxy)benzoic acid are suspended in 100 ml of dichloromethane. 0.42 g (0.0035 Mol) of 4-Dimethylaminopyridine are added at room temperature. 7.98 g (0.04163 Mol) of N-(3-Dimethylaminopropyl)-N'-ethylcarbodiimide hydrochloride (EDC hydrochloride) are added at 0° C. The solution is stirred for 1 h at 0° C. 15.90 g (0.0347 Mol) of 6-[((2E)-{4-hydroxyphenyl}prop-2-enoyl)oxy]hexyl 3,5-dinitrobenzoate dissolved in 50 ml of dichloromethane are added dropwise to the solution at 0° C. and allowed to stir at room temperature overnight. After 22 hours at room temperature the reaction mixture is partitioned between dichloromethane and water. The mixture is acidified with HCl 25%. The organic phase is washed repeatedly with water, dried over sodium sulphate, filtered and concentrated by rotary evaporation. Chromatography of the residue on 600 g silica gel using toluene:ethyl acetate (99:1) as eluant and crystallization from ethyl acetate/hexane (1:2) yielded 18.82 g (79%) of 6-{[((2E)-3-{4-[(4-(4,4,4-trifluorobutoxy)benzoyl)oxy]phenyl}prop-2-enoyl)oxy]}hexyl 3,5-dinitrobenzoate as white crystals.

2.6 Preparation of 6-{[((2E)-3-{4-[(4-(4,4,4-trifluorobutoxy)benzoyl)oxy]phenyl}prop-2-enoyl)oxy]}hexyl 3,5-diaminobenzoate

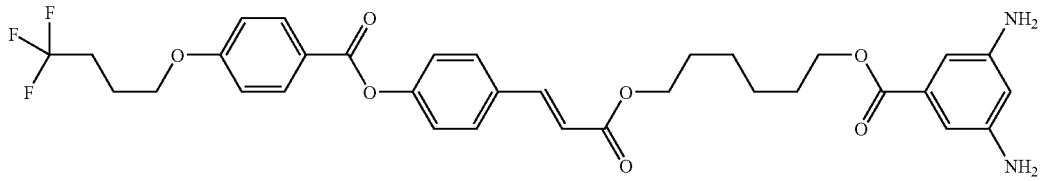

18.80 g (0.027 Mol) of 6-{[((2E)-3-{4-[(4-(4,4,4-trifluorobutoxy)benzoyl)oxy]phenyl}prop-2-enoyl)oxy]}hexyl 3,5-dinitrobenzoate are dissolved in a mixture of 350 ml of N,N-dimethylformamide and 25 ml water. 44.28 g (0.164 Mol) ferric chloride hexahydrate are added. 17.85 g (0.273 Mol) Zinc powder are added portionwise within 40 min. The mixture is allowed to react for 2 hours. The reaction mixture is then partitioned between ethyl acetate and water and filtered. The organic phase is washed repeatedly with water, dried over sodium sulfate, filtered and concentrated by rotary evaporation. Chromatography of the residue on 400 g silica gel using toluene:ethyl acetate (2:1) as eluant yielded 15.39 g (91%) of 6-{[((2E)-3-{4-[(4-(4,4,4-trifluorobutoxy)benzoyl)oxy]phenyl}prop-2-enoyl)oxy]}hexyl 3,5-diaminobenzoate as yellowish crystals.

The following diamines are synthesized in an analogous manner:

2-{[((2E)-3-{4-[(4-(trifluoroethoxy)benzoyl)oxy]phenyl}prop-2-enoyl)oxy]}ethyl 3,5-diaminobenzoate.
3-{[((2E)-3-{4-[(4-(trifluoroethoxy)benzoyl)oxy]phenyl}prop-2-enoyl)oxy]}propyl 3,5-diaminobenzoate.
4-{[((2E)-3-{4-[(4-(trifluoroethoxy)benzoyl)oxy]phenyl}prop-2-enoyl)oxy]}butyl 3,5-diaminobenzoate.
5-{[((2E)-3-{4-[(4-(trifluoroethoxy)benzoyl)oxy]phenyl}prop-2-enoyl)oxy]}pentyl 3,5-diaminobenzoate
7-{[((2E)-3-{4-[(4-(trifluoroethoxy)benzoyl)oxy]phenyl}prop-2-enoyl)oxy]}heptyl 3,5-diaminobenzoate.
8-{[((2E)-3-{4-[(4-(trifluoroethoxy)benzoyl)oxy]phenyl}prop-2-enoyl)oxy]}octyl 3,5-diaminobenzoate.
11-{[((2E)-3-{4-[(4-(trifluoroethoxy)benzoyl)oxy]phenyl}prop-2-enoyl)oxy]}undecyl 3,5-diaminobenzoate.
2-{[((2E)-3-{4-[(4-(trifluoromethoxy)benzoyl)oxy]phenyl}prop-2-enoyl)oxy]}ethyl 3,5-diaminobenzoate.
3-{[((2E)-3-{4-[(4-(trifluoromethoxy)benzoyl)oxy]phenyl}prop-2-enoyl)oxy]}propyl 3,5-diaminobenzoate.
4-{[((2E)-3-{4-[(4-(trifluoromethoxy)benzoyl)oxy]phenyl}prop-2-enoyl)oxy]}butyl 3,5-diaminobenzoate.
5-{[((2E)-3-{4-[(4-(trifluoromethoxy)benzoyl)oxy]phenyl}prop-2-enoyl)oxy]}pentyl 3,5-diaminobenzoate
6-{[((2E)-3-{4-[(4-(trifluoromethoxy)benzoyl)oxy]phenyl}prop-2-enoyl)oxy]}hexyll 3,5-diaminobenzoate
7-{[((2E)-3-{4-[(4-(trifluoromethoxy)benzoyl)oxy]phenyl}prop-2-enoyl)oxy]}heptyl 3,5-diaminobenzoate.
8-{[((2E)-3-{4-[(4-(trifluoromethoxy)benzoyl)oxy]phenyl}prop-2-enoyl)oxy]}octyl 3,5-diaminobenzoate.
2-{[((2E)-3-{4-[(4-(trifluoromethyl)benzoyl)oxy]phenyl}prop-2-enoyl)oxy]}ethyl 3,5-diaminobenzoate.
3-{[((2E)-3-{4-[(4-(trifluoromethyl)benzoyl)oxy]phenyl}prop-2-enoyl)oxy]}propyl 3,5-diaminobenzoate.
4-{[((2E)-3-{4-[(4-(trifluoromethyl)benzoyl)oxy]phenyl}prop-2-enoyl)oxy]}butyl 3,5-diaminobenzoate.
5-{[((2E)-3-{4-[(4-(trifluoromethyl)benzoyl)oxy]phenyl}prop-2-enoyl)oxy]}pentyl 3,5-diaminobenzoate
6-{[((2E)-3-{4-[(4-(trifluoromethyl)benzoyl)oxy]phenyl}prop-2-enoyl)oxy]}hexyll 3,5-diaminobenzoate
8-{[((2E)-3-{4-[(4-(trifluoromethyl)benzoyl)oxy]phenyl}prop-2-enoyl)oxy]}octyl 3,5-diaminobenzoate
11-{[((2E)-3-{4-[(4-(trifluoromethyl)benzoyl)oxy]phenyl}prop-2-enoyl)oxy]}undecyll 3,5-diaminobenzoate
2-[2-{[((2E)-3-{4-[(4-(trifluoroethoxy)benzoyl)oxy]phenyl}prop-2-enoyl)oxy]}ethoxy]ethyl 3,5-diaminobenzoate
2{2-[2-{[((2E)-3-{4-[(4-(trifluoroethoxy)benzoyl)oxy]phenyl}prop-2-enoyl)oxy]}ethoxy]ethoxy}ethyl 3,5-diaminobenzoate
2,2-dimethyl-3-{[((2E)-3-{4-[(4-(trifluoroethoxy)benzoyl)oxy]phenyl}prop-2-enoyl)oxy]}propyl 3,5-diaminobenzoate
2-{[((2E)-3-{4-[(4-(3,3,3-trifluoropropoxy)benzoyl)oxy]phenyl}prop-2-enoyl)oxy]}ethyl 3,5-diaminobenzoate
3-{[((2E)-3-{4-[(4-(3,3,3-trifluoropropoxy)benzoyl)oxy]phenyl}prop-2-enoyl)oxy]}propyl 3,5-diaminobenzoate
4-{[((2E)-3-{4-[(4-(3,3,3-trifluoropropoxy)benzoyl)oxy]phenyl}prop-2-enoyl)oxy]}butyl 3,5-diaminobenzoate.
6-{[((2E)-3-{4-[(4-(3,3,3-trifluoropropoxy)benzoyl)oxy]phenyl}prop-2-enoyl)oxy]}hexyl 3,5-diaminobenzoate
7-{[((2E)-3-{4-[(4-(3,3,3-trifluoropropoxy)benzoyl)oxy]phenyl}prop-2-enoyl)oxy]}heptyl 3,5-diaminobenzoate
8-{[((2E)-3-{4-[(4-(3,3,3-trifluoropropoxy)benzoyl)oxy]phenyl}prop-2-enoyl)oxy]}octyl 3,5-diaminobenzoate
11-{[((2E)-3-{4-[(4-(3,3,3-trifluoropropoxy)benzoyl)oxy]phenyl}prop-2-enoyl)oxy]}undecyl 3,5-diaminobenzoate
2-[2-{[((2E)-3-{4-[(4-(3,3,3-trifluoropropoxy)benzoyl)oxy]phenyl}prop-2-enoyl)oxy]}ethoxy]ethyl 3,5-diaminobenzoate
2{2-[2-{[((2E)-3-{4-[(4-(3,3,3-trifluoropropoxy)benzoyl)oxy]phenyl}prop-2-enoyl)oxy]}ethoxy]ethoxy}ethyl 3,5-diaminobenzoate 2,2-dimethyl-3-{[((2E)-3-{4-[(4-(3,3,3-trifluoropropoxy) benzoyl)oxy]phenyl}prop-2-enoyl)oxy]}propyl 3,5-diaminobenzoate 2-{[((2E)-3-{4-[(4-(4,4,4-trifluorobutoxy)benzoyl)oxy] phenyl}prop-2-enoyl)oxy]}ethyl 3,5-diaminobenzoate 3-{[((2E)-3-{4-[(4-(4,4,4-trifluorobutoxy)benzoyl)oxy] phenyl}prop-2-enoyl)oxy]}propyl 3,5-diaminobenzoate.

4-{[((2E)-3-{4-[(4-(4,4,4-trifluorobutoxy)benzoyl)oxy] phenyl}prop-2-enoyl)oxy]}butyl 3,5-diaminobenzoate.

5-{[((2E)-3-{4-[(4-(4,4,4-trifluorobutoxy)benzoyl)oxy] phenyl}prop-2-enoyl)oxy]}pentyl 3,5-diaminobenzoate 7-{[((2E)-3-{4-[(4-(4,4,4-trifluorobutoxy)benzoyl)oxy] phenyl}prop-2-enoyl)oxy]}heptyl 3,5-diaminobenzoate.

8-{[((2E)-3-{4-[(4-(4,4,4-trifluorobutoxy)benzoyl)oxy] phenyl}prop-2-enoyl)oxy]}octyl 3,5-diaminobenzoate.

11-{[((2E)-3-{4-[(4-(4,4,4-trifluorobutoxy)benzoyl)oxy] phenyl}prop-2-enoyl)oxy]}undecyl 3,5-diaminobenzoate.

2-[2-{[((2E)-3-{4-[(4-(4,4,4-trifluorobutoxy)benzoyl)oxy] phenyl}prop-2-enoyl)oxy]}ethoxy]ethyl 3,5-diaminobenzoate 2{2-[2-{[((2E)-3-{4-[(4-(4,4,4-trifluorobutoxy)benzoyl) oxy]phenyl}prop-2-enoyl)oxy]}ethoxy]ethoxy}ethyl 3,5-diaminobenzoate 2,2-dimethyl-3-{[((2E)-3-{4-[(4-(4,4,4-trifluorobutoxy) benzoyl)oxy]phenyl}prop-2-enoyl)oxy]}propyl 3,5-diaminobenzoate 2-{[((2E)-3-{4-[(4-(5,5,5-trifluoropentoxy)benzoyl)oxy] phenyl}prop-2-enoyl)oxy]}ethyl 3,5-diaminobenzoate 3-{[((2E)-3-{4-[(4-(5,5,5-trifluoropentoxy)benzoyl)oxy] phenyl}prop-2-enoyl)oxy]}propyl 3,5-diaminobenzoate 4-{[((2E)-3-{4-[(4-(5,5,5-trifluoropentoxy)benzoyl)oxy] phenyl}prop-2-enoyl)oxy]}butyl 3,5-diaminobenzoate 5-{[((2E)-3-{4-[(4-(5,5,5-trifluoropentoxy)benzoyl)oxy] phenyl}prop-2-enoyl)oxy]}pentyl 3,5-diaminobenzoate 6-{[((2E)-3-{4-[(4-(5,5,5-trifluoropentoxy)benzoyl)oxy] phenyl}prop-2-enoyl)oxy]}hexyl 3,5-diaminobenzoate 8-{[((2E)-3-{4-[(4-(5,5,5-trifluoropentoxy)benzoyl)oxy] phenyl}prop-2-enoyl)oxy]}octyl 3,5-diaminobenzoate 11-{[((2E)-3-{4-[(4-(5,5,5-trifluoropentoxy)benzoyl)oxy] phenyl}prop-2-enoyl)oxy]}undecyl 3,5-diaminobenzoate 2-[2-{[((2E)-3-{4-[(4-(5,5,5-trifluoropentoxy)benzoyl)oxy] phenyl}prop-2-enoyl)oxy]}ethoxy]ethyl 3,5-diaminobenzoate 2{2-[2-{[((2E)-3-{4-[(4-(5,5,5-trifluoropentoxy)benzoyl) oxy]phenyl}prop-2-enoyl)oxy]}ethoxy]ethoxy}ethyl 3,5-diaminobenzoate 2,2-dimethyl-3-{[((2E)-3-{4-[(4-(5,5,5-trifluoropentoxy) benzoyl)oxy]phenyl}prop-2-enoyl)oxy]}propyl 3,5-diaminobenzoate 2-{[((2E)-3-{4-[(4-(6,6,6-trifluorohexyloxy)benzoyl)oxy] phenyl}prop-2-enoyl)oxy]}ethyl 3,5-diaminobenzoate 3-{[((2E)-3-{4-[(4-(6,6,6-trifluorohexyloxy)benzoyl)oxy] phenyl}prop-2-enoyl)oxy]}propyl 3,5-diaminobenzoate 4-{[((2E)-3-{4-[(4-(6,6,6-trifluorohexyloxy)benzoyl)oxy] phenyl}prop-2-enoyl)oxy]}butyl 3,5-diaminobenzoate 5-{[((2E)-3-{4-[(4-(6,6,6-trifluorohexyloxy)benzoyl)oxy] phenyl}prop-2-enoyl)oxy]}pentyl 3,5-diaminobenzoate 7-{[((2E)-3-{4-[(4-(6,6,6-trifluorohexyloxy)benzoyl)oxy] phenyl}prop-2-enoyl)oxy]}heptyl 3,5-diaminobenzoate 8-{[((2E)-3-{4-[(4-(6,6,6-trifluorohexyloxy)benzoyl)oxy] phenyl}prop-2-enoyl)oxy]}octyl 3,5-diaminobenzoate 11-{[((2E)-3-{4-[(4-(6,6,6-trifluorohexyloxy)benzoyl)oxy] phenyl}prop-2-enoyl)oxy]}undecyl 3,5-diaminobenzoate 2-[2-{[((2E)-3-{4-[(4-(6,6,6-trifluorohexyloxy)benzoyl) oxy]phenyl}prop-2-enoyl)oxy]}ethoxy]ethyl 3,5-diaminobenzoate 2{2-[2-{[((2E)-3-{4-[(4-(6,6,6-trifluorohexyloxy)benzoyl) oxy]phenyl}prop-2-enoyl)oxy]}ethoxy]ethoxy}ethyl 3,5-diaminobenzoate 2,2-dimethyl-3-{[((2E)-3-{4-[(4-(6,6,6-trifluorohexyloxy) benzoyl)oxy]phenyl}prop-2-enoyl)oxy]}propyl 3,5-diaminobenzoate 3-{[((2E)-3-{4-[(3-methoxy 4-(3,3,3-trifluoropropoxy)benzoyl)oxy]phenyl}prop-2-enoyl)oxy]}propyl 3,5-diaminobenzoate 8-{[((2E)-3-{4-[(3-methoxy 4-(3,3,3-trifluoropropoxy)benzoyl)oxy]phenyl}prop-2-enoyl)oxy]}octyl 3,5-diaminobenzoate 11-{[((2E)-3-{4-[(3-methoxy 4-(3,3,3-trifluoropropoxy) benzoyl)oxy]phenyl}prop-2-enoyl)oxy]}undecyl 3,5-diaminobenzoate 6-{[((2E)-3-{4-[(3-methoxy 4-(4,4,4-trifluorobutoxy)benzoyl)oxy]phenyl}prop-2-enoyl)oxy]}hexyll 3,5-diaminobenzoate 8-{[((2E)-3-{4-[(3-methoxy 4-(4,4,4-trifluorobutoxy)benzoyl)oxy]phenyl}prop-2-enoyl)oxy]}octyl 3,5-diaminobenzoate 11-{[((2E)-3-{4-[(3-methoxy 4-(4,4,4-trifluorobutoxy)benzoyl)oxy]phenyl}prop-2-enoyl)oxy]}undecyl 3,5-diaminobenzoate 4-{[((2E)-3-{4-[(3-methoxy 4-(5,5,5-trifluoropentoxy)benzoyl)oxy]phenyl}prop-2-enoyl)oxy]}butyl 3,5-diaminobenzoate 6-{[((2E)-3-{4-[(3-methoxy 4-(5,5,5-trifluoropentoxy)benzoyl)oxy]phenyl}prop-2-enoyl)oxy]}hexyl3,5-diaminobenzoate 4-{[((2E)-3-{4-[(3-methoxy 4-(6,6,6-trifluorohexyloxy) benzoyl)oxy]phenyl}prop-2-enoyl)oxy]}butyl 3,5-diaminobenzoate 6-{[((2E)-3-{4-[(3-methoxy 4-(6,6,6-trifluorohexyloxy) benzoyl)oxy]phenyl}prop-2-enoyl)oxy]}hexyl 3,5-diaminobenzoate 2-{[((2E)-3-{4-[(4-(4, 4, 5, 5, 5-pentafluoropentoxy)benzoyl)oxy]phenyl}prop-2-enoyl)oxy]}ethyl 3,5-diaminobenzoate 3-{[((2E)-3-{4-[(4-(4,4,5,5,5-pentafluoropentoxy)benzoyl) oxy]phenyl}prop-2-enoyl)oxy]}propyl 3,5-diaminobenzoate 4-{[((2E)-3-{4-[(4-(4,4,5,5,5-pentafluoropentoxy)benzoyl) oxy]phenyl}prop-2-enoyl)oxy]}butyl 3,5-diaminobenzoate 6-{[((2E)-3-{4-[(4-(4,4,5,5,5-pentafluoropentoxy)benzoyl) oxy]phenyl}prop-2-enoyl)oxy]}hexyl 3,5-diaminobenzoate 7-{[((2E)-3-{4-[(4-(4,4,5,5,5-pentafluoropentoxy)benzoyl) oxy]phenyl}prop-2-enoyl)oxy]}heptyl 3,5-diaminobenzoate 8-{[((2E)-3-{4-[(4-(4,4,5,5,5-pentafluoropentoxy)benzoyl) oxy]phenyl}prop-2-enoyl)oxy]}octyl 3,5-diaminobenzoate 11-{[((2E)-3-{4-[(4-(4,4,5,5,5-pentafluoropentoxy)benzoyl)oxy]phenyl}prop-2-enoyl)oxy]}undecyl 3,5-diaminobenzoate 2-[2-{[((2E)-3-{4-[(4-(4, 4, 5, 5, 5-pentafluoropentoxy)benzoyl)oxy]phenyl}prop-2-enoyl)oxy]}ethoxy]ethyl 3,5-diaminobenzoate 2{2-[2-{[((2E)-3-{4-[(4-(4,4,5,5,5-pentafluoropentoxy)benzoyl)oxy]phenyl}prop-2-enoyl)oxy]}ethoxy] ethyl}ethyl 3,5-diaminobenzoate 2,2-Dimethyl-3-{[((2E)-3-{4-[(4-(4,4,5,5,5-pentafluoropentoxy)benzoyl)oxy]phenyl}prop-2-enoyl)oxy]}propyl 3,5-diaminobenzoate 2-{[((2E)-3-{4-[(4-(1,1,2,2-tetrafluoroethoxy)benzoyl)oxy]phenyl}prop-2-enoyl)oxy]}ethyl 3,5-diaminobenzoate
3-{[((2E)-3-{4-[(4-(1,1,2,2-tetrafluoroethoxy)benzoyl)oxy]phenyl}prop-2-enoyl)oxy]}propyl 3,5-diaminobenzoate
4-{[((2E)-3-{4-[(4-(1,1,2,2-tetrafluoroethoxy)benzoyl)oxy]phenyl}prop-2-enoyl)oxy]}butyl 3,5-diaminobenzoate
5-{[((2E)-3-{4-[(4-(1,1,2,2-tetrafluoroethoxy)benzoyl)oxy]phenyl}prop-2-enoyl)oxy]}pentyl 3,5-diaminobenzoate
6-{[((2E)-3-{4-[(4-(1,1,2,2-tetrafluoroethoxy)benzoyl)oxy]phenyl}prop-2-enoyl)oxy]}hexyll 3,5-diaminobenzoate
7-{[((2E)-3-{4-[(4-(1,1,2,2-tetrafluoroethoxy)benzoyl)oxy]phenyl}prop-2-enoyl)oxy]}heptyl 3,5-diaminobenzoate.
8-{[((2E)-3-{4-[(4-(1,1,2,2-tetrafluoroethoxy)benzoyl)oxy]phenyl}prop-2-enoyl)oxy]}octyl 3,5-diaminobenzoate
11-{[((2E)-3-{4-[(4-(1,1,2,2-tetrafluoroethoxy)benzoyl)oxy]phenyl}prop-2-enoyl)oxy]}undecyl 3,5-diaminobenzoate 6-{[((2E)-3-{4-[(4-{[(4,4,4-trifluorobutoxy)carbonyl]amino}benzoyl)oxy]phenyl}prop-2-enoyl)oxy]}hexyll 3,5-diaminobenzoate
6-{[((2E)-3-{4-[(4-{[(4,4,5,5,5-pentafluoropentoxy)carbonyl]amino}benzoyl)oxy]phenyl}prop-2-enoyl)oxy]}hexyll 3,5-diaminobenzoate
6-{[((2E)-3-{4-[(4-({[(4,4,5,5,6,6,6-heptafluorohexyloxy)carbonyl]amino})benzoyl)oxy]phenyl}prop-2-enoyl)oxy]}hexyll 3,5-diaminobenzoate

EXAMPLE 3

Synthesis

Preparation of 3,5-Diaminobenzyl (2E)3-{4-[(4-(4,4,4-trifluorobutoxy)benzoyl)oxy]phenyl}acrylate 3.1 Preparation of 3,5-dinitrobenzyl (2E)3-{4-[(4-(4,4,4-trifluorobutoxy)benzoyl)oxy]phenyl}acrylate

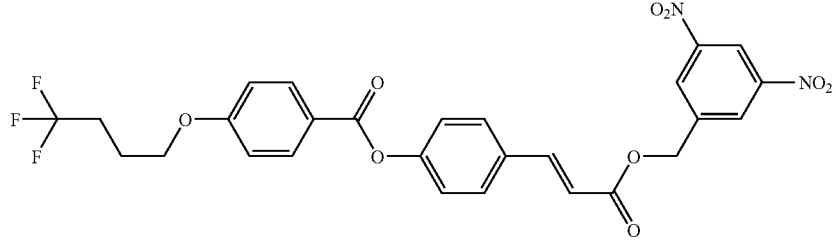

1.00 g (51.0 mmol) of 3,5-dinitrobenzylalcohol, 2.00 g (51.0 mmol) of (2E)-3-(4-{[4-(4,4,4-trifluorobutoxy)ben- zoyl]oxy}phenyl)acrylic acid, 62 mg (0.51 mmol) of 4-Dimethylaminopyridine are dissolved in 10 ml of dichloromethane. 1.07 g (56.0 mmol) of N-(3-Dimethylaminopropyl)-N'-ethylcarbodiimide hydrochloride (EDC hydrochloride) are added at 0° C. The solution is stirred for 1 h at 0° C. and allowed to stir at room temperature overnight. After 22 hours at room temperature the reaction mixture is partitioned between dichloromethane and water. The organic phase is washed repeatedly with water, dried over sodium sulphate, filtered and concentrated by rotary evaporation to yield 3,5-dinitrobenzyl (2E)3-{4-[(4-(4,4,4-trifluorobutoxy)benzoyl)oxy]phenyl}acrylate 2.1 g as colorless crystals.

3.2 Preparation of 3,5-Diaminobenzyl (2E)3-{4-[(4-(4,4,4-trifluorobutoxy)benzoyl)oxy]phenyl}acrylate

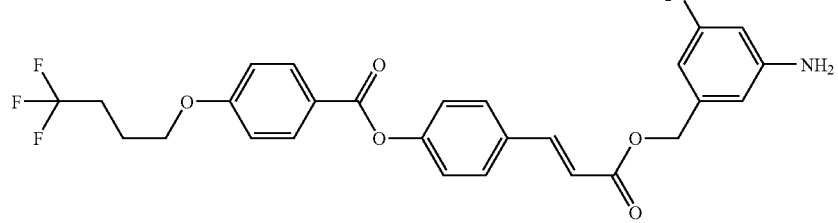

5.30 g (9.22 mmol) of (2E)3-{4-[(4-(4,4,4-trifluorobutoxy)benzoyl)oxy]phenyl}acrylate are dissolved in a mixture of 55 ml of N,N-dimethylformamide and 6 ml water. 14.98 g (55.3 mmol) ferric chloride hexahydrate are added. 6.03 g (91.8 mmol) Zinc powder are added portionwise within 40 min. The mixture is allowed to react for 2 hours. The reaction mixture is then partitioned between ethyl acetate and water and filtered. The organic phase is washed repeatedly with water, dried over sodium sulfate, filtered and concentrated by rotary evaporation. Chromatography of the residue on 200 g silica gel using toluene:ethyl acetate (1:1) as eluant and crystallization form ethylacetate:hexane mixture yielded 3.8 g 3,5-Diaminobenzyl (2E)3-{4-[(4-(4,4,4-trifluorobutoxy)benzoyl)oxy]phenyl}acrylate as yellowish crystals The following diamines are synthesized in an analogous manner:
3,5-Diaminobenzyl (2E)3-{4-[(4-trifluoromethoxybenzoyl)oxy]phenyl}acrylate
3,5-Diaminobenzyl (2E)3-{4-[(4-(2,2,2-trifluoroethoxy)benzoyl)oxy]phenyl}acrylate
3,5-Diaminobenzyl (2E)3-{4-[(4-(5,5,5-trifluoropentyloxy)benzoyl)oxy]phenyl}acrylate 3,5-Diaminobenzyl (2E)3-{4-[(4-(4,4,5,5,5-pentafluoropentyloxy)benzoyl)oxy]phenyl}acrylate
3,5-Diaminobenzyl (2E)3-{4-[(4-(3,3,4,4,5,5,6,6,6-nonafluorohexyloxy)benzoyl)oxy]phenyl}acrylate
3,5-Diaminobenzyl (2E)3-{4-[(4-(2,2,3,3,3-pentafluoropyloxy)benzoyl)oxy]phenyl}acrylate
3,5-Diaminobenzyl (2E)3-{4-[(4-(2,2,3,4,4,4-hexafluorobutoxy)benzoyl)oxy]phenyl}acrylate
3,5-Diaminobenzyl (2E)3-{4-[(4-(1,1,2,2-tetrafluoroethoxy)benzoyl)oxy]phenyl}acrylate
3,5-Diaminobenzyl (2E)3-{4-[(4-(1,1,2,2-tetrafluoropropoxy)benzoyl)oxy]phenyl}acrylate
3,5-Diaminobenzyl(2E)3-{4-[(4-(4, 4, 5, 5, 6, 6, 6-heptafluorohexyloxy)benzoyl)oxy]phenyl}acrylate
3,5-Diaminobenzyl (2E)3-{4-[(4-(4,5,5,5-tetrafluoro-4-(trifluoromethyl)pentyloxy)benzoyl)oxy]phenyl}acrylate
3,5-Diaminobenzyl (2E)3-{4-{[(4-(4,4,5,5,6,6,6-heptafluorohexyloyl)oxy)benzoyl)oxy]phenyl}acrylate
3,5-Diaminobenzyl (2E)3-{4-[(4-[(4,4,4-trifluorobutoxy)carbonyl]amino)benzoyl)oxy]phenyl}acrylate
3,5-Diaminobenzyl (2E)3-{4-[(4-[(4,4,4-trifluoropentyloxy)carbonyl]amino) benzoyl]oxy}phenyl}acrylate
3,5-Diaminobenzyl (2E)3-{4-[4-(4,4,5,5,5-pentafluoropentyloyloxy)benzoyl oxy]phenyl}acrylate
3,5-Diaminobenzyl (2E)3-{4-[4-(4,4,5,5,6,6,6-heptafluorohexyloyloxy)benzoyl oxy]phenyl}acrylate
3,5-Diaminobenzyl (2E)3-{4-[(3-fluoro-4-(4,4,4-trifluorobutoxy)benzoyl)oxy]phenyl}acrylate
2,5-Diaminobenzyl (2E)3-{4-[(4-trifluoromethoxybenzoyl)oxy]phenyl}acrylate
2,5-Diaminobenzyl (2E)3-{4-[(4-(2,2,2-trifluoroethoxy)benzoyl)oxy]phenyl}acrylate
2,5-Diaminobenzyl (2E)3-{4-[(4-(5,5,5-trifluorobutoxy)benzoyl)oxy]phenyl}acrylate
2,5-Diaminobenzyl (2E)3-{4-[(4-(5,5,5-trifluoropentyloxy)benzoyl)oxy]phenyl}acrylate
2,5-Diaminobenzyl (2E)3-{4-[(4-(4,4,5,5,5-pentafluoropentyloxy)benzoyl)oxy]phenyl}acrylate
2,5-Diaminobenzyl (2E)3-{4-[(4-(1,1,2,2-tetrafluoroethoxy)benzoyl)oxy]phenyl}acrylate
2,5-Diaminobenzyl (2E)3-{4-[(4-(1,1,2,2-tetrafluoropropoxy)benzoyl)oxy]phenyl}acrylate
2,5-Diaminobenzyl (2E)3-{4-[(4-(4,4,5,5,6,6,6-heptafluorohexyloxy)benzoyl)oxy]phenyl}acrylate
2,5-Diaminobenzyl (2E)3-{4-{[(4-(4, 4, 5, 5, 6, 6, 6-heptafluorohexyloyl)oxy)benzoyl)oxy]phenyl}acrylate
2,5-Diaminobenzyl (2E)3-{4-[(4-[(4,4,4-trifluorobutoxy)carbonyl]amino)benzoyl)oxy]phenyl}acrylate
2,5-Diaminobenzyl (2E)3-{4-[(4-[(4,4,4-trifluoropentyloxy)carbonyl]amino) benzoyl]oxy}phenyl}acrylate
2,5-Diaminobenzyl (2E)3-{4-[4-(4,4,5,5,5-pentafluoropentyloyloxy)benzoyl oxy]phenyl}acrylate
2,5-Diaminobenzyl (2E)3-{4-[4-(4,4,5,5,6,6,6-heptafluorohexyloyloxy)benzoyl oxy]phenyl}acrylate2,5-Diaminobenzyl (2E)3-{4-[(2-fluoro-4-(4,4,4-trifluorobutoxy)benzoyl)oxy]phenyl}acrylate
2,4-Diaminobenzyl (2E)3-{4-[(4-trifluoromethoxybenzoyl)oxy]phenyl}acrylate
2,4-Diaminobenzyl (2E)3-{4-[(4-(2,2,2-trifluoroethoxy)benzoyl)oxy]phenyl}acrylate
2,4-Diaminobenzyl (2E)3-{4-[(4-(5,5,5-trifluoropentyloxy)benzoyl)oxy]phenyl}acrylate
2,4-Diaminobenzyl (2E)3-{4-[(4-(4,4,4-trifluorobutoxy)benzoyl)oxy]phenyl}acrylate
2,4-Diaminobenzyl (2E)3-{4-[(4-(4,4,5,5,5-pentafluoropentyloxy)benzoyl)oxy]phenyl}acrylate
2,4-Diaminobenzyl (2E)3-{4-[(4-(1,1,2,2-tetrafluoroethoxy)benzoyl)oxy]phenyl}acrylate
2,4-Diaminobenzyl (2E)3-{4-[(4-(1,1,2,2-tetrafluoropropoxy)benzoyl)oxy]phenyl}acrylate
2,4-Diaminobenzyl (2E)3-{4-[(4-(4,4,5,5,6,6,6-heptafluorohexyloxy)benzoyl)oxy]phenyl}acrylate
2,4-Diaminobenzyl (2E)3-{4-{[(4-(4,4,5,5,6,6,6-heptafluorohexyloyl)oxy)benzoyloxy]phenyl}acrylate
2,4-Diaminobenzyl (2E)3-{4-[(4-[(4,4,4-trifluorobutoxy)carbonyl]amino)benzoyl)oxy]phenyl}acrylate
2,4-Diaminobenzyl (2E)3-{4-[(4-[(4,4,4-trifluoropentyloxy)carbonyl]amino) benzoyl]oxy}phenyl}acrylate
2,4-Diaminobenzyl (2E)3-{4-[4-(4, 4, 5, 5, 5-pentafluoropentyloyloxy)benzoyl oxy]phenyl}acrylate
2,4-Diaminobenzyl (2E)3-{4-[4-(4,4,5,5,6,6,6-heptafluorohexyloyloxy)benzoyl oxy]phenyl}acrylate
2,4-Diaminobenzyl (2E)3-{4-[(3-fluoro-4-(4,4,4-trifluorobutoxy)benzoyl)oxy]phenyl}acrylate

EXAMPLE 4

Synthesis

Preparation of 2-(2,4-Diaminophenyl)ethyl (2E)3-{4-[(4-(4,4,5,5,5-pentafluoropentoxy)benzoyl)oxy]phenyl}acrylate 4.1 Preparation of 2-(2,4-dinitrophenyl)ethanol

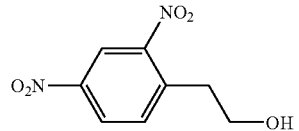

22.6 g (100 mmol) 2,4-dinitrophenylacetic acid are dissolved in 150 ml tetrahydrofuran and added dropwise in a the course of 2 hours to 300 ml (300 mmol) of a borane-tetrahydrofuran complex 1.0 M solution in tetrahydrofuran. After 3 hours at 25° C., 200 ml water are carefully added. The reaction mixture is then partitioned between ethyl acetate and water; the organic phase was washed repeatedly with water, dried over sodium sulfate, filtered and concentrated by rotary evaporation. Chromatography of the residue on 400 g silica gel using toluene:ethyl acetate 1:1 as eluant and crystallization form ethylacetate:hexane mixture to yield 20.7 g (98%) of 2-(2,4-dinitrophenyl)ethanol as yellowish crystals.

4.2 Preparation of 2-(2,4-Dinitrophenyl)ethyl (2E)3-{4-[(4-(4,4,5,5,5-pentafluoropentoxy)benzoyl)oxy]phenyl}acrylate

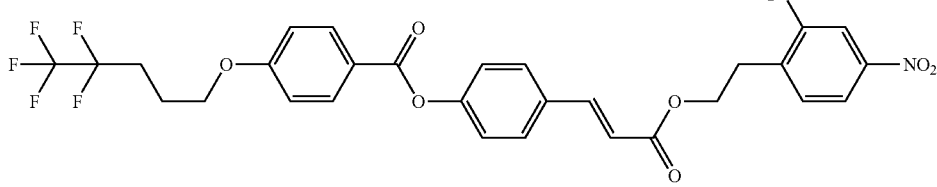

2.50 g (11.8 mmol) of 2-(2,4-dinitrophenyl)ethanol, 5.24 g (11.8 mmol) of (2E)-3-(4-{[4-(4,4,5,5,5-pentafluoropentoxy)benzoyl]oxy}phenyl)acrylic acid, 144 mg (1.2 mmol) of 4-Dimethylaminopyridine are dissolved in 30 ml of dichloromethane. 2.48 g (13.0 mmol) of N-(3-Dimethylaminopropyl)-N'-ethylcarbodiimide hydrochloride (EDC hydrochloride) are added at 0° C. The solution is stirred for 1 h at 0° C. and allowed to stir at room temperature overnight. After 22 hours at room temperature the reaction mixture is partitioned between dichloromethane and water. The organic phase is washed repeatedly with water, dried over sodium sulphate, filtered and concentrated by rotary evaporation. Chromatography of the residue on 200 g silica gel using toluene:ethyl acetate 95:5 as eluant and crystallization form ethylacetate:hexane mixture to yield 5.35 g (71%) 2-(2,4-Dinitrophenyl)ethyl (2E)3-{4-[(4-(4,4,5,5,5-pentafluoropentoxy)benzoyl)oxy]phenyl}acrylate as colorless crystals.

4.3 Preparation of 2-(2,4-Diaminophenyl)ethyl (2E)3-{4-[(4-(4,4,5,5,5-pentafluoropentoxy)benzoyl)oxy]phenyl}acrylate

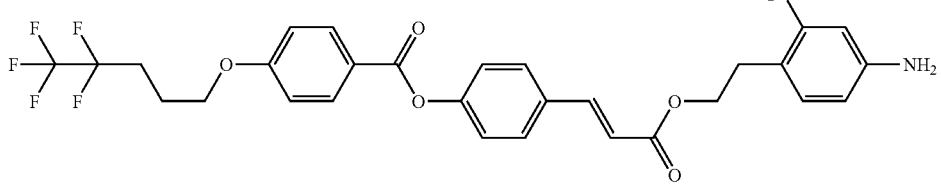

5.35 g (8.38 mmol) of (2E)3-{4-[(4-(4,4,5,5,5-pentafluoropentoxy)benzoyl)oxy]phenyl}acrylate are dissolved in a mixture of 54 ml of N,N-dimethylformamide and 6 ml water. 13.9 g (51.4 mmol) ferric chloride hexahydrate are added. 5.60 g (85.7 mmol) Zinc powder are added portionwise within 60 min. The mixture is allowed to react for 2 hours. The reaction mixture is then partitioned between ethyl acetate and water and filtered. The organic phase is washed repeatedly with water, dried over sodium sulfate, filtered and concentrated by rotary evaporation. Filtration of the residue on 200 g silica gel using toluene:ethyl acetate (1:3) as eluant and crystallization form ethylacetate:hexane mixture yielded 3.30 g 2-(2,4-Diaminophenyl)ethyl (2E)3-{4-[(4-(4,4,5,5,5-pentafluoropentoxy)benzoyl)oxy]phenyl}acrylate as yellowish crystals 2-(2,4-Diaminophenyl)ethyl (2E)3-{4-[(4-(4,4,4-trifluorobutoxy)benzoyl)oxy]phenyl}acrylate is prepared analogous to example 4 using (2E)-3-(4-{[4-(4,4,4-trifluorobutoxy)benzoyl]oxy}phenyl)acrylic acid.

The following diamines are synthesized in an analogous manner:

2-(3,5-Diaminophenyl)ethyl (2E)3-{4-[(4-trifluoromethoxybenzoyl)oxy]phenyl}acrylate
2-(3,5-Diaminophenyl)ethyl (2E)3-{4-[(4-(2,2,2-trifluoroethoxy)benzoyl)oxy]phenyl}acrylate
2-(3,5-Diaminophenyl)ethyl (2E)3-{4-[(4-(4,4,4-trifluorobutoxy)benzoyl)oxy]phenyl}acrylate
2-(3,5-Diaminophenyl)ethyl (2E)3-{4-[(4-(5,5,5-trifluoropentyloxy)benzoyl)oxy]phenyl}acrylate
2-(3,5-Diaminophenyl)ethyl (2E)3-{4-[(4-(4,4,5,5,5-pentafluoropentoxy)benzoyl)oxy]phenyl}acrylate
2-(3,5-Diaminophenyl)ethyl (2E)3-{4-[(4-(1,1,2,2-tetrafluoroethoxy)benzoyl)oxy]phenyl}acrylate
2-(3,5-Diaminophenyl)ethyl (2E)3-{4-[(4-(4,4,4-trifluorobutanoyl)oxy)benzoyl]oxy}phenyl}acrylate
2-(3,5-Diaminophenyl)ethyl (2E)3-{4-[(3-methoxy-4-trifluoromethoxybenzoyl)oxy]phenyl}acrylate
2-(3,5-Diaminophenyl)ethyl (2E)3-{4-[(3-methoxy 4-(2,2,2-trifluoroethoxy)benzoyl)oxy]phenyl}acrylate
2-(3,5-Diaminophenyl)ethyl (2E)3-{4-[(3-methoxy 4-(4,4,4-trifluorobutoxy)benzoyl)oxy]phenyl}acrylate
2-(3,5-Diaminophenyl)ethyl (2E)3-{4-[(3-methoxy 4-(5,5,5-trifluoropentyloxy)benzoyl)oxy]phenyl}acrylate
2-(3,5-Diaminophenyl)ethyl (2E)3-{4-[(3-methoxy 4-(4,4,5,5,5-pentafluoropentoxy)benzoyl)oxy]phenyl}acrylate
2-(3,5-Diaminophenyl)ethyl (2E)3-{4-[(3-methoxy 4-(1,1,2,2-tetrafluoroethoxy)benzoyl)oxy]phenyl}acrylate
2-(3,5-Diaminophenyl)ethyl (2E)3-{4-[(3-methoxy 4-(4,4,4-trifluorobutanoyl)oxy)benzoyl]oxy}phenyl}acrylate
2-(3,5-Diaminophenyl)ethyl (2E)3-{4-[(4-trifluoromethoxybenzoyl)oxy]-3-methoxyphenyl}acrylate
2-(3,5-Diaminophenyl)ethyl (2E)3-{4-[(4-(2,2,2-trifluoroethoxy)benzoyl)oxy]-3-methoxyphenyl}acrylate
2-(3,5-Diaminophenyl)ethyl (2E)3-{4-[(4-(4,4,4-trifluorobutoxy)benzoyl)oxy]-3-methoxyphenyl}acrylate
2-(3,5-Diaminophenyl)ethyl (2E)3-{4-[(4-(5,5,5-trifluoropentyloxy)benzoyl)oxy]-3-methoxyphenyl}acrylate
2-(3,5-Diaminophenyl)ethyl (2E)3-{4-[(4-(4,4,5,5,5-pentafluoropentoxy)benzoyl)oxy]-3-methoxyphenyl}acrylate
2-(3,5-Diaminophenyl)ethyl (2E)3-{4-[(4-(1,1,2,2-tetrafluoroethoxy)benzoyl)oxy]-3-methoxyphenyl}acrylate 2-(3,5-Diaminophenyl)ethyl (2E)3-{4-[(4-(4,4,4-trifluorobutanoyl)oxy)benzoyl]oxy}-3-methoxyphenyl}acrylate
2-(3,5-Diaminophenyl)ethyl (2E)3-{4-[(4-trifluoromethoxyphenoxy)carbonyl]phenyl}acrylate
2-(3,5-Diaminophenyl)ethyl (2E)3-{4-[(4-(2,2,2-trifluoroethoxy)phenoxy)carbonyl]phenyl}acrylate
2-(3,5-Diaminophenyl)ethyl (2E)3-{4-[(4-(4,4,4-trifluorobutoxy)phenoxy)carbonyl]phenyl}acrylate
2-(3,5-Diaminophenyl)ethyl (2E)3-{4-[(4-(5,5,5-trifluoropentyloxy)phenoxy)carbonyl]phenyl}acrylate
2-(3,5-Diaminophenyl)ethyl (2E)3-{4-[(4-(4,4,5,5,5-pentafluoropentoxy)phenoxy)carbonyl]phenyl}acrylate
2-(3,5-Diaminophenyl)ethyl (2E)3-{4-[(4-(1,1,2,2-tetrafluoroethoxy)phenoxy)carbonyl]phenyl}acrylate
2-(2,5-Diaminophenyl)ethyl (2E)3-{4-[(4-trifluoromethoxybenzoyl)oxy]phenyl}acrylate
2-(2,5-Diaminophenyl)ethyl (2E)3-{4-[(4-(2,2,2-trifluoroethoxy)benzoyl)oxy]phenyl}acrylate
2-(2,5-Diaminophenyl)ethyl (2E)3-{4-[(4-(4,4,4-trifluorobutoxy)benzoyl)oxy]phenyl}acrylate
2-(2,5-Diaminophenyl)ethyl (2E)3-{4-[(4-(5,5,5-trifluoropentyloxy)benzoyl)oxy]phenyl}acrylate
2-(2,5-Diaminophenyl)ethyl (2E)3-{4-[(4-(4, 4, 5, 5, 5-pentafluoropentoxy)benzoyl)oxy]phenyl}acrylate
2-(2,5-Diaminophenyl)ethyl (2E)3-{4-[(4-(1,1,2,2-tetrafluoroethoxy)benzoyl)oxy]phenyl}acrylate
2-(2,5-Diaminophenyl)ethyl (2E)3-{4-[(4-(4,4,4-trifluorobutanoyl)oxy)benzoyl]oxy}phenyl}acrylate
2-(2,4-Diaminophenyl)ethyl (2E)3-{4-[(4-trifluoromethoxybenzoyl)oxy]phenyl}acrylate
2-(2,4-Diaminophenyl)ethyl (2E)3-{4-[(4-(2,2,2-trifluoroethoxy)benzoyl)oxy]phenyl}acrylate
2-(2,4-Diaminophenyl)ethyl (2E)3-{4-[(4-(4,4,4-trifluorobutoxy)benzoyl)oxy]phenyl}acrylate
2-(2,4-Diaminophenyl)ethyl (2E)3-{4-[(4-(5,5,5-trifluoropentyloxy)benzoyl)oxy]phenyl}acrylate
2-(2,4-Diaminophenyl)ethyl (2E)3-{4-[(4-(2,2,3,3,3-pentafluoropropyloxy)benzoyl)oxy]phenyl}acrylate
2-(2,4-Diaminophenyl)ethyl (2E)3-{4-[(4-(2,2,3,4,4,4-hexafluorobutoxy)benzoyl)oxy]phenyl}acrylate
2-(2,4-Diaminophenyl)ethyl (2E)3-{4-[(4-(3,3,4,4,5,5,6,6,6-nonafluorohexyloxy)benzoyl)oxy]phenyl}acrylate
2-(2,4-Diaminophenyl)ethyl (2E)3-{4-[(4-(1,1,2,2-tetrafluoroethoxy)benzoyl)oxy]phenyl}acrylate
2-(2,4-Diaminophenyl)ethyl (2E)3-{4-[(4-(1,1,2,2-tetrafluoropropoxy)benzoyl)oxy]phenyl}acrylate
2-(2,4-Diaminophenyl)ethyl (2E)3-{4-[(4-(4,4,5,5,6,6,6-heptafluorohexyloxy)benzoyl)oxy]phenyl}acrylate
2-(2,4-Diaminophenyl)ethyl (2E)3-{4-[(4-(5,5,6,6,6-pentafluorohexyl)benzoyl)oxy]phenyl}acrylate
2-(2,4-Diaminophenyl)ethyl (2E)3-{4-[(4-(4,4,4-trifluorobutanoyl)oxy)benzoyl]oxy}phenyl}acrylate
2-(2,4-Diaminophenyl)ethyl (2E)3-{4-[(3-fluoro-4-(4,4,4-trifluorobutoxy)benzoyl) oxy]phenyl}acrylate
2-(2,4-Diaminophenyl)ethyl (2E)3-{4-[(4-(5,5,5-trifluoropentoxy)benzoyl)oxy]phenyl}acrylate
2-(2,4-Diaminophenyl)ethyl (2E)3-{4-[(3,4-di(4,4,4-trifluorobutoxy)benzoyl)oxy]phenyl}acrylate
2-(2,4-Diaminophenyl)ethyl (2E)3-{4-[(4-(4,4,5,5,5-pentafluoropentoxy carbonyl)phenoxy)carbonyl]phenyl}acrylate
2-(2,4-Diaminophenyl)ethyl (2E)3-{4-[(4-[(4,4,4-trifluorobutoxy)carbonyl]amino)benzoyl]oxy}phenyl}acrylate.
2-(2,4-Diaminophenyl)ethyl (2E)3-{4-[(4-[(4,4,5,5,5-pentafluoropentoxy)carbonyl]amino) benzoyl]oxy}phenyl}acrylate
2-(2,4-Diaminophenyl)ethyl (2E)3-{4-[(3-methoxy-4-trifluoromethoxybenzoyl)oxy]phenyl}acrylate
2-(2,4-Diaminophenyl)ethyl (2E)3-{4-[(3-methoxy 4-(2,2,2-trifluoroethoxy)benzoyl)oxy]phenyl}acrylate
2-(2,4-Diaminophenyl)ethyl (2E)3-{4-[(3-methoxy 4-(4,4,4-trifluorobutoxy)benzoyl)oxy]phenyl}acrylate
2-(2,4-Diaminophenyl)ethyl (2E)3-{4-[(3-methoxy 4-(5,5,5-trifluoropentyloxy)benzoyl)oxy]phenyl}acrylate
2-(2,4-Diaminophenyl)ethyl (2E)3-{4-[(3-methoxy 4-(4,4,5,5,5-pentafluoropentoxy)benzoyl)oxy]phenyl}acrylate
2-(2,4-Diaminophenyl)ethyl (2E)3-{4-[(3-methoxy 4-(1,1,2,2-tetrafluoroethoxy)benzoyl)oxy]phenyl}acrylate
2-(2,4-Diaminophenyl)ethyl (2E)3-{4-[(3-methoxy 4-(4,4,4-trifluorobutanoyl)oxy)benzoyl]oxy}phenyl}acrylate
2-(2,4-Diaminophenyl)ethyl (2E)3-{4-[(4-(4,4,4-trifluorobutoxy)benzoyl)oxy]-3-methoxy phenyl}acrylate
2-(2,4-Diaminophenyl)ethyl (2E)3-{4-[(4-(5,5,5-trifluoropentyloxy)benzoyl)oxy]-3-methoxyphenyl}acrylate
2-(2,4-Diaminophenyl)ethyl (2E)3-{4-[(4-(4, 4, 5, 5, 5-pentafluoropentoxy)benzoyl)oxy]-3-methoxyphenyl}acrylate
2-(2,4-Diaminophenyl)ethyl (2E)3-{4-[(4-(1,1,2,2-tetrafluoroethoxy)benzoyl)oxy]-3-methoxyphenyl}acrylate
2-(2,4-Diaminophenyl)ethyl (2E)3-{4-[(4-(4,4,4-trifluorobutanoyl)oxy)benzoyl]oxy}-3-methoxyphenyl}acrylate
2-(2,4-Diaminophenyl)ethyl (2E)3-{4-[(4-(4,4,4-trifluorobutoxy)phenoxy)carbonyl]phenyl}acrylate
2-(2,4-Diaminophenyl)ethyl (2E)3-{4-[(4-(5,5,5-trifluoropentyloxy)phenoxy)carbonyl]phenyl}acrylate
2-(2,4-Diaminophenyl)ethyl (2E)3-{4-[(4-(4,4,5,5,5-pentafluoropentoxy)phenoxy)carbonyl]phenyl}acrylate
2-(2,4-Diaminophenyl)ethyl (2E)3-{4-[(4-(1,1,2,2-tetrafluoroethoxy)phenoxy)carbonyl]phenyl}acrylate
3-(3,5-Diaminophenyl)propyl (2E)3-{4-[(4-trifluoromethoxybenzoyl)oxy]phenyl}acrylate
3-(3,5-Diaminophenyl)propyl (2E)3-{4-[(4-(2,2,2-trifluoroethoxy)benzoyl)oxy]phenyl}acrylate
3-(3,5-Diaminophenyl)propyl (2E)3-{4-[(4-(4,4,4-trifluorobutoxy)benzoyl)oxy]phenyl}acrylate
3-(3,5-Diaminophenyl)propyl (2E)3-{4-[(4-(5,5,5-trifluoropentyloxy)benzoyl)oxy]phenyl}acrylate
3-(3,5-Diaminophenyl)propyl (2E)3-{4-[(4-(4,4,5,5,5-pentafluoropentoxy)benzoyl)oxy]phenyl}acrylate
3-(3,5-Diaminophenyl)propyl (2E)3-{4-[(4-(1,1,2,2-tetrafluoroethoxy)benzoyl)oxy]phenyl}acrylate
3-(3,5-Diaminophenyl)propyl (2E)3-{4-[(4-(4,4,4-trifluorobutanoyl)oxy)benzoyl]oxy}phenyl}acrylate 3-(2,4-Diaminophenyl)propyl (2E)3-{4-[(4-(4,4,4-trifluorobutoxy)benzoyl)oxy]phenyl}acrylate
3-(2,4-Diaminophenyl)propyl (2E)3-{4-[(4-(4,4,5,5,5-pentafluoropentoxy)benzoyl)oxy]phenyl}acrylate
3-(2,4-Diaminophenyl)propyl (2E)3-{4-[(4-(1,1,2,2-tetrafluoroethoxy)benzoyl)oxy]phenyl}acrylate
3-(2,4-Diaminophenyl)propyl (2E)3-{4-[(4-(4,4,4-trifluorobutanoyl)oxy)benzoyl]oxy}phenyl}acrylate
6-(2,4-Diaminophenyl)hexyl (2E)3-{4-[(4-(4,4,4-trifluorobutoxy)benzoyl)oxy]phenyl}acrylate
6-(2,4-Diaminophenyl)hexyl (2E)3-{4-[(4-(4,4,5,5,5-pentafluoropentoxy)benzoyl)oxy]phenyl}acrylate
6-(2,4-Diaminophenyl)hexyl (2E)3-{4-[(4-(1,1,2,2-tetrafluoroethoxy)benzoyl)oxy]phenyl}acrylate

EXAMPLE 5

Synthesis

Preparation of 2,2-bis(4-aminobenzyl)-1,3 di[(2E)-3-{4-[(4-(4,4,4-trifluorobutoxy)benzoyl)oxy]phenyl}prop-2-enoyl] propanediol

5.1 Preparation of 2,2-dimethyl-5,5-bis(4-nitrobenzyl)-1,3-dioxane-4,6-dione

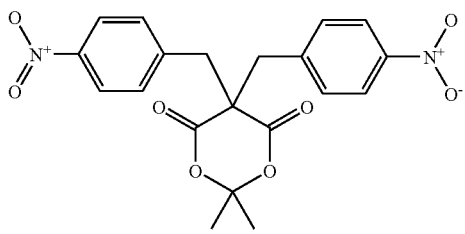

15.0 g (69.4 mmol) of 4-nitrobenzylbromide and 5.00 g (34.7 mmol) of Meldrum's acid are dissolved in 100 ml 2-butanone. 4.40 g (104.1 mmol) potassium carbonate are added, the resulting suspension is heated to 50° C. and allowed to react for 2.5 hours. After cooling to room temperature, 100 ml water are added. The product is collected by filtration and washed with a lot of water. 12.3 g (85%) of 2,2-dimethyl-5,5-bis(4-nitrobenzyl)-1,3-dioxane-4,6-dione as yellowish powder is used without further purification.

5.2 Preparation of 2,2-bis(4-nitrobenzyl)malonic acid

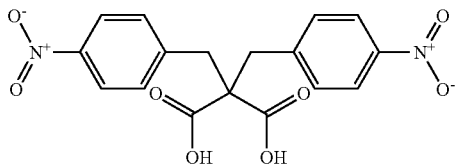

2.185 g (52.07 mmol) of lithium hydroxide are added to a suspension of 10.79 g (26.04 mmol) of 2,2-dimethyl-5,5-bis(4-nitrobenzyl)-1,3-dioxane-4,6-dione and 110 ml mixture of tetrahydrofurane:water 9:1. The mixture is subsequently allowed to react for 21.5 hours at 25° C., added to 500 ml water and acidified to pH=1 with 20 ml hydrochloric acid 3N. The mixture is partitioned between water and ethyl acetate; the organic phase is washed repeatedly with water, dried over sodium sulfate, filtered and concentrated by rotary evaporation. The residue 9.54 g (98%) of 2,2-bis(4-nitrobenzyl)malonic acid as white powder is used without further purification.

5.3 Preparation of 2,2-bis(4-nitrobenzyl)-1,3-propandiol

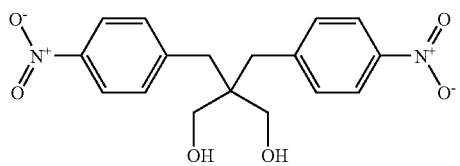

4.00 g (10.69 mmol) 2,2-bis(4-nitrobenzyl)malonic acid are dissolved in 40 ml tetrahydrofuran and added dropwise in a the course of 2 hours to 64.1 ml (64.1 mmol) of a borane-tetrahydrofuran complex 1.0 M solution in tetrahydrofuran. After 19 hours at 25° C., 50 ml water are carefully added. The reaction mixture is then partitioned between ethyl acetate and water; the organic phase is washed repeatedly with water, dried over sodium sulfate, filtered and concentrated by rotary evaporation. The residue, 3.77 g (97%) of 2,2-bis(4-nitrobenzyl)-1,3-propandiol as white powder is used without further purification.

5.4 Preparation 2,2-bis(4-nitrobenzyl)-1,3 di[(2E)-3-{4-[(4-(4,4,4-trifluorobutoxy)benzoyl)oxy]phenyl}prop-2-enoyl] propanediol

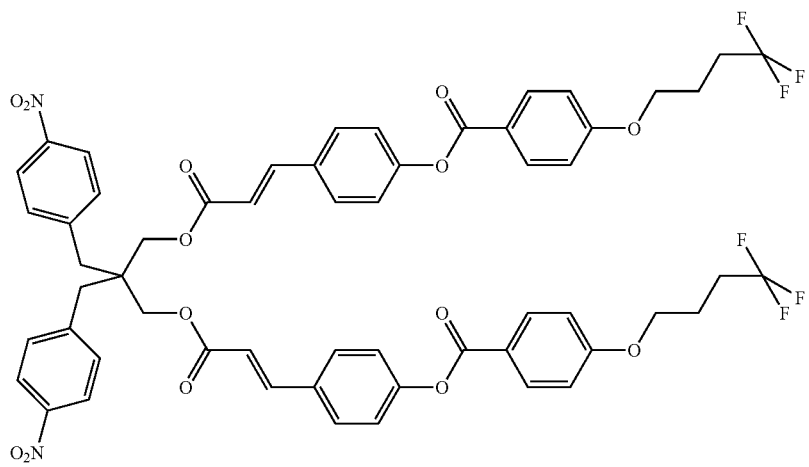

1.76 g (5.07 mmol) of 2,2-bis(4-nitrobenzyl)-1,3-propandiol, 4.00 g (10.14 mmol) of (2E)-3-(4-{[4-(4,4,4-trifluorobutoxy)benzoyl]oxy}phenyl)acrylic acid, 124 mg (1.01 mmol) of 4-Dimethylaminopyridine are dissolved in 100 ml of dichloromethane. 2.14 g (11.16 mmol) of N-(3-Dimethylaminopropyl)-N'-ethylcarbodiimide hydrochloride (EDC hydrochloride) are added at 0° C. The solution is stirred for 1 h at 0° C. and allowed to stir at room temperature overnight. After 22 hours at room temperature the reaction mixture is partitioned between dichloromethane and water. The organic phase is washed repeatedly with water, dried over sodium sulphate, filtered and concentrated by rotary evaporation. Chromatography of the residue on 150 g silica gel using toluene:ethyl acetate 9:1 as eluant to yield 2.20 g 2,2-bis(4-nitrobenzyl)-1,3 di[(2E)-3-{4-[(4-(4,4,4-trifluorobutoxy)benzoyl)oxy]phenyl}prop-2-enoyl] propanediol as white crystals.

5.5 Preparation of 2,2-bis(4-aminobenzyl)-1,3 di[(2E)-3-{4-[(4-(4,4,4-trifluorobutoxy)benzoyl)oxy]phenyl}prop-2-enoyl] propanediol

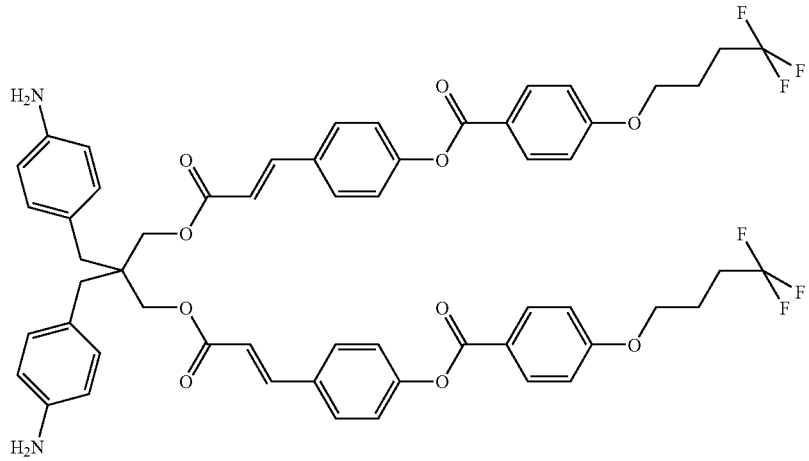

2.20 g (2.00 mol) of 2,2-bis(4-nitrobenzyl)-1,3 di[(2E)-3-{4-[(4-(4,4,4-trifluorobutoxy)benzoyl)oxy]phenyl}prop-2-enoyl] propanediol are dissolved in a mixture of 25 ml of N,N-dimethylformamide and 3 ml water. 3.25 g (12.01 mmol) ferric chloride hexahydrate are added. 1.31 g (20.02 mmol) Zinc powder are added portionwise within 40 min. The mixture is allowed to react for 2 hours. The reaction mixture is then partitioned between ethyl acetate and water and filtered. The organic phase is washed repeatedly with water, dried over sodium sulfate, filtered and concentrated by rotary evaporation. Chromatography of the residue on 100 g silica gel using toluene:ethyl acetate 1:1 as eluant and crystallization form ethylacetate:hexane mixture to yield 1.20 g 2,2-bis(4-aminobenzyl)-1,3 di[(2E)-3-{4-[(4-(4,4,4-trifluorobutoxy)benzoyl)oxy]phenyl}prop-2-enoyl] propanediol The following diamines are synthesized in an analogous manner:

2,2-bis(4-aminobenzyl)-1,3 di[(2E)3-{4-[(4-trifluoromethoxybenzoyl)oxy]phenyl}prop-2-enoyl] propanediol
2,2-bis(4-aminobenzyl)-1,3 di[(2E)3-{4-[(4-(2,2,2-trifluoroethoxy)benzoyl)oxy]phenyl}prop-2-enoyl] propanediol
2,2-bis(4-aminobenzyl)-1,3 di[(2E)3-{4-[(4-(4,4,4-trifluorobutoxy)benzoyl)oxy]phenyl}prop-2-enoyl] propanediol
2,2-bis(4-aminobenzyl)-1,3 di[(2E)3-{4-[(4-(5,5,5-trifluoropentyloxy)benzoyl)oxy]phenyl}prop-2-enoyl] propanediol
2,2-bis(4-aminobenzyl)-1,3 di[(2E)3-{4-[(4-(4,4,5,5,5-pentafluoropentoxy)benzoyl)oxy]phenyl}prop-2-enoyl] propanediol
2,2-bis(4-aminobenzyl)-1,3 di[(2E)3-{4-[(4-(1,1,2,2-tetrafluoroethoxy)benzoyl)oxy]phenyl}prop-2-enoyl] propanediol
2,2-bis(4-aminobenzyl)-1,3 di[(2E)3-{4-[(4-(4,4,4-trifluorobutanoyl)oxy)benzoyl]oxy}phenyl}prop-2-enoyl] propanediol
2,2-bis(4-aminobenzyl)-1,3 di[(2E)3-{4-[(3-methoxy-4-trifluoromethoxybenzoyl)oxy]phenyl}prop-2-enoyl] propanediol
2,2-bis(4-aminobenzyl)-1,3 di[(2E)3-{4-[(3-methoxy 4-(2,2,2-trifluoroethoxy)benzoyl)oxy]phenyl}prop-2-enoyl] propanediol
2,2-bis(4-aminobenzyl)-1,3 di[(2E)3-{4-[(3-methoxy 4-(4,4,4-trifluorobutoxy)benzoyl)oxy]phenyl}prop-2-enoyl] propanediol
2,2-bis(4-aminobenzyl)-1,3 di[(2E)3-{4-[(3-methoxy 4-(5,5,5-trifluoropentyloxy)benzoyl)oxy]phenyl}prop-2-enoyl] propanediol
2,2-bis(4-aminobenzyl)-1,3 di[(2E)3-{4-[(3-methoxy 4-(4,4,5,5,5-pentafluoropentoxy)benzoyl)oxy]phenyl}prop-2-enoyl] propanediol
2,2-bis(4-aminobenzyl)-1,3 di[(2E)3-{4-[(3-methoxy 4-(1,1,2,2-tetrafluoroethoxy)benzoyl)oxy]phenyl}prop-2-enoyl] propanediol
2,2-bis(4-aminobenzyl)-1,3 di[(2E)3-{4-[(3-methoxy 4-(4,4,4-trifluorobutanoyl)oxy)benzoyl]oxy}phenyl}prop-2-enoyl] propanediol
2,2-bis(4-aminobenzyl)-1,3 di[(2E)3-{4-[(4-trifluoromethoxybenzoyl)oxy]-3-methoxyphenyl}prop-2-enoyl] propanediol
2,2-bis(4-aminobenzyl)-1,3 di[(2E)3-{4-[(4-(2,2,2-trifluoroethoxy)benzoyl)oxy]-3-methoxyphenyl}prop-2-enoyl] propanediol
2,2-bis(4-aminobenzyl)-1,3 di[(2E)3-{4-[(4-(4,4,4-trifluorobutoxy)benzoyl)oxy]-3-methoxy phenyl}prop-2-enoyl] propanediol
2,2-bis(4-aminobenzyl)-1,3 di[(2E)3-{4-[(4-(5,5,5-trifluoropentyloxy)benzoyl)oxy]-3-methoxyphenyl}prop-2-enoyl] propanediol
2,2-bis(4-aminobenzyl)-1,3 di[(2E)3-{4-[(4-(4,4,5,5,5-pentafluoropentoxy)benzoyl)oxy]-3-methoxyphenyl}prop-2-enoyl] propanediol
2,2-bis(4-aminobenzyl)-1,3 di[(2E)3-{4-[(4-(1,1,2,2-tetrafluoroethoxy)benzoyl)oxy]-3-methoxyphenyl}prop-2-enoyl] propanediol 2,2-bis(4-aminobenzyl)-1,3 di[(2E)3-{4-[(4-(4,4,4-trifluorobutanoyl)oxy)benzoyl]oxy}-3-methoxyphenyl}prop-2-enoyl] propanediol 2,2-bis(4-aminobenzyl)-1,3 di[(2E)3-{4-[(4-trifluoromethoxyphenoxy)carbonyl]phenyl}prop-2-enoyl] propanediol 2,2-bis(4-aminobenzyl)-1,3 di[(2E)3-{4-[(4-(2,2,2-trifluoroethoxy)phenoxy)carbonyl]phenyl}prop-2-enoyl] propanediol 2,2-bis(4-aminobenzyl)-1,3 di[(2E)3-{4-[(4-(4,4,4-trifluorobutoxy)phenoxy)carbonyl]phenyl}prop-2-enoyl] propanediol 2,2-bis(4-aminobenzyl)-1,3 di[(2E)3-{4-[(4-(5,5,5-trifluoropentyloxy)phenoxy)carbonyl]phenyl}prop-2-enoyl] propanediol 2,2-bis(4-aminobenzyl)-1,3 di[(2E)3-{4-[(4-(4,4,5,5,5-pentafluoropentoxy)phenoxy)carbonyl]phenyl}prop-2-enoyl] propanediol 2,2-bis(4-aminobenzyl)-1,3 di[(2E)3-{4-[(4-(1,1,2,2-tetrafluoroethoxy)phenoxy)carbonyl]phenyl}prop-2-enoyl] propanediol 6.50 g (11.67 mmol) of 6-hydroxyhexyl 4-(6-hydroxyhexyloxy)-3,5-dinitrobenzoate, 9.67 g (24.53 mmol) of (2E)-3-(4-{[4-(4,4,4-trifluorobutoxy)benzoyl]oxy}phenyl)acrylic acid, 290 mg (2.34 mmol) of 4-Dimethylaminopyridine are dissolved in 100 ml of dichloromethane. 5.14 g (26.87 mmol) of N-(3-Dimethylaminopropyl)-N'-ethylcarbodiimide hydrochloride (EDC hydrochloride) are added at 0° C. The solution is stirred for 1 h at 0° C. and allowed to stir at room temperature overnight. After 22 hours at room temperature the reaction mixture is partitioned between dichloromethane and water. The organic phase is washed repeatedly with water, dried over sodium sulphate, filtered and concentrated by rotary evaporation. Chromatography of the residue on 500 g silica gel using toluene:ethyl acetate 95:5 as eluant and crystallization form ethyl acetate:hexane mixture to yield 7.70 g of 6-{[((2E)-3-{4-[(4-(4,4,4-trifluorobutoxy)benzoyl)oxy]phenyl}prop-2-enoyl)oxy]}hexyl 3,5-dinitro-4-[6-{[((2E)-3-{4-[(4-(4,4,4-trifluorobutoxy)benzoyl)oxy]phenyl}prop-2-enoyl)oxy]}hexyloxy]benzoate as yellow crystals 6.2 Preparation of 6-{[((2E)-3-{4-[(4-(4,4,4-trifluorobutoxy)benzoyl)oxy]phenyl}prop-2-enoyl)oxy]}hexyl 3,5-Diamino-4-[6-{[((2E)-3-{4-[(4-(4,4,4-trifluorobutoxy)benzoyl)oxy]phenyl}prop-2-enoyl)oxy]}hexyloxy]benzoate

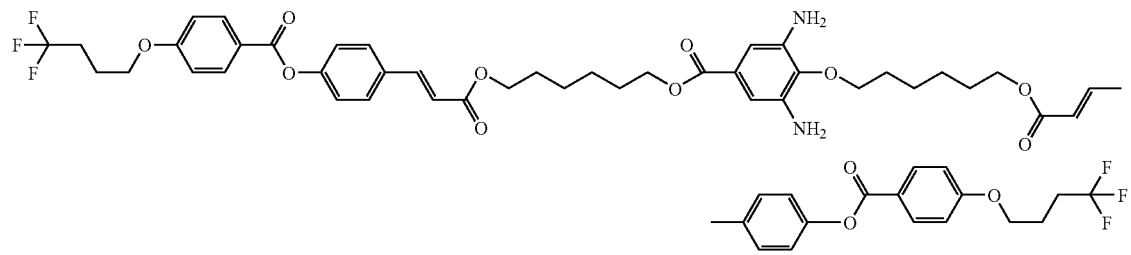

EXAMPLE 6

Synthesis

Preparation of 6-{[((2E)-3-{4-[(4-(4,4,4-trifluorobutoxy)benzoyl)oxy]phenyl}prop-2-enoyl)oxy]}hexyl 3,5-Diamino-4-[6-{[((2E)-3-{4-[(4-(4,4,4-trifluorobutoxy)benzoyl)oxy]phenyl}prop-2-enoyl)oxy]}hexyloxy]benzoate 6.1 Preparation of 6-{[((2E)-3-{4-[(4-(4,4,4-trifluorobutoxy)benzoyl)oxy]phenyl}prop-2-enoyl)oxy]}hexyl 3,5-dinitro-4-[6-{[((2E)-3-{4-[(4-(4,4,4-trifluorobutoxy)benzoyl)oxy]phenyl}prop-2-enoyl)oxy]}hexyloxy]benzoate 7.70 g (6.5 mol) of 6-{[((2E)-3-{4-[(4-(4,4,4-trifluorobutoxy)benzoyl)oxy]phenyl}prop-2-enoyl)oxy]}hexyl 3,5-dinitro-4-[6-{[((2E)-3-{4-[(4-(4,4,4-trifluorobutoxy)benzoyl)oxy]phenyl}prop-2-enoyl)oxy]}hexyloxy]benzoate are dissolved in a mixture of 90 ml of N,N-dimethylformamide and 7 ml water. 10.6 g (39.2 mmol) ferric chloride hexahydrate are added. 4.27 g (65.36 mmol) Zinc powder are added portionwise within 40 min. The mixture is allowed to react for 2 hours. The reaction mixture is then partitioned between ethyl acetate and water and filtered. The organic phase is washed repeatedly with water, dried over sodium sulfate, filtered and concentrated by rotary evaporation. Chromatography of the residue on 200 g silica gel using toluene:ethyl acetate 2:1 as eluant and crystallization form methanol:

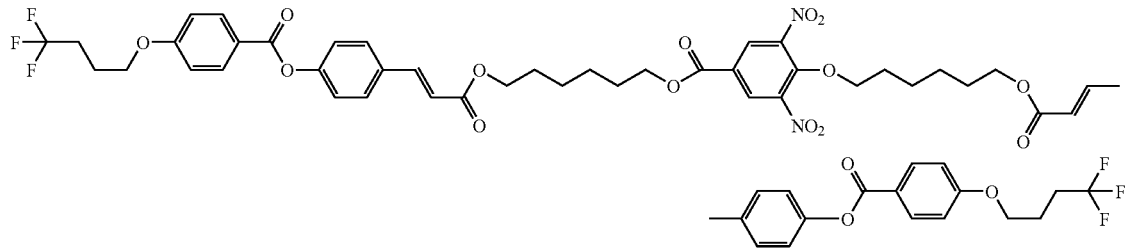

ethyl acetate mixture to yield 4.92 g 6-{[((2E)-3-{4-[(4-(4,4,4-trifluorobutoxy)benzoyl)oxy]phenyl}prop-2-enoyl)oxy]}hexyl 3,5-Diamino-4-[6-{[((2E)-3-{4-[(4-(4,4,4-trifluorobutoxy)benzoyl)oxy]phenyl}prop-2-enoyl)oxy]}hexyloxy]benzoate as colorless crystals.

EXAMPLE 7

Synthesis 7.1 Preparation of 4,4'-Dinitro-1,1'-biphenyl-2,2'-dicarboxylic acid

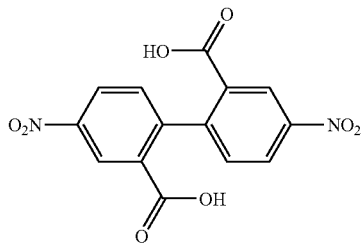

30.0 g (120.13 mmol) Diphenic acid are dissolved at room temperature in 469 g (4.59 mol) concentrated sulfuric acid (96%). The solution is cooled to −15° C. and a mixture of 92.4 g (1.011 mol) concentrated nitric acid (69%) and 12.0 g (0.117 mol) concentrated sulfuric acid (96%) is added slowly so that the mixture temperature is maintained below 0° C. After the addition the solution is allowed to react at room temperature for 24 h. After the mixture is poured onto crushed ice, the precipitate that formed i collected by filtration, washed with water and dried at room temperature under vacuum for 10 h.

7.2 Preparation of 2,2'-bis(hydroxymethyl-4,4'-Dinitro 1,1'-biphenyl

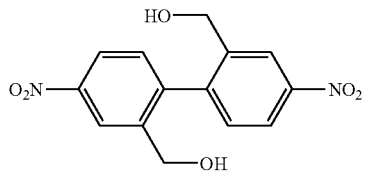

3.6 g (10.83 mmol) 4,4'-Dinitro-1,1'-biphenyl-2,2'-dicarboxylic acid are dissolved in 25 ml tetrahydrofuran and added dropwise in a the course of 1 hours to 65 ml (65.02 mmol) of a borane-tetrahydrofuran complex 1.0 M solution in tetrahydrofuran. After 19 hours at 25° C., 50 ml water are carefully added. After 1 h the solution is acidified to pH=1-2 with 10 ml 1N HCl solution and allowed to stirred for 30 min. The reaction mixture is then partitioned between ethyl acetate and water; the organic phase is washed repeatedly with water, dried over sodium sulfate, filtered and concentrated by rotary evaporation. The residue, 4.2 g of 2,2'-bis(hydroxymethyl-4,4'-Dinitro 1,1'-biphenyl as white powder is used without further purification.

7.3 Preparation of 2,2'-bis[(2E)-3-{4-[(4-(4,4,4-trifluorobutoxy)benzoyl)oxy]phenyl}prop-2-enoyl]methyl 4,4'-Dinitro 1,1'-biphenyl 3.92 g (12.8 mmol) of 2,2'-bis(hydroxymethyl-4,4'-Dinitro 1,1'-biphenyl, 13.20 g (33.5 mmol) of (2E)-3-(4-{[4-(4,4,4-trifluorobutoxy)benzoyl]oxy}phenyl)acrylic acid prepared according to example 1, 0.630 mg (5.15 mmol) of 4-Dimethylaminopyridine are dissolved in 200 ml of dichloromethane. 6.91 g (11.16 mmol) of N,N'-dicyclohexylcarbodiimide are added at 0° C. The solution is stirred for 2 h at 0° C. and allowed to stir at room temperature overnight. After 22 hours at room temperature the reaction mixture is partitioned between dichloromethane and water. The organic phase is washed repeatedly with water, dried over sodium sulphate, filtered and concentrated by rotary evaporation. Chromatography of the residue on 150 g silica gel using toluene:ethyl acetate 9:1 as eluant to yield 12.0 g 2,2'-bis[(2E)-3-{4-[(4-(4,4,4-trifluorobutoxy)benzoyl)oxy]phenyl}prop-2-enoyl]methyl 4,4'-Dinitro 1,1'-biphenyl as white crystals.

7.4 Preparation 2,2'-bis[(2E)-3-{4-[(4-(4,4,4-trifluorobutoxy)benzoyl)oxy]phenyl}prop-2-enoyl]methyl 4,4'-Diamino 1,1'-biphenyl

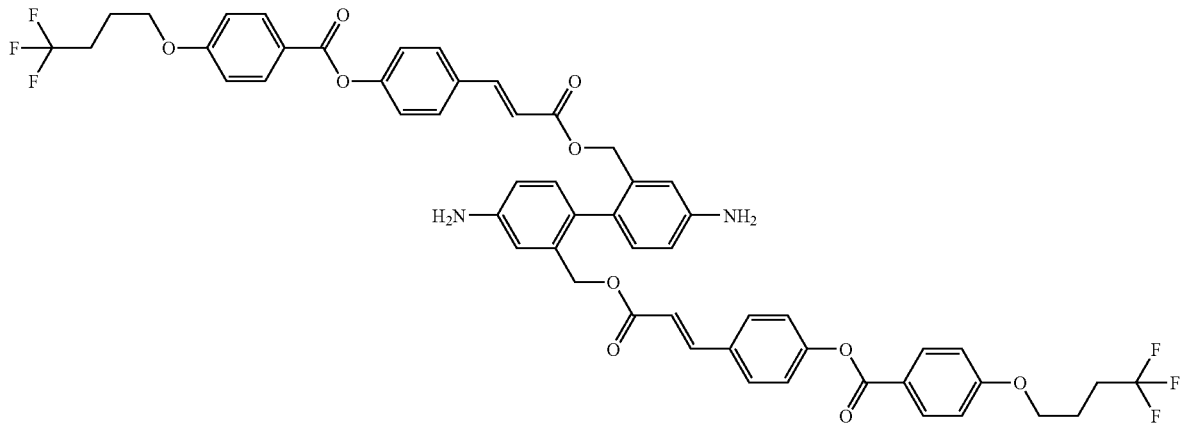

2.27 g (2.14 mol) of 2,2'-bis[(2E)-3-{4-[(4-(4,4,4-trifluorobutoxy)benzoyl)oxy]phenyl}prop-2-enoyl]methyl 4,4'-Dinitro 1,1'-biphenyl are dissolved in a mixture of 40 ml of N,N-dimethylformamide and 3 ml water. 3.48 g (12.8 mmol) ferric chloride hexahydrate are added. 1.40 g (21.4 mmol) Zinc powder are added portionwise within 40 min. The mixture is allowed to react for 2 hours. The reaction mixture is then partitioned between ethyl acetate and water and filtered. The organic phase is washed repeatedly with water, dried over sodium sulfate, filtered and concentrated by rotary evaporation. Chromatography of the residue on 100 g silica gel using toluene:ethyl acetate 7:3 as eluant yield 1.74 g 2,2'-bis[(2E)-3-{4-[(4-(4,4,4-trifluorobutoxy)benzoyl)oxy]phenyl}prop-2-enoyl]methyl 4,4'-Diamino 1,1'-biphenyl as yellowish crystals.

2,2'-bis[(2E)3-{4-[(4-(4,4,5,5,5-pentafluoropentoxy)benzoyl)oxy]phenyl}prop-2-enoyl]methyl 4,4'-diamino 1,1'-biphenyl is prepared analogous to example 7 using (2E)3-{4-[(4-(4,4,5,5,5-pentafluoropentyloxy)benzoyl)oxy]phenyl}acrylic acid.

The following diamines are synthesized in an analogous manner:

2,2'-bis[(2E)3-{4-[(4-trifluoromethoxybenzoyl)oxy]phenyl}prop-2-enoyl]methyl 4,4'-diamino 1,1'-biphenyl
2,2'-bis[(2E)3-{4-[(4-(2,2,2-trifluoroethoxy)benzoyl)oxy]phenyl}prop-2-enoyl]methyl 4,4'-diamino 1,1'-biphenyl
2,2'-bis[(2E)3-{4-[(4-(4,4,4-trifluorobutoxy)benzoyl)oxy]phenyl}prop-2-enoyl]methyl 4,4'-diamino 1,1'-biphenyl
2,2'-bis[(2E)3-{4-[(4-(5,5,5-trifluoropentyloxy)benzoyl)oxy]phenyl}prop-2-enoyl]methyl 4,4'-diamino 1,1'-biphenyl
2,2'-bis[(2E)3-{4-[(4-(1,1,2,2-tetrafluoroethoxy)benzoyl)oxy]phenyl}prop-2-enoyl]methyl 4,4'-diamino 1,1'-biphenyl
2,2'-bis[(2E)3-{4-[(4-(4,4,4-trifluorobutanoyl)oxy)benzoyl]oxy}phenyl]prop-2-enoyl]methyl 4,4'-diamino 1,1'-biphenyl
2,2'-bis[(2E)3-{4-[(3-methoxy-4-trifluoromethoxybenzoyl)oxy]phenyl}prop-2-enoyl]methyl 4,4'-diamino 1,1'-biphenyl
2,2'-bis[(2E)3-{4-[(3-methoxy 4-(2,2,2-trifluoroethoxy)benzoyl)oxy]phenyl}prop-2-enoyl]methyl 4,4'-diamino 1,1'-biphenyl
2,2'-bis[(2E)3-{4-[(3-methoxy 4-(4,4,4-trifluorobutoxy)benzoyl)oxy]phenyl}prop-2-enoyl]methyl 4,4'-diamino 1,1'-biphenyl
2,2'-bis[(2E)3-{4-[(3-methoxy 4-(5,5,5-trifluoropentyloxy)benzoyl)oxy]phenyl}prop-2-enoyl]methyl 4,4'-diamino 1,1'-biphenyl
2,2'-bis[(2E)3-{4-[(3-methoxy 4-(4,4,5,5,5-pentafluoropentoxy)benzoyl)oxy]phenyl}prop-2-enoyl]methyl 4,4'-diamino 1,1'-biphenyl
2,2'-bis[(2E)3-{4-[(3-methoxy 4-(1,1,2,2-tetrafluoroethoxy)benzoyl)oxy]phenyl}prop-2-enoyl]methyl 4,4'-diamino 1,1'-biphenyl
2,2'-bis[(2E)3-{4-[(3-methoxy 4-(4,4,4-trifluorobutanoyl)oxy)benzoyl]oxy}phenyl]prop-2-enoyl]methyl 4,4'-diamino 1,1'-biphenyl
2,2'-bis[(2E)3-{4-[(4-trifluoromethoxybenzoyl)oxy]-3-methoxyphenyl}prop-2-enoyl]methyl 4,4'-diamino 1,1'-biphenyl
2,2'-bis[(2E)3-{4-[(4-(2,2,2-trifluoroethoxy)benzoyl)oxy]-3-methoxyphenyl}prop-2-enoyl]methyl 4,4'-diamino 1,1'-biphenyl
2,2'-bis[(2E)3-{4-[(4-(4,4,4-trifluorobutoxy)benzoyl)oxy]-3-methoxy phenyl}prop-2-enoyl]methyl 4,4'-diamino 1,1'-biphenyl
2,2'-bis[(2E)3-{4-[(4-(5,5,5-trifluoropentyloxy)benzoyl)oxy]-3-methoxyphenyl}prop-2-enoyl]methyl 4,4'-diamino 1,1'-biphenyl
2,2'-bis[(2E)3-{4-[(4-(4,4,5,5,5-pentafluoropentoxy)benzoyl)oxy]-3-methoxyphenyl}prop-2-enoyl]methyl 4,4'-diamino 1,1'-biphenyl
2,2'-bis[(2E)3-{4-[(4-(1,1,2,2-tetrafluoroethoxy)benzoyl)oxy]-3-methoxyphenyl}prop-2-enoyl]methyl 4,4'-diamino 1,1'-biphenyl
2,2'-bis[(2E)3-{4-[(4-(4,4,4-trifluorobutanoyl)oxy)benzoyl]oxy}-3-methoxyphenyl]prop-2-enoyl]methyl 4,4'-diamino 1,1'-biphenyl
2,2'-bis[(2E)3-{4-[(4-trifluoromethoxyphenoxy)carbonyl]phenyl}prop-2-enoyl]methyl 4,4'-diamino 1,1'-biphenyl 2,2'-bis[(2E)3-{4-[(4-(2,2,2-trifluoroethoxy)phenoxy)carbonyl]phenyl}prop-2-enoyl]methyl 4,4'-diamino 1,1'-biphenyl 2,2'-bis[(2E)3-{4-[(4-(4,4,4-trifluorobutoxy)phenoxy)carbonyl]phenyl}prop-2-enoyl]methyl 4,4'-diamino 1,1'-biphenyl 2,2'-bis[(2E)3-{4-[(4-(5,5,5-trifluoropentyloxy)phenoxy)carbonyl]phenyl}prop-2-enoyl]methyl 4,4'-diamino 1,1'-biphenyl 2,2'-bis[(2E)3-{4-[(4-(4,4,5,5,5-pentafluoropentoxy)phenoxy)carbonyl]phenyl}prop-2-enoyl]methyl 4,4'-diamino 1,1'-biphenyl 2,2'-bis[(2E)3-{4-[(4-(1,1,2,2-tetrafluoroethoxy)phenoxy)carbonyl]phenyl}prop-2-enoyl]methyl 4,4'-diamino 1,1'-biphenyl

EXAMPLE 8

Synthesis

Preparation of 2-(2,4-Diaminophenyl)-1,3 di[(2E)-3-{4-[(4-(4,4,4-trifluorobutoxy)benzoyl)oxy]phenyl}prop-2-enoyl] propanediol 8.1 Preparation of 2-(2,4-Dinitrophenyl)-1,3 di[(2E)-3-{4-[(4-(4,4,4-trifluorobutoxy)benzoyl)oxy]phenyl}prop-2-enoyl] propanediol

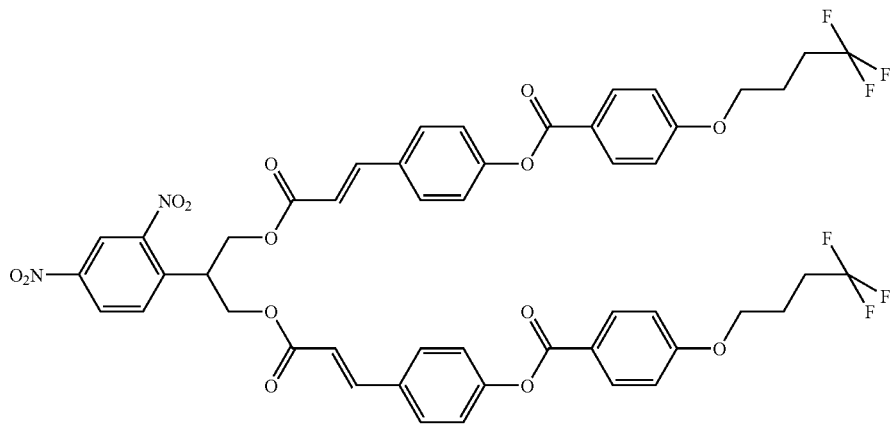

2.90 g (12.0 mmol) of 2-(4-nitrophenyl)-1,3-propandiol, 9.54 g (24.2 mmol) of (2E)-3-(4-{[4-(4,4,4-trifluorobutoxy)benzoyl]oxy}phenyl)acrylic acid. 296 mg (2.42 mmol) of 4-Dimethylaminopyridine are dissolved in 100 ml of dichloromethane. 9.20 g (49.0 mmol) of N-(3-Dimethylaminopropyl)-N'-ethylcarbodiimide hydrochloride (EDC hydrochloride) are added at 0° C. The solution is stirred for 1 h at 0° C. and allowed to stir at room temperature overnight. After 22 hours at room temperature the reaction mixture is partitioned between dichloromethane and water. The organic phase is washed repeatedly with water, dried over sodium sulphate, filtered and concentrated by rotary evaporation. Chromatography of the residue on 600 g silica gel using toluene:ethyl acetate 9:1 as eluant to yield 7.60 g 2-(4-nitrophenyl)-1,3 di[(2E)-3-{4-[(4-(4,4,4-trifluorobutoxy)benzoyl)oxy]phenyl}prop-2-enoyl] propanediol as white crystals.

8.2 Preparation of 2-(2,4-Diaminophenyl)-1,3 di[(2E)-3-{4-[(4-(4,4,4-trifluorobutoxy)benzoyl)oxy]phenyl}prop-2-enoyl] propanediol

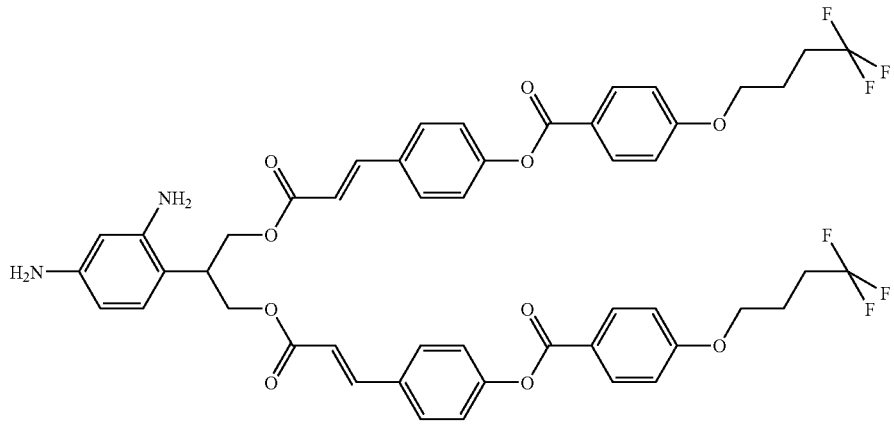

7.60 g (7.64 mmol) of 2-(4-nitrophenyl)-1,3 di[(2E)-3-{4-[(4-(4,4,4-trifluorobutoxy)benzoyl)oxy]phenyl}prop-2-enoyl] propanediol are dissolved in a mixture of 45 ml of N,N-dimethylformamide and 5 ml water. 12.39 g (45.84 mmol) ferric chloride hexahydrate are added. 4.99 g (76.4 mmol) Zinc powder are added portionwise within 40 min. The mixture is allowed to react for 2 hours. The reaction mixture is then partitioned between ethyl acetate and water and filtered. The organic phase is washed repeatedly with water, dried over sodium sulfate, filtered and concentrated by rotary evaporation. Chromatography of the residue on 1000 g silica gel using toluene:ethyl acetate 1:1 as eluant and crystallization form ethylacetate:hexane mixture to yield 4.30 g of 2-(2,4-Diaminophenyl)-1,3 di[(2E)-3-{4-[(4-(4,4,4-trifluorobutoxy)benzoyl)oxy]phenyl}prop-2-enoyl] propanediol.

The following diamines are synthesized in an analogous manner:

2-(2,4-Diaminophenyl)-1,3 di[(2E)3-{4-[(4-trifluoromethoxybenzoyl)oxy]phenyl}prop-2-enoyl] propanediol 2-(2,4-Diaminophenyl)-1,3 di[(2E)3-{4-[(4-(2,2,2-trifluoroethoxy)benzoyl)oxy]phenyl}prop-2-enoyl] propanediol 2-(2,4-Diaminophenyl)-1,3 di[(2E)3-{4-[(4-(4,4,4-trifluorobutoxy)benzoyl)oxy]phenyl}prop-2-enoyl] propanediol 2-(2,4-Diaminophenyl)-1,3 di[(2E)3-{4-[(4-(5,5,5-trifluoropentyloxy)benzoyl)oxy]phenyl}prop-2-enoyl] propanediol 2-(2,4-Diaminophenyl)-1,3 di[(2E)3-{4-[(4-(4,4,5,5,5-pentafluoropentoxy)benzoyl)oxy]phenyl}prop-2-enoyl] propanediol 2-(2,4-Diaminophenyl)-1,3 di[(2E)3-{4-[(4-(1,1,2,2-tetrafluoroethoxy)benzoyl)oxy]phenyl}prop-2-enoyl] propanediol 2-(2,4-Diaminophenyl)-1,3 di[(2E)3-{4-[(4-(4,4,4-trifluorobutanoyl)oxy)benzoyl]oxy}phenyl}prop-2-enoyl] propanediol 2-(2,4-Diaminophenyl)-1,3 di[(2E)3-{4-[(3-methoxy-4-trifluoromethoxybenzoyl)oxy]phenyl}prop-2-enoyl] propanediol 2-(2,4-Diaminophenyl)-1,3 di[(2E)3-{4-[(3-methoxy 4-(2,2,2-trifluoroethoxy)benzoyl)oxy]phenyl}prop-2-enoyl] propanediol 2-(2,4-Diaminophenyl)-1,3 di[(2E)3-{4-[(3-methoxy 4-(4,4,4-trifluorobutoxy)benzoyl)oxy]phenyl}prop-2-enoyl] propanediol 2-(2,4-Diaminophenyl)-1,3 di[(2E)3-{4-[(3-methoxy 4-(5,5,5-trifluoropentyloxy)benzoyl)oxy]phenyl}prop-2-enoyl] propanediol 2-(2,4-Diaminophenyl)-1,3 di[(2E)3-{4-[(3-methoxy 4-(4,4,5,5,5-pentafluoropentoxy)benzoyl)oxy]phenyl}prop-2-enoyl] propanediol 2-(2,4-Diaminophenyl)-1,3 di[(2E)3-{4-[(3-methoxy 4-(1,1,2,2-tetrafluoroethoxy)benzoyl)oxy]phenyl}prop-2-enoyl] propanediol 2-(2,4-Diaminophenyl)-1,3 di[(2E)3-{4-[(3-methoxy 4-(4,4,4-trifluorobutanoyl)oxy)benzoyl]oxy}phenyl}prop-2-enoyl] propanediol 2-(2,4-Diaminophenyl)-1,3 di[(2E)3-{4-[(4-trifluoromethoxybenzoyl)oxy]-3-methoxyphenyl}prop-2-enoyl] propanediol 2-(2,4-Diaminophenyl)-1,3 di[(2E)3-{4-[(4-(2,2,2-trifluoroethoxy)benzoyl)oxy]-3-methoxyphenyl}prop-2-enoyl] propanediol 2-(2,4-Diaminophenyl)-1,3 di[(2E)3-{4-[(4-(4,4,4-trifluorobutoxy)benzoyl)oxy]-3-methoxy phenyl}prop-2-enoyl] propanediol 2-(2,4-Diaminophenyl)-1,3 di[(2E)3-{4-[(4-(5,5,5-trifluoropentyloxy)benzoyl)oxy]-3-methoxyphenyl}prop-2-enoyl] propanediol 2-(2,4-Diaminophenyl)-1,3 di[(2E)3-{4-[(4-(4,4,5,5,5-pentafluoropentoxy)benzoyl)oxy]-3-methoxyphenyl}prop-2-enoyl] propanediol 2-(2,4-Diaminophenyl)-1,3 di[(2E)3-{4-[(4-(1,1,2,2-tetrafluoroethoxy)benzoyl)oxy]-3-methoxyphenyl}prop-2-enoyl] propanediol 2-(2,4-Diaminophenyl)-1,3 di[(2E)3-{4-[(4-(4,4,4-trifluorobutanoyl)oxy)benzoyl]oxy}-3-methoxyphenyl}prop-2-enoyl] propanediol 2-(2,4-Diaminophenyl)-1,3 di[(2E)3-{4-[(4-trifluoromethoxyphenoxy)carbonyl]phenyl}prop-2-enoyl] propanediol 2-(2,4-Diaminophenyl)-1,3 di[(2E)3-{4-[(4-(2,2,2-trifluoroethoxy)phenoxy)carbonyl]phenyl}prop-2-enoyl] propanediol 2-(2,4-Diaminophenyl)-1,3 di[(2E)3-{4-[(4-(4,4,4-trifluorobutoxy)phenoxy)carbonyl]phenyl}prop-2-enoyl] propanediol 2-(2,4-Diaminophenyl)-1,3 di[(2E)3-{4-[(4-(5,5,5-trifluoropentyloxy)phenoxy)carbonyl]phenyl}prop-2-enoyl] propanediol 2-(2,4-Diaminophenyl)-1,3 di[(2E)3-{4-[(4-(4,4,5,5,5-pentafluoropentoxy)phenoxy)carbonyl]phenyl}prop-2-enoyl] propanediol 2-(2,4-Diaminophenyl)-1,3 di[(2E)3-{4-[(4-(1,1,2,2-tetrafluoroethoxy)phenoxy)carbonyl]phenyl}prop-2-enoyl] propanediol 2-(3,5-Diaminophenyl)-1,3 di[(2E)3-{4-[(4-trifluoromethoxybenzoyl)oxy]phenyl}prop-2-enoyl] propanediol 2-(3,5-Diaminophenyl)-1,3 di[(2E)3-{4-[(4-(2,2,2-trifluoroethoxy)benzoyl)oxy]phenyl}prop-2-enoyl] propanediol 2-(3,5-Diaminophenyl)-1,3 di[(2E)3-{4-[(4-(4,4,4-trifluorobutoxy)benzoyl)oxy]phenyl}prop-2-enoyl] propanediol 2-(3,5-Diaminophenyl)-1,3 di[(2E)3-{4-[(4-(5,5,5-trifluoropentyloxy)benzoyl)oxy]phenyl}prop-2-enoyl] propanediol 2-(3,5-Diaminophenyl)-1,3 di[(2E)3-{4-[(4-(4,4,5,5,5-pentafluoropentoxy)benzoyl)oxy]phenyl}prop-2-enoyl] propanediol 2-(3,5-Diaminophenyl)-1,3 di[(2E)3-{4-[(4-(1,1,2,2-tetrafluoroethoxy)benzoyl)oxy]phenyl}prop-2-enoyl] propanediol 2-(3,5-Diaminophenyl)-1,3 di[(2E)3-{4-[(4-(4,4,4-trifluorobutanoyl)oxy)benzoyl]oxy}phenyl}prop-2-enoyl] propanediol 2-(3,5-Diaminophenyl)-1,3 di[(2E)3-{4-[(3-methoxy-4-trifluoromethoxybenzoyl)oxy]phenyl}prop-2-enoyl] propanediol 2-(3,5-Diaminophenyl)-1,3 di[(2E)3-{4-[(3-methoxy 4-(2,2,2-trifluoroethoxy)benzoyl)oxy]phenyl}prop-2-enoyl] propanediol 2-(3,5-Diaminophenyl)-1,3 di[(2E)3-{4-[(3-methoxy 4-(4,4,4-trifluorobutoxy)benzoyl)oxy]phenyl}prop-2-enoyl] propanediol 2-(3,5-Diaminophenyl)-1,3 di[(2E)3-{4-[(3-methoxy 4-(5,5,5-trifluoropentyloxy)benzoyl)oxy]phenyl}prop-2-enoyl] propanediol 2-(3,5-Diaminophenyl)-1,3 di[(2E)3-{4-[(3-methoxy 4-(4,4,5,5,5-pentafluoropentoxy)benzoyl)oxy]phenyl}prop-2-enoyl] propanediol 2-(3,5-Diaminophenyl)-1,3 di[(2E)3-{4-[(3-methoxy 4-(1,1,2,2-tetrafluoroethoxy)benzoyl)oxy]phenyl}prop-2-enoyl] propanediol 2-(3,5-Diaminophenyl)-1,3 di[(2E)3-{4-[(3-methoxy 4-(4,4,4-trifluorobutanoyl)oxy)benzoyl]oxy}phenyl}prop-2-enoyl] propanediol 2-(3,5-Diaminophenyl)-1,3 di[(2E)3-{4-[(4-trifluoromethoxybenzoyl)oxy]-3-methoxyphenyl}prop-2-enoyl] propanediol 2-(3,5-Diaminophenyl)-1,3 di[(2E)3-{4-[(4-(2,2,2-trifluoroethoxy)benzoyl)oxy]-3-methoxyphenyl}prop-2-enoyl] propanediol 2-(3,5-Diaminophenyl)-1,3 di[(2E)3-{4-[(4-(4,4,4-trifluorobutoxy)benzoyl)oxy]-3-methoxy phenyl}prop-2-enoyl] propanediol 2-(3,5-Diaminophenyl)-1,3 di[(2E)3-{4-[(4-(5,5,5-trifluoropentyloxy)benzoyl)oxy]-3-methoxyphenyl}prop-2-enoyl] propanediol 2-(3,5-Diaminophenyl)-1,3 di[(2E)3-{4-[(4-(4,4,5,5,5-pentafluoropentoxy)benzoyl)oxy]-3-methoxyphenyl}prop-2-enoyl] propanediol 2-(3,5-Diaminophenyl)-1,3 di[(2E)3-{4-[(4-(1,1,2,2-tetrafluoroethoxy)benzoyl)oxy]-3-methoxyphenyl}prop-2-enoyl] propanediol 2-(3,5-Diaminophenyl)-1,3 di[(2E)3-{4-[(4-(4,4,4-trifluorobutanoyl)oxy)benzoyl]oxy}-3-methoxyphenyl}prop-2-enoyl] propanediol 2-(3,5-Diaminophenyl)-1,3 di[(2E)3-{4-[(4-trifluoromethoxyphenoxy)carbonyl]phenyl}prop-2-enoyl] propanediol 2-(3,5-Diaminophenyl)-1,3 di[(2E)3-{4-[(4-(2,2,2-trifluoroethoxy)phenoxy)carbonyl]phenyl}prop-2-enoyl] propanediol 2-(3,5-Diaminophenyl)-1,3 di[(2E)3-{4-[(4-(4,4,4-trifluorobutoxy)phenoxy)carbonyl]phenyl}prop-2-enoyl] propanediol 2-(3,5-Diaminophenyl)-1,3 di[(2E)3-{4-[(4-(5,5,5-trifluoropentyloxy)phenoxy)carbonyl]phenyl}prop-2-enoyl] propanediol 2-(3,5-Diaminophenyl)-1,3 di[(2E)3-{4-[(4-(4,4,5,5,5-pentafluoropentoxy)phenoxy)carbonyl]phenyl}prop-2-enoyl] propanediol 2-(3,5-Diaminophenyl)-1,3 di[(2E)3-{4-[(4-(1,1,2,2-tetrafluoroethoxy)phenoxy)carbonyl]phenyl}prop-2-enoyl] propanediol

EXAMPLE 9

Polymersiation Step A (Formation of the Polyamic Acid)

2.25 g (11.47 mmol) of 1,2,3,4-cyclobutantetracarboxylic acid dianhydride is added to a solution of 8.030 g (12.77 mmol) of 6-{[((2E)-3-{4-[(4-(4,4,4-trifluorobutoxy)benzoyl)oxy]phenyl}prop-2-enoyl)oxy]}hexyl 3,5-Diaminobenzoate in 56.0 ml of tetrahydrofuran. Stirring is then carried out at 0° C. for 2 hours. Then another 0.255 g (1.30 mmol) of 1,2,3,4-cyclobutantetracarboxylic acid dianhydride are added. The mixture is subsequently allowed to react for 21 hours at room temperature. The polymer mixture is diluted with 56 ml THF, precipitated into 2000 ml diethyl ether and collected by filtration. The polymer is reprecipitated form THF (160 ml) into 3500 ml water to yield, after drying at room temperature under vacuum, 9.42 g of Polyamic Acid 1 in the from of a white powder; [η]=0.50 dL/g Analogous to EXAMPLE 9 the following diamines are used for the preparation of Polyamic Acid with 1,2,3,4-cyclobutantetracarboxylic acid dianhydride 6-{[((2E)-3-{4-[(4-(3,3,3-trifluoropropoxy)benzoyl)oxy]phenyl}prop-2-enoyl)oxy]}hexyl 3,5-Diaminobenzoate

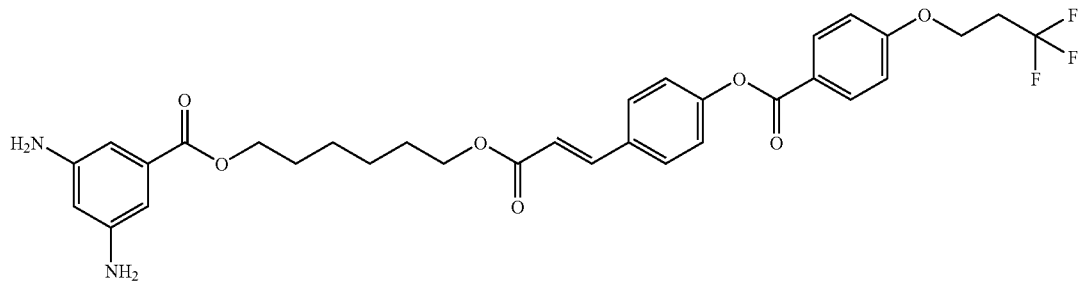

yield Polyamic acid 2 as white powder; [η]=0.24 dL/g.

6-{[((2E)-3-{4-[(3-methoxy 4-(4,4,4-trifluorobutoxy)benzoyl)oxy]phenyl}prop-2-enoyl)oxy]}hexyl 3,5-Diaminobenzoate

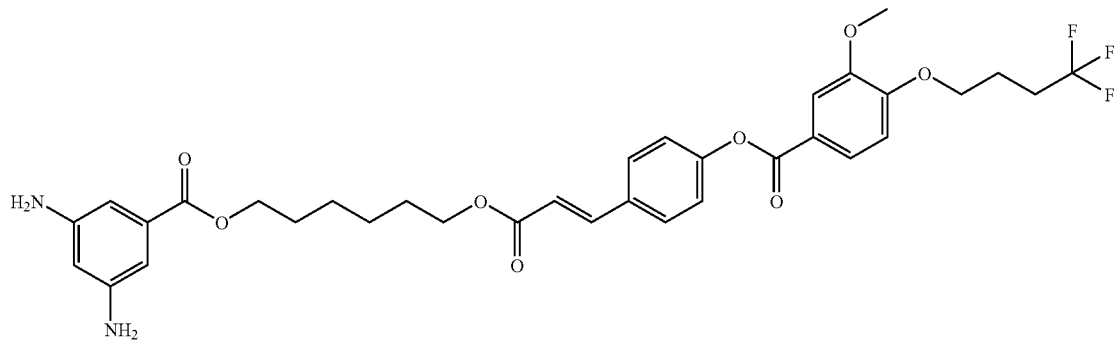

yield Polyamic acid 3 as white powder; [η]=0.25 dL/g.

8-{[((2E)-3-{4-[(4-(4,4,4-trifluorobutoxy)benzoyl)oxy]phenyl}prop-2-enoyl)oxy]}octyl 3,5-Diaminobenzoate

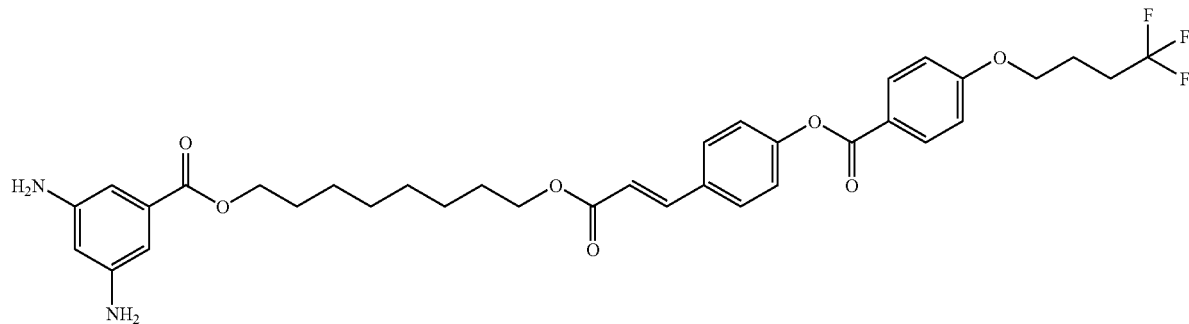

yield Polyamic acid 4 as white powder; [η]=1.09 dL/g.

4-{[((2E)-3-{4-[(4-(4,4,4-trifluorobutoxy)benzoyl)oxy]phenyl}prop-2-enoyl)oxy]}butyl 3,5-Diaminobenzoate

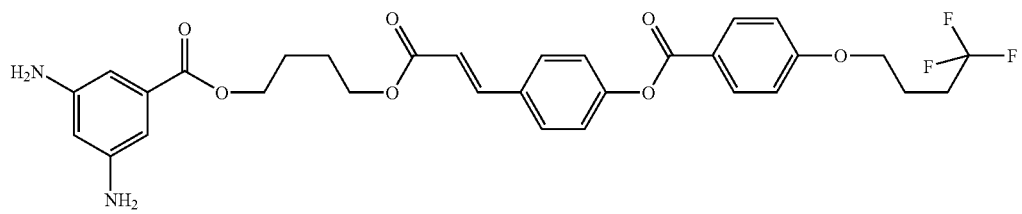

yield Polyamic acid 5 as white powder; [η]=0.21 dL/g.

2-[2-{[((2E)-3-{4-[(4-(4,4,4-trifluorobutoxy)benzoyl)oxy]phenyl}prop-2-enoyl)oxy]}ethoxy]ethyl 3,5-Diaminobenzoate

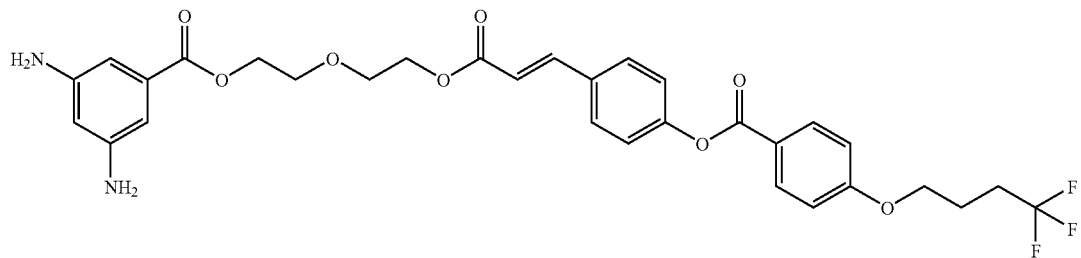

yield Polyamic acid 6 as white powder; [η]=0.87 dL/g.

2-{[((2E)-3-{4-[(4-(4,4,4-trifluorobutoxy)benzoyl)oxy]phenyl}prop-2-enoyl)oxy]}ethyl 3,5-Diaminobenzoate

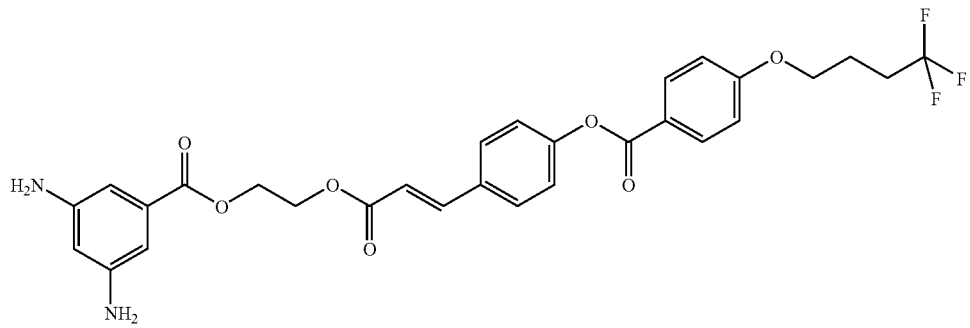

yield Polyamic acid 7 as white powder; [η]=0.48 dL/g.

3-{[((2E)-3-{4-[(4-(4,4,4-trifluorobutoxy)benzoyl)oxy]phenyl}prop-2-enoyl)oxy]}propyl 3,5-Diaminobenzoate yield

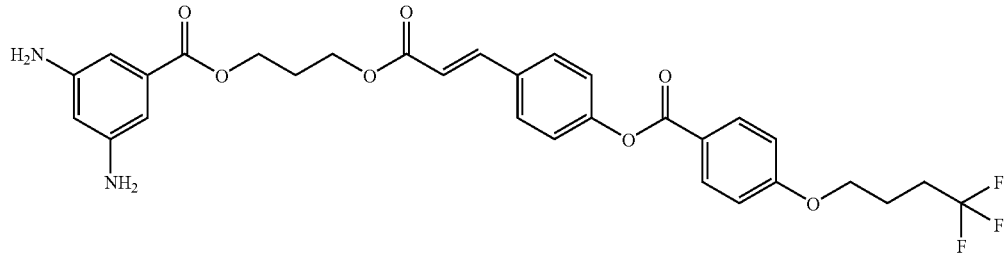

Polyamic acid 8 as white powder; [η]=0.63 dL/g.

6-{[((2E)-3-{4-[(4-(4,4,5,5,5-pentafluoropentoxy)benzoyl)oxy]phenyl}prop-2-enoyl)oxy]}hexyl 3,5-Diaminobenzoate

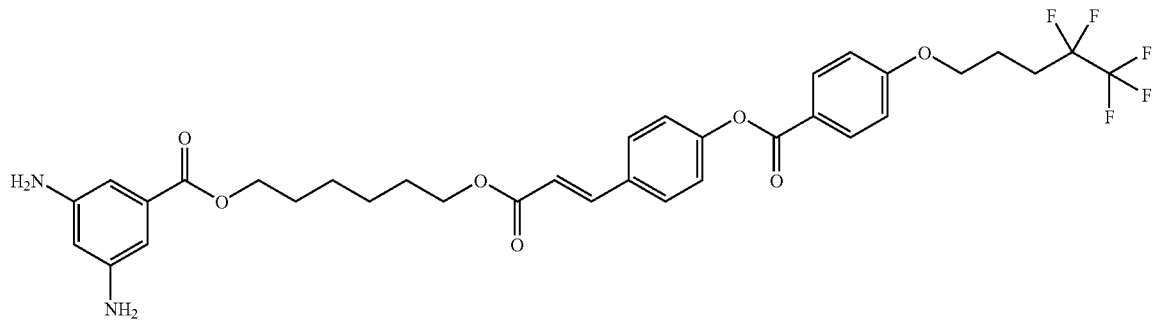

yield Polyamic acid 9 as white powder; [η]=0.26 dL/g.

6-{[((2E)-3-{4-[(4-trifluoromethoxybenzoyl)oxy]phenyl}prop-2-enoyl)oxy]}hexyl 3,5-Diaminobenzoate

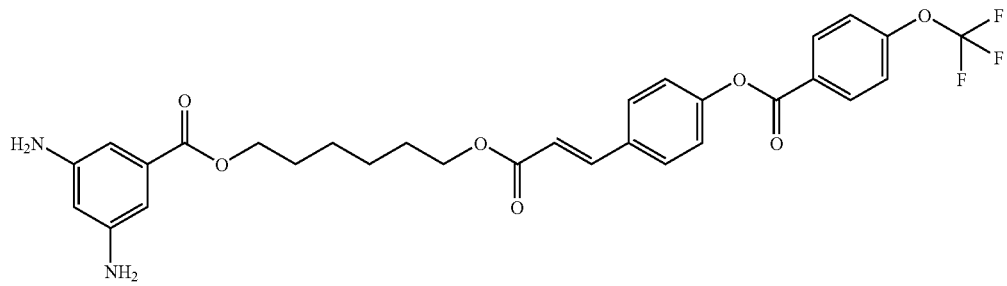

yield Polyamic acid 10 as white powder; [η]=0.71 dL/g

6-{[((2E)-3-{4-[(4-trifluoromethylbenzoyl)oxy]phenyl}prop-2-enoyl)oxy]}hexyl 3,5-Diaminobenzoate

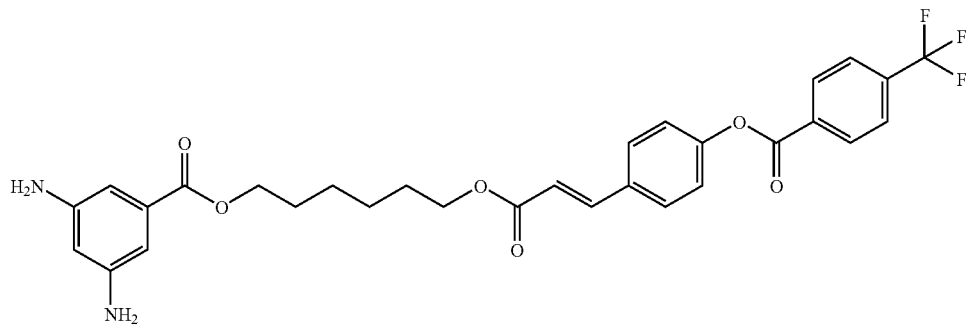

yield Polyamic acid 11 as white powder; [η]=1.21 dL/g

6-{[((2E)-3-{4-[(4-(2,2,3,3-tetrafluoropropoxy)benzoyl)oxy]phenyl}prop-2-enoyl)oxy]}hexyl 3,5-Diaminobenzoate
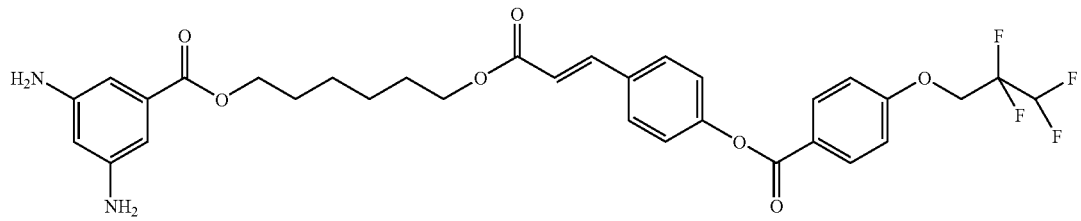
yield Polyamic acid 12 as white powder; [η]=0.48 dL/g
6-{[((2E)-3-{4-[(4-(2,2,3,3-tetrafluoroethoxy)benzoyl)oxy]phenyl}prop-2-enoyl)oxy]}hexyl 3,5-Diaminobenzoate
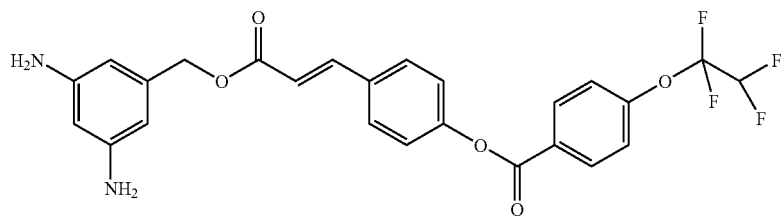
yield Polyamic acid 13 as white powder; [η]=0.48 dL/g
3,5-Diaminobenzyl (2E)3-{4-[(4-(4,4,5,5,5-pentafluoropentyloxy)benzoyl)oxy]phenyl}acrylate
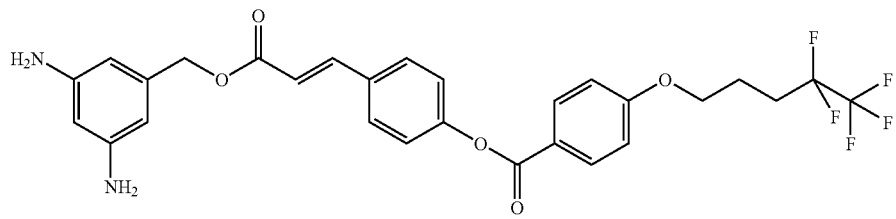
yield Polyamic acid 14 as white powder; [η]=0.59 dL/g 3,5-Diaminobenzyl (2E)3-{4-[(4-(4,4,5,5,6,6,6-heptafluorohexyloxy)benzoyl)oxy]phenyl}acrylate

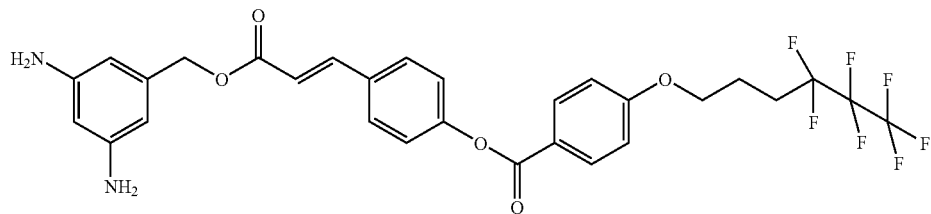

yield Polyamic acid 15 as white powder; [η]=0.20 dL/g 3,5-Diaminobenzyl (2E)3-{4-[(4-(5,5,5-trifluorobutoxy)benzoyl)oxy]phenyl}acrylate

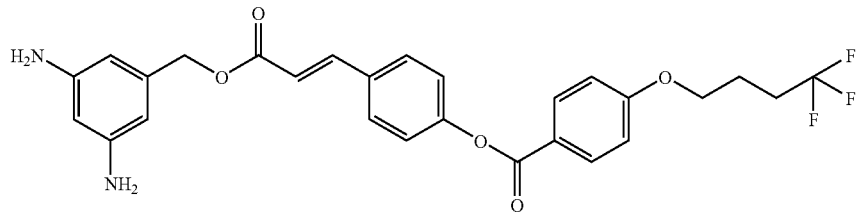

yield Polyamic acid 16 as white powder; [η]=0.38 dL/g 2-(2,4-Diaminophenyl)ethyl (2E)3-{4-[(4-(4,4,4-trifluorobutoxy)benzoyl)oxy]phenyl}acrylate

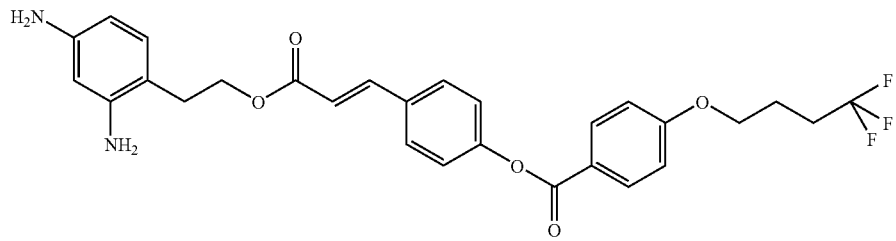

yield Polyamic acid 17 as white powder; [η]=0.50 dL/g 2-(2,4-Diaminophenyl)ethyl (2E)3-{4-[(4-(4,4,5,5,5-pentafluoropentyloxy)benzoyl)oxy]phenyl}acrylate

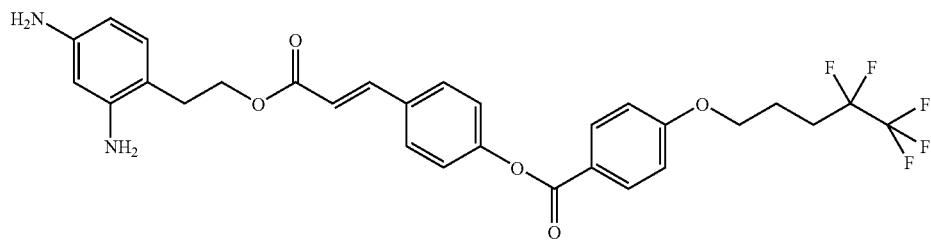

yield Polyamic acid 18 as white powder; [η]=0.27 dL/g 2-(2,4-Diaminophenyl)ethyl (2E)3-{4-[(4-(4,4,5,5,6,6,6-heptafluorohexyloxy)benzoyl)oxy]phenyl}acrylate
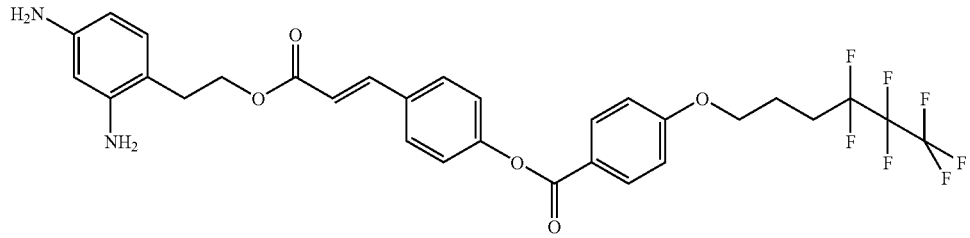
yield Polyamic acid 19 as white powder; [η]=0.19 dL/g
2-(2,4-Diaminophenyl)ethyl (2E)3-{4-[(4-(2,2,3,3-tetrafluoroethoxy)benzoyl)oxy]phenyl}acrylate
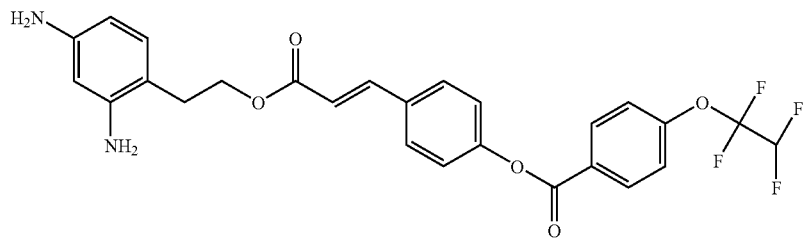
yield Polyamic acid 20 as white powder; [η]=0.28 dL/g
2,2-bis(4-aminobenzyl)-1,3 di[(2E)-3-{4-[(4-(4,4,4-trifluorobutoxy)benzoyl)oxy]phenyl}prop-2-enoyl]propanediol
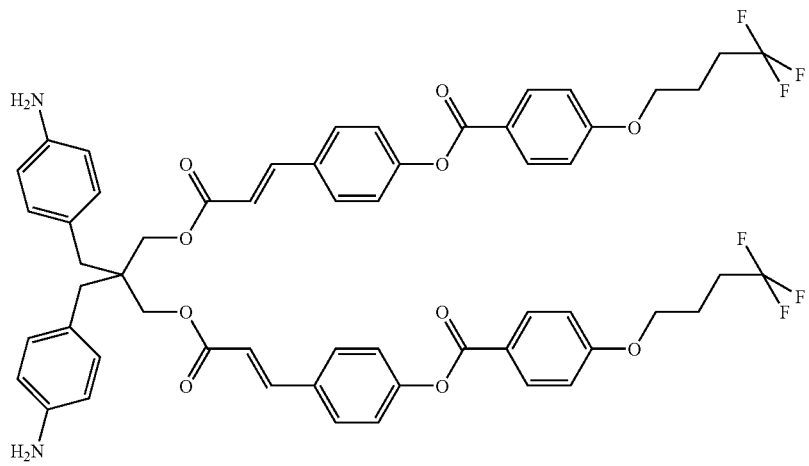
yield Polyamic acid 21 as white powder; [η]=0.54 dL/g 2-(2,4-Dinitrophenyl)-1,3 di[(2E)-3-{4-[(4-(4,4,4-trifluorobutoxy)benzoyl)oxy]phenyl}prop-2-enoyl] propanediol
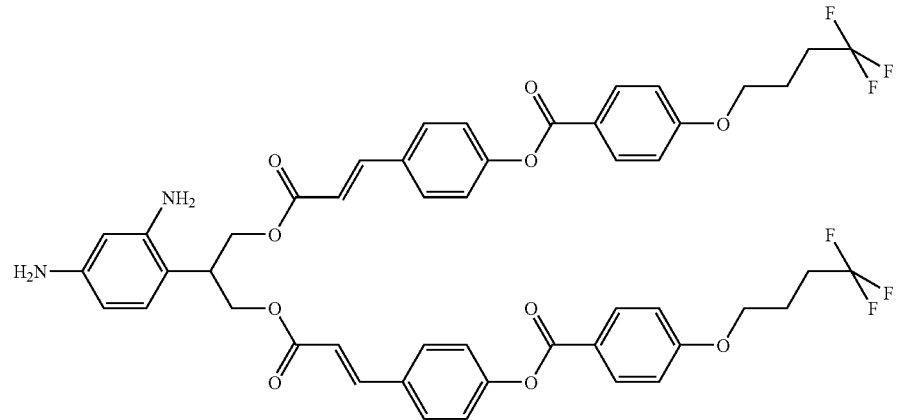
yield Polyamic acid 22 as white powder; [η]=0.17 dL/g
2-(2,4-Dinitrophenyl)-1,3 di[(2E)-3-{4-[(4-(4,4,5,5,5-pentafluoropentyloxy)benzoyl)oxy]phenyl}prop-2-enoyl] propanediol
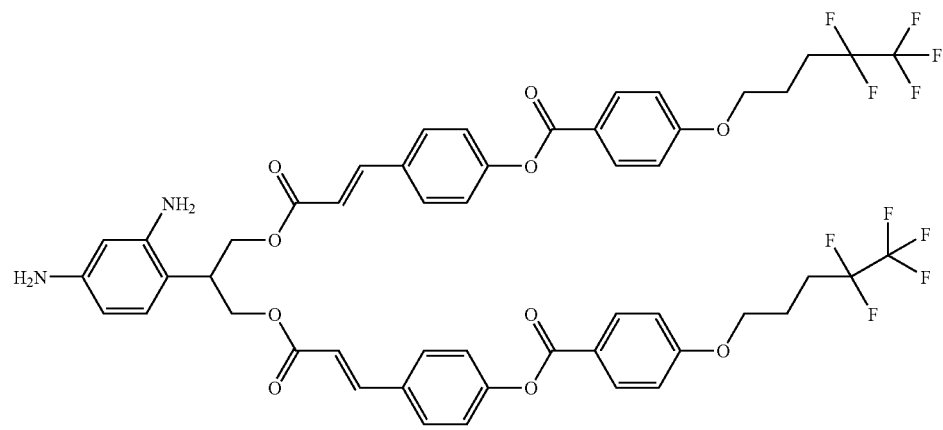
yield Polyamic acid 23 as white powder; [η]=0.16 dL/g 2,2'-bis[(2E)-3-{4-[(4-(4,4,5,5,5-pentafluoropenty-loxy)benzoyl)oxy]phenyl}prop-2-enoyl]methyl 4,4'-Diamino 1,1'-biphenyl

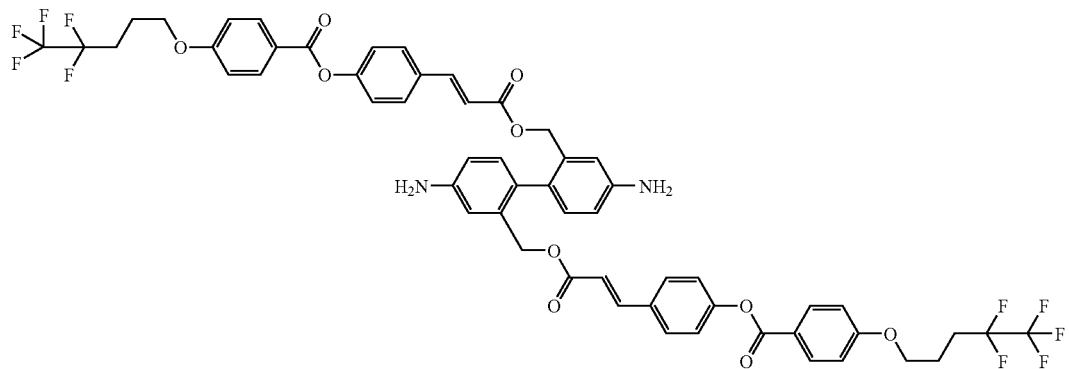

yield Polyamic acid 24 as white powder; [η]=0.55 dL/g

EXAMPLE 10

Analogous to EXAMPLE 9 the following diamines are used for the preparation of Polyamic Acid with 2,3,5-tricarboxycyclopentylacetic acid dianhydride 3,5-Diaminobenzyl (2E)3-{4-[(4-(5,5,5-trifluorobu-toxy)benzoyl)oxy]phenyl}acrylate

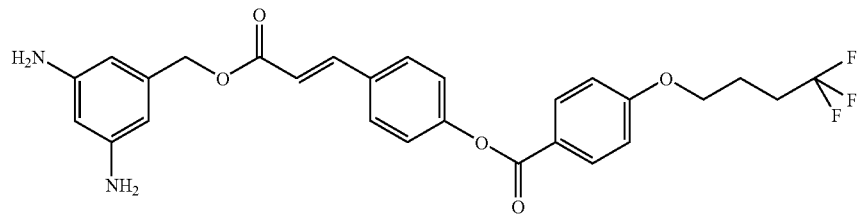

yield Polyamic acid 25 as white powder; [η]=0.40 dL/g 2,2-bis(4-aminobenzyl)-1,3 di[(2E)-3-{4-[(4-(4,4,4-trifluorobutoxy)benzoyl)oxy]phenyl}prop-2-enoyl]propanediol
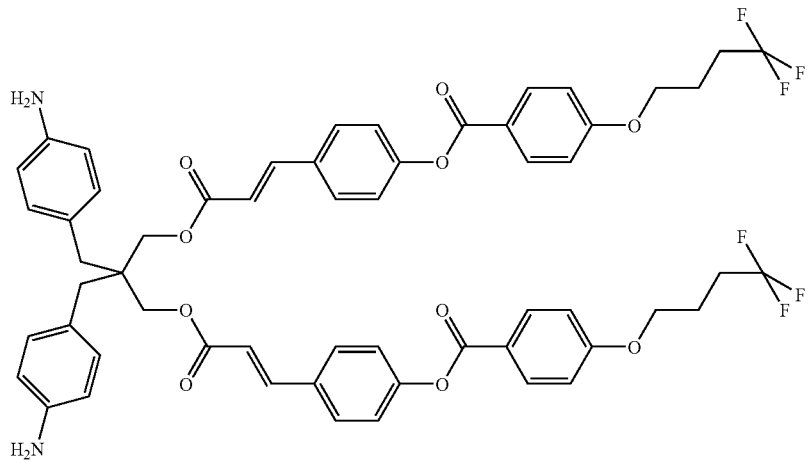
yield Polyamic acid 26 as white powder; [η]=0.47 dL/g
2-(2,4-Diaminophenyl)ethyl (2E)3-{4-[(4-(4,4,4-trifluorobutoxy)benzoyl)oxy]phenyl}acrylate
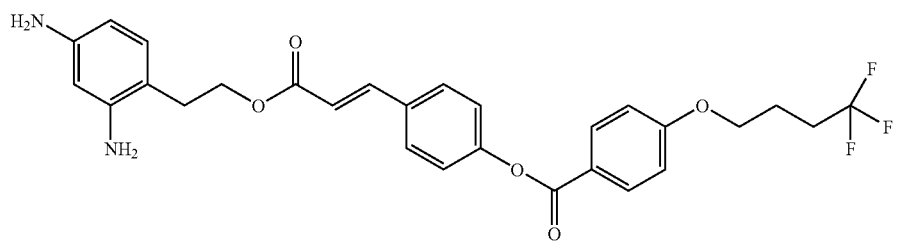
yield Polyamic acid 27 as white powder; [η]=0.23 dL/g
2-(2,4-Diaminophenyl)ethyl (2E)3-{4-[(4-(4,4,5,5,5-pentafluoropentyloxy)benzoyl)oxy]phenyl}acrylate
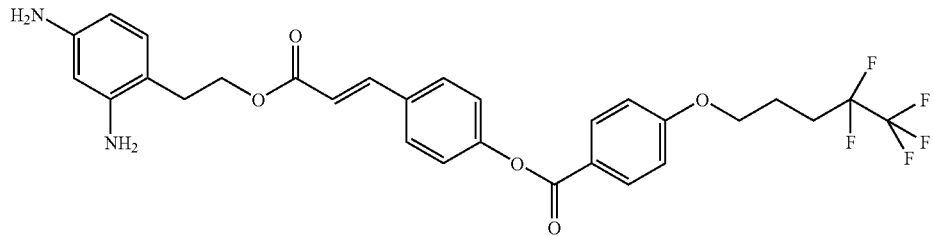
yield Polyamic acid 28 as white powder; [η]=0.14 dL/g 3,5-Diaminobenzyl (2E)3-{4-[(4-(5,5,5-trifluorobutoxy)benzoyl)oxy]phenyl}acrylate

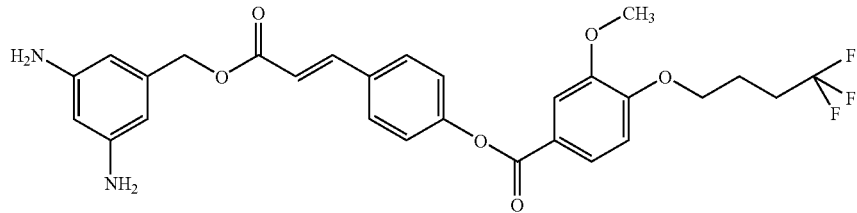

yield Polyamic acid 29 as white powder; [η]=0.45 dL/g 2,2'-bis[(2E)-3-{4-[(4-(4,4,5,5,5-pentafluoropentyloxy)benzoyl)oxy]phenyl}prop-2-enoyl]methyl 4,4'-Diamino 1,1'-biphenyl

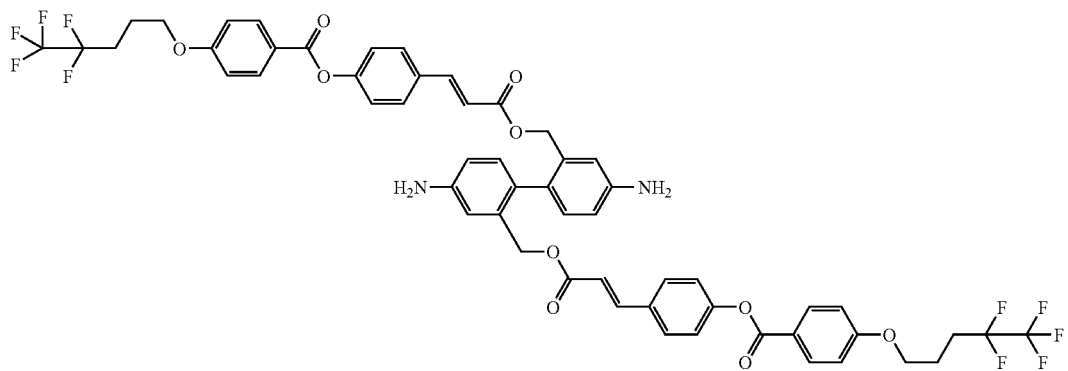

yield Polyamic acid 30 as white powder; [η]=0.30 dL/g 2,2'-bis[(2E)-3-{4-[(4-(4,4,4-trifluorobutoxy)benzoyl)oxy]phenyl}prop-2-enoyl]methyl 4,4'-Diamino 1,1'-biphenyl

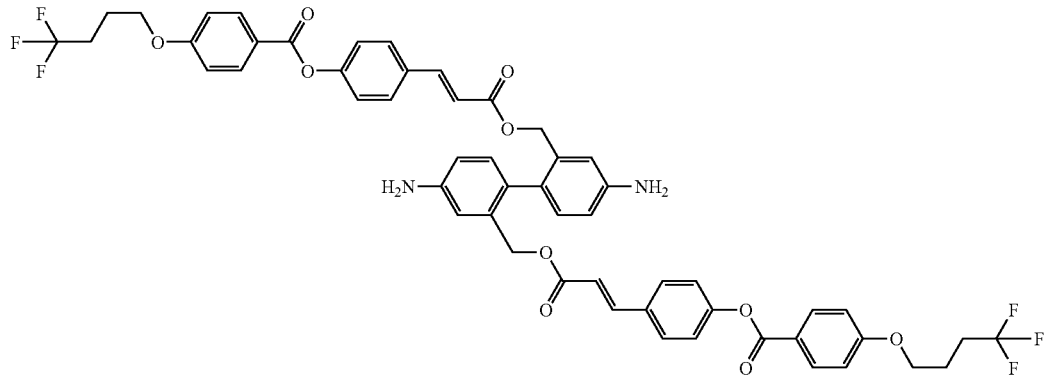

yield Polyamic acid 31 as white powder; [η]=0.17 dL/g 2-(2,4-Dinitrophenyl)-1,3 di[(2E)-3-{4-[(4-(4,4,4-trifluorobutoxy)benzoyl)oxy]phenyl}prop-2-enoyl] propanediol

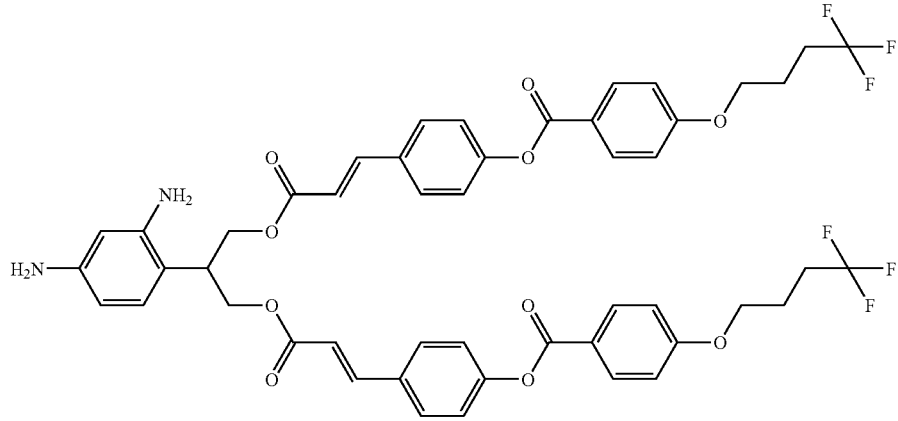

2-(2,4-Dinitrophenyl)-1,3 di[(2E)-3-{4-[(4-(4,4,5,5,5-pentafluoropentyloxy)benzoyl)oxy]phenyl}prop-2-enoyl] propanediol

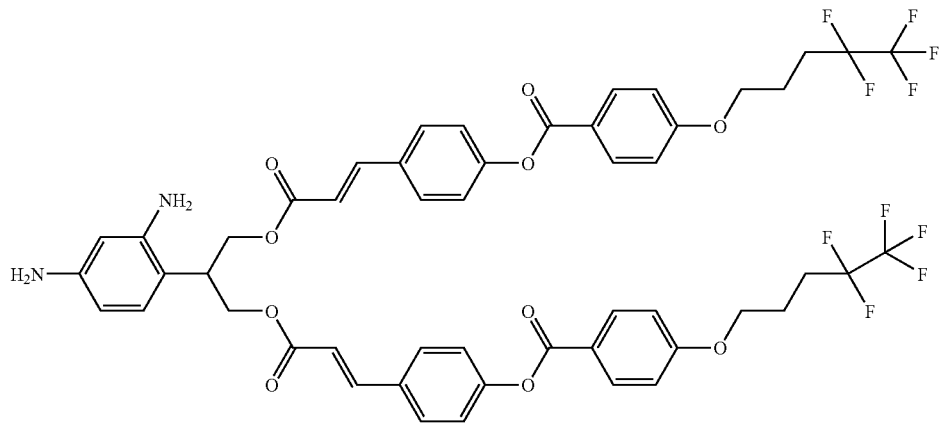

EXAMPLE 11

Analogous to EXAMPLE 9 the following tetracarboxylic acid dianhydride are used for the preparation of Polyamic Acid with of 6-{[((2E)-3-{4-[(4-(4,4,4-trifluorobutoxy)benzoyl)oxy]phenyl}prop-2-enoyl)oxy]}hexyl 3,5-Diaminobenzoate.
4-(2,5-dioxotetrahydrofuran-3-yl)tetrahydronaphthalene-1,2-dicarboxylicacid dianhydride Diaminobenzoate yield Polyamic acid 32 as white powder; [η]=0.15 dL/g.
bicyclo[2.2.2]oct-7-ene-2,3,5,6-tetracarboxylic acid dianhydride yield Polyamic acid 33 as white powder; [η]=0.11 dL/g
2,3,5-tricarboxycyclopentylacetic acid dianhydride yield Polyamic acid 34 as white powder; [η]=0.43 dL/g
5-(2,5-dioxotetrahydrofuran-3-yl)-3-methyl-3-cyclohexene-1,2-dicarboxylic-acid dianhydride yield Polyamic acid 35 as white powder; [η]=0.16 dL/g
4,4'-(hexafluoroisopropylidene)diphthalic acid dianhydride yield Polyamic acid 36 as white powder; [η]=0.51 dL/g

EXAMPLE 12

Analogous to EXAMPLE 9 the following tetracarboxylic acid dianhydride mixture are used for the preparation of Polyamic Acid with of 6-{[((2E)-3-{4-[(4-(4,4,4-trifluorobutoxy)benzoyl)oxy]phenyl}prop-2-enoyl)oxy]}hexyl 3,5-Diaminobenzoate.
A mixture of 1,2,3,4-cyclobutantetracarboxylic acid dianhydride and 4-(2,5-dioxotetrahydrofuran-3-yl)tetrahydronaphthalene-1,2-dicarboxylic acid dianhydride 25:75 (mole ratio) yield Polyamic acid 37 as white powder; [η]=0.16 dL/g
A mixture of 1,2,3,4-cyclobutantetracarboxylic acid dianhydride and 4-(2,5-dioxotetrahydrofuran-3-yl)tetrahydronaphthalene-1,2-dicarboxylic acid dianhydride 1:1 (mole ratio) yield Polyamic acid 38 as white powder; [η]=0.20 dL/g
A mixture of 1,2,3,4-cyclobutantetracarboxylic acid dianhydride and 4-(2,5-dioxotetrahydrofuran-3-yl)tetrahydronaphthalene-1,2-dicarboxylic acid dianhydride 75:25 (mole ratio) yield Polyamic acid 39 as white powder; [η]=0.20 dL/g A mixture of 1,2,3,4-cyclobutantetracarboxylic acid dianhydride and 4-(2,5-dioxotetrahydrofuran-3-yl)tetrahydronaphthalene-1,2-dicarboxylic acid dianhydride 90:10 (mole ratio) yield Polyamic acid 40 as white powder; [η]=0.17 dL/g A mixture of 1,2,3,4-cyclobutantetracarboxylic acid dianhydride and 5-(2,5-dioxotetrahydrofuran-3-yl)-3-methyl-3-cyclohexene-1,2-dicarboxylic-acid dianhydride 25:75 (mole ratio) yield Polyamic acid 41 as white powder; [η]=0.16 dL/g A mixture of 1,2,3,4-cyclobutantetracarboxylic acid dianhydride and 5-(2,5-dioxotetrahydrofuran-3-yl)-3-methyl-3-cyclohexene-1,2-dicarboxylic-acid dianhydride 1:1 (mole ratio) yield Polyamic acid 42 as white powder; [η]=0.16 dL/g A mixture of 1,2,3,4-cyclobutantetracarboxylic acid dianhydride and 5-(2,5-dioxotetrahydrofuran-3-yl)-3-methyl-3-cyclohexene-1,2-dicarboxylic-acid dianhydride 75:25 (mole ratio) yield Polyamic acid 43 as white powder; [η]=0.16 dL/g

EXAMPLE 13

Analogous to EXAMPLE 9 a mixture of 1,2,3,4-cyclobutantetracarboxylic acid dianhydride and 4-(2,5-dioxotetrahydrofuran-3-yl)tetrahydronaphthalene-1,2-dicarboxylic acid dianhydride 75:25 (mole ratio) and 3,5-Diaminobenzyl (2E) 3-{4-[(4-(4,4,5,5,5-pentafluoropentyloxy)benzoyl)oxy]phenyl}acrylate were used for the preparation to yield Polyamic acid 44 as white powder; [η]=0.17 dL/g

EXAMPLE 14

Analogous to EXAMPLE 9 a mixture of 1,2,3,4-cyclobutantetracarboxylic acid dianhydride and 4-(2,5-dioxotetrahydrofuran-3-yl)tetrahydronaphthalene-1,2-dicarboxylic acid dianhydride 75:25 (mole ratio) and 3,5-Diaminobenzyl (2E) 3-{4-[(4-(4,4,4-trifluorobutoxy)benzoyl)oxy]phenyl}acrylate were used for the preparation to yield Polyamic acid 45 as white powder; [η]=0.24 dL/g

EXAMPLE 15

Analogous to EXAMPLE 9 a mixture of 1,2,3,4-cyclobutantetracarboxylic acid dianhydride and 4-(2,5-dioxotetrahydrofuran-3-yl)tetrahydronaphthalene-1,2-dicarboxylic acid dianhydride 75:25 (mole ratio) and 2-(2,4-Diaminophenyl) ethyl (2E)3-{4-[(4-(4,4,5,5,5-pentafluoropentyloxy)benzoyl)oxy]phenyl}acrylate are used for the preparation to yield Polyamic acid 46 as white powder; [η]=0.11 dL/g

EXAMPLE 16

Analogous to EXAMPLE 9 a mixture of 2,2-bis(4-aminobenzyl)-1,3 di[(2E)-3-{4-[(4-(4,4,4-trifluorobutoxy)benzoyl)oxy]phenyl}prop-2-enoyl] propanediol and 6-{[((2E)-3-{4-[(4-(4,4,4-trifluorobutoxy)benzoyl)oxy]phenyl}prop-2-enoyl)oxy]}hexyl 3,5-Diaminobenzoate 1:1 (mole ratio) and 1,2,3,4-cyclobutantetracarboxylic acid dianhydride are used for the preparation to yield Polyamic acid 47 as white powder; [η]=0.98 dL/g

EXAMPLE 17

Analogous to EXAMPLE 9 a mixture of 2,2-bis(4-aminobenzyl)-1,3 di[(2E)-3-{4-[(4-(4,4,4-trifluorobutoxy)benzoyl)oxy]phenyl}prop-2-enoyl] propanediol and 4,4'-Diaminodiphenylmethane 80:20 (mole ratio) and 1,2,3,4-cyclobutantetracarboxylic acid dianhydride are used for the preparation to yield Polyamic acid 48 as white powder; [η]=1.00 dL/g

EXAMPLE 18

Polymerisation Step B (Formation of the Polyimide)

0.50 g of Polyamic Acid No. 1 obtained in above EXAMPLE 9 are dissolved in 3 ml of 1-methyl-2-pyrrolidon (NMP). Thereto are added 0.28 g (3.57 mmol, 4 equivalent) of pyridine and 364 mg (3.57 mmol, 4 equivalent) acetic acid anhydride, and the dehydration and ring closure is carried out at 80° C. for 2 h. The polymer mixture is diluted with 1.5 ml NMP, precipitated into 100 ml diethyl ether and collected by filtration. The polymer is reprecipitated from THF (10 ml) into 200 ml water to yield, after drying at room temperature under vacuum, 0.55 g Polyimide No 1; [η]=0.50 dL/g, Imidization degree ID=100%

Analogous to the polymerization step of EXAMPLE 18 the following polyamic acids are used for the preparation of partially imidizated polyimide. The imidization degree is adjusted with the ratio of acetic acid anhydride and pyridine.

Polyamic acid 1 with 1.2 equivalent acetic acid anhydride and pyridine yield Polyimide 1 as white powder; [η]=0.23 dL/g, ID=40%.

Polyamic acid 1 with 0.8 equivalent acetic acid anhydride and pyridine yield Polyimide 1 as white powder; [η]=0.26 dL/g, ID=30%.

Polyamic acid 1 with 0.4 equivalent acetic acid anhydride and pyridine yield Polyimide 1 as white powder; [η]=0.27 dL/g, ID=14%.

Polyamic acid 2 yield Polyimide 2 as white powder; [η]=0.24 dL/g, ID=100%

Polyamic acid 5 yield Polyimide 5 as white powder; [η]=0.36 dL/g, ID=100%

Polyamic acid 13 yield Polyimide 14 as white powder; [η]=0.88 dL/g, ID=100%

Polyamic acid 14 yield Polyimide 13 as white powder; [η]=0.48 dL/g, ID=100%

Polyamic acid 15 yield Polyimide 15 as white powder; [η]=0.20 dL/g, ID=100%

Polyamic acid 16 yield Polyimide 16 as white powder; [η]=0.27 dL/g, ID=100%

Polyamic acid 17 yield Polyimide 17 as white powder; [η]=0.29 dL/g, ID=100%

Polyamic acid 18 yield Polyimide 18 as white powder; [η]=0.28 dL/g, ID=100%

Polyamic acid 19 yield Polyimide 19 as white powder; [η]=0.19 dL/g, ID=100%

Polyamic acid 20 yield Polyimide 20 as white powder; [η]=0.28 dL/g, ID=100%

Polyamic acid 21 yield Polyimide 21 as white powder; [η]=0.63 dL/g, ID=100%

Polyamic acid 25 yield Polyimide 25 as white powder; [η]=0.43 dL/g, ID=100%

Polyamic acid 27 yield Polyimide 27 as white powder; [η]=0.20 dL/g, ID=100%

Polyamic acid 28 yield Polyimide 28 as white powder; [η]=0.14 dL/g, ID=60%

Polyamic acid 28 with 1.0 equivalent acetic acid anhydride and pyridine yield Polyimide 28 as white powder; [η]=0.23 dL/g, ID=25%.

Polyamic acid 34 yield Polyimide 34 as white powder; [η]=0.40 dL/g, ID=100%

Polyamic acid 39 yield Polyimide 39 as white powder; [η]=0.21 dL/g, ID=100%

Polyamic acid 44 yield Polyimide 44 as white powder; [η]=0.14 dL/g, ID=100%

Polyamic acid 45 yield Polyimide 45 as white powder; [η]=0.12 dL/g, ID=100%

EXAMPLE 19

Preparation of an Orientation Layer for Vertical Alignment with Non-Polarized UV Light A 4% solution of LPP (see molecular structure on figure 1) in a solvent mixture of N-Methyl-2-Pyrrolidone (NMP) and Butylglycol (BC) in a ratio of 1:9 by weight was prepared. This LPP solution was filtered over a 2 μm Teflon filter and applied to two indium tin oxide (ITO) coated rectangular glass plates by spin coating at 1350 rpm for 30 seconds. The resulting films were then pre-dried for 5 minutes at 130° C. and further post-baked for 40 minutes at 200° C. Both ITO covered glass plates were irradiated with non-polarised UV light at a dose of 48 mJ/cm². The direction of incidence of the light being inclined by 10° relative to the plate normal and the incidence plane was parallel to the short side of the substrate. The two irradiated plates were used to build a cell of 20 μm spacing in an anti-parallel manner such that the irradiated surfaces were facing each other. The cell was then capillary filled with liquid crystal mixture MLC6610 from Merck in the isotropic phase at 105° C. The cell was then gradually cooled down at a rate of 0.1° C./min from T=105° C. to T=85° C. and at a rate of 2 C/min from T=85° C. to room temperature. When arranged between crossed polarisers, the cell appeared uniformly black for every angle between the short edge of the cell and the polariser transmission axis, as long as viewed from the vertical. In conclusion, the liquid crystal mixture was aligned homeotropically.

When the short edge of the cell was set at 45° to the polariser axis and an AC voltage of 7V and 90 Hz was applied, the liquid crystals switched and caused the cell to appear green (high order birefringence). No defects or tilt domains were observed. Brightness and colour of the switched cell changed asymmetrically when viewed from opposite, but equal oblique angles along a plane parallel to the short edge of the cell. Contrary, no asymmetry was found when viewed obliquely from opposite angles within a plane parallel to the long edge of the cell. When the switched cell with its short edge was aligned parallel or perpendicular to one of the polariser transmission axes the cell appeared dark again. From above observations we concluded that LC alignment capability was induced in the thin film on the substrate due to irradiation with slantwise incident non-polarized light. The azimuthal alignment direction was parallel to the plane of incidence of the non-polarized uv-light.

From tilt angle evaluation by means of the crystal rotation method a tilt angle value of 89.2° with respect to the substrate surface was obtained. The direction of the LC molecules was in between the surface normal and the direction of the incident light.

EXAMPLE 20

Production of an Orientation Layer Having a Defined Angle of Tilt with Unpolarized UV Light The same type of experiment has been done with the same LPP, except that the direction of incidence of the light was inclined by 40° relative to the plate normal. The azimuthal alignment direction was parallel to the plane of incidence of the non-polarized UV-light. From tilt angle evaluation by means of the crystal rotation method a tilt angle value of 88.65° with respect to the substrate surface was obtained. The direction of the LC molecules was in between the surface normal and the direction of the incident light.

Figure 1 : Molecular structure of the LPP.

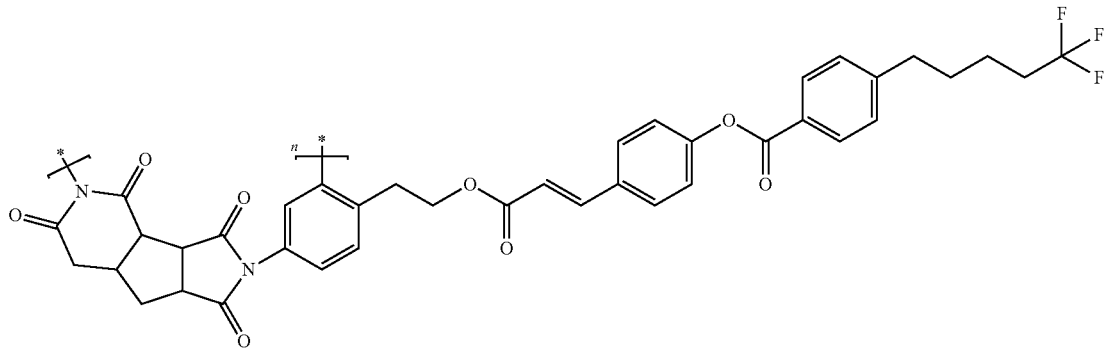

COMPARATIVE SYNTHESIS EXAMPLE 1

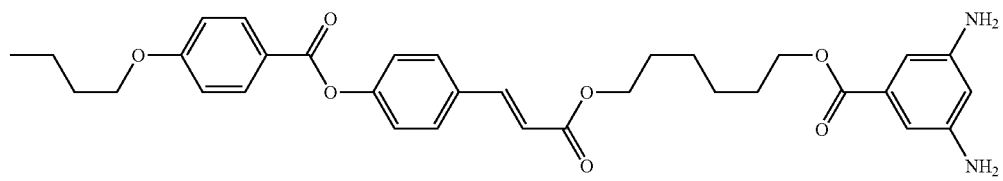

Analogous to example 2 1 6-{[((2E)-3-{4-[(4-butoxybenzoyl)oxy]phenyl}prop-2-enoyl)oxy]}hexyl 3,5-Diaminobenzoate were synthesized.

Comparative Polymerisation 1

The preparation is carried out analogously to Synthesis EXAMPLE 9 using 920.2 mg (1.683. mmol) 6-{[((2E)-3-{4-[(4-butoxybenzoyl)oxy]phenyl}prop-2-enoyl)oxy]}hexyl 3,5-Diaminobenzoate, 330.1 mg 1.683 mmol) 1,2,3,4-cyclobutantetracarboxylic acid dianhydride to yield 1.01 g Comparative Polyamic Acid 1; [η]=0.25 dL/g

COMPARATIVE SYNTHESIS EXAMPLE 2

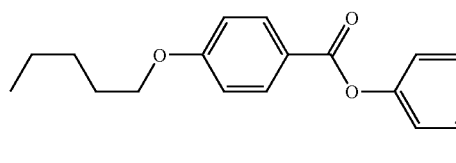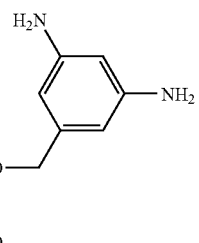

Analogous to example 3 3,5-Diaminobenzyl (2E)3-{4-[(4-pentyloxy)benzoyl]oxy}phenyl}acrylate are synthesized.

Comparative Polymerisation 2

The preparation is carried out analogously to Synthesis EXAMPLE 9 using 1.0390 g (2.15 mmol) 3,5-Diaminobenzyl (2E)3-{4-[(4-pentyloxy)benzoyl]oxy}phenyl}acrylate, 422.2 mg (2.15 mmol) 1,2,3,4-cyclobutantetracarboxylic acid dianhydride to yield 1.349 g Comparative Polyamic Acid 2; [η]=0.87 dL/g Example for the Production of an Orientation Layer Having a Defined Angle of Tilt 2% solution of Polyamic acid 1 in cyclopentanone is filtered over a 0.2 μm Teflon filter and applied to a glass plate, which has been coated with indium-tin oxide (ITO), in a spin-coating apparatus at 3000 rev./min. in the course of 60 seconds. The resulting film is then predried for 15 minutes at 130° C. and then imidized for 1 hour at 200° C. to form a polyimide film. The so obtained LPP film is irradiated for 30 mJ/cm2 with linearly polarised UV light, the direction of incidence of the light being inclined by 20° to 40° relative to the plate normal. The direction of polarisation of the light was kept in the plane defined by the direction of incidence of the light and the plate normal. From both plates a cell of 20 μm spacing is built such that the illuminated surfaces are facing each other and the previous polarisation directions of illumination are parallel. The cell is then filled with liquid crystal mixture MLC6609 from Merck in the isotropic phase at 100° C. The cell is then gradually cooled to room temperature at a rate ranging from 0.1° C./min to 2 C/min. Between crossed polarisers a uniformly oriented liquid crystal layer is observed. The tilt angle of this parallel cell, by crystal rotation method, was 88.7°.

Example for the Determination of the Voltage Holding Ratio (VHR)

Two glass plates coated in accordance with the above example are irradiated perpendicularly during 4 minutes with linearly polarised UV light. From both plates a cell of 10 μm spacing is built such that the illuminated surfaces were facing each other and the previous polarisation directions of illumination are parallel. This cell is then maintained at 120° C. under high vacuum for 14 hours and thereafter filled with TFT liquid crystal mixture MLC6610 from Merck in vacuum at room temperature. Between crossed polarisers a uniformly oriented liquid crystal layer is observed. Prior to testing the voltage holding ratio (VHR) the cell is first subjected to ageing for 50 hours at 120 C The voltage decay V (at T=20 ms) of a voltage surge of 64 μs with $V_0$ (V at t=0)=0.2 V is then measured over a period of T=20 ms. The voltage holding ratio then determined, given by VHR=$V_{rms}$(t=T)/$V_0$.

| Results | | |
|---|---|---|
| | VHR = $V_{rms}$(t = T)/$V_0$ at room temperature | VHR = $V_{rms}$(t = T)/$V_0$ at 80° C. |
| Polyamic acid 1 | 97% | 92% |
| Comparative Polyamic acid 1 | 85% | 62% |
| Polyamic acid 6 | 99% | 93% |
| Comparative Polyamic acid 2 | 99% | 71% |
| Blend between Polyamic acid 1 and Polyimide 1 (75:25 Weight ratio) | 95% | 92% |

The invention claimed is:

1. Diamine compound of formula (I):

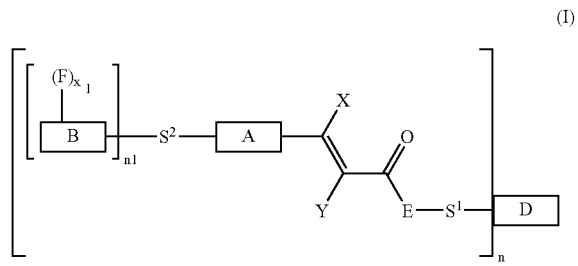

wherein,

A represents an unsubstituted or substituted carbocyclic or heterocyclic aromatic group selected from a monocyclic ring of five or six atoms, two adjacent monocyclic rings of five or six atoms, a bicyclic ring system of eight, nine or ten atoms, or a tricyclic ring system of thirteen or fourteen atoms;

and
wherein the following compound residue of formula (I), the compound of formula (Ia)

(Ia)

represents a straight-chain or branched $C_1$-$C_{16}$fluoroalkyl group, wherein
F is fluorine, and
$x_1$ is an integer from 1 to 15,
B represents a straight-chain or branched $C_1$-$C_{16}$alkyl group, which is in addition to its fluorine unsubstituted or substituent(s) substituted by di-($C_1$-$C_{16}$alkyl)amino, $C_1$-$C_6$alkyloxy, nitro, cyano and/or chlorine; and wherein one or more —$CH_2$— group may independently from each other be replaced by a linking group;
D represents an unsubstituted or substituted, aliphatic, aromatic and/or alicyclic diamine group having from 1 to 40 carbon atoms,
E represents an aromatic group, an oxygen atom, a sulphur atom, —NH—, —N($C_1$-$C_6$alkyl)-, —$CR^2R^3$,
wherein $R^2$ and $R^3$ are independently from each other hydrogen or a cyclic, straight-chain or branched, substituted or unsubstituted $C_1$-$C_{24}$alkyl, wherein one or more —$CH_2$— group(s) may be independently from each other replaced by a linking group, and with the proviso that at least one of $R^2$ and $R^3$ is not hydrogen;
$S^1$, $S^2$ each independently from each other represents a spacer unit;
X, Y each independently from each other represents hydrogen, fluorine, chlorine, cyano, unsubstituted or with fluorine substituted $C_1$-$C_{12}$alkyl, in which one or more —$CH_2$— groups may be replaced by a linking group;
n, n1 each independently from each other represents 1, 2, 3 or 4,
with the proviso that if n is 2, 3, or 4, each A, B, $x_1$, D, E, $S^1$, $S^2$, X, Y are identical or different;
and if n1 is 2, 3 or 4 each B, $X_1$ is identical or different.

2. Diamine compound according to claim 1, wherein the linking group is selected from —O—, —CO, —Co—O—, —O—CO—,

—$NR^1$—, —$NR^1$—CO—, —CO—$NR^1$—, —$NR^1$—CO—O—, —O—CO—$NR^1$—, —$NR^1$—CO—$NR^1$—, —CH=CH—, —C≡C—, —O—CO—O—, and —Si($CH_3$)$_2$—O—Si($CH_3$)$_2$—, and wherein:
$R^1$ represents a hydrogen atom or $C_1$-$C_6$alkyl;
with the proviso that oxygen atoms of linking groups are not directly linked to each other.

3. Diamine compound according to claim 1, wherein the spacer unit is a single bond, a cyclic, straight-chain or branched, substituted or unsubstituted $C_1$-$C_{24}$alkylene, wherein one or more —$CH_2$— group may independently from each other be replaced by a linking group selected from —O—, —CO, —CO—O—, —O—CO—,

—$NR^1$—, —$NR^1$—CO—, —CO—$NR^1$—, —$NR^1$—CO—O—, —O—CO—$NR^1$—, —$NR^1$—CO—$NR^1$—, —CH=CH—, —C≡C—, —O—CO—O—, and —Si($CH_3$)$_2$—O—Si($CH_2$)$_2$—, and wherein:
$R^1$ represents a hydrogen atom or $C_1$-$C_6$alkyl;
and/or a non-aromatic, aromatic, unsubstituted or substituted carbocyclic or heterocyclic group connected via bridging groups.

4. Diamine compound according to claim 3, wherein the bridging group is selected from —CH(OH)—, —CO—, —$CH_2$(CO)—, —SO—, —$CH_2$(SO)—, —$SO_2$—, —$CH_2$($SO_2$)—, —COO—, —OCO—, —$COCF_2$—, —$CF_2$CO, —S—CO—, —CO—S—, —SOO—, —OSO—, —SOS—, —O—CO—O, —$CH_2$—$CH_2$—, —$OCH_2$—, —$CH_2$O—, —CH=CH—, —CH≡C—, —CH=Ch—COO—, —OCO—CH=CH—, —CH=N—, —C($CH_3$)=N—, —N=N— or a single bond; or a cyclic, straight-chain or branched, substituted or unsubstituted $C_1$-$C_{24}$alkylene, wherein one or more —$CH_2$— group may independently from each other be replaced by a linking group selected from —O—, —CO, —CO—O—, —O—CO—,

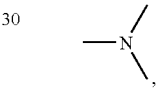

—$NR^1$—, —$NR^1$—CO—, —CO—$NR^1$—, —$NR^1$—CO—O—, —O—CO—$NR^1$—, —$NR^1$—CO—$NR^1$—, —CH=CH—, —C≡C—, —O—CO—O—, and —Si($CH_3$)$_2$—O—Si($CH_3$)$_2$—, and wherein:
$R^1$ represents a hydrogen atom or $C_1$-$C_6$alkyl.

5. Diamine compound according to claim 1, wherein D is selected from formula (III):

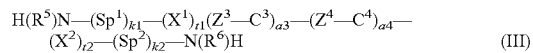

(III)

wherein:
$R^5$, $R^6$ each independently from each other represents a hydrogen atom or $C_1$-$C_6$alkyl;
$Sp^1$, $Sp^2$ each independently from each other represent an unsubstituted or substituted straight-chain or branched $C_1$-$C_{20}$alkylene, in which one or more —$CH_2$— group may independently from each other be replaced by a linking group, and
$k^1$, $k^2$ each independently is an integer having a value of 0 or 1; and
$X^1$, $X^2$ each independently represents a linking spacer, and
$t^1$, $t^2$ each independently is an integer having a value of 0 or 1; and
$C^3$, $C^4$ each independently represents a non-aromatic, aromatic, substituted or unsubstituted carbocyclic or heterocyclic group, which may have a side chain T, and
$Z^3$ represents a bridging group; and
$Z^4$ represents a substituted or unsubstituted straight-chain or branched $C_1$-$C_{20}$alkylene group, in which one or more —$CH_2$— group may independently from each other be replaced by a non-aromatic, aromatic, unsubstituted or substituted carbocyclic or heterocyclic group; and/or a heteroatom and/or by a bridging group; and $a_3$, $a_4$ are independently integers from 0 to 3, such that $a_3+a_4 \geq 4$; and wherein D is at least once linked to at least one group $S^1$ in formula (I) via group $Sp^1$ and/or group $Sp^2$; and/or linked via at least one non-aromatic, aromatic, substituted or unsubstituted carbocyclic or heterocyclic group of $C^3$ and/or group of $C^4$, and/or linked via at least one side chain T of group $C^4$ and/or group $C^3$; and/or linked via group $Z^4$; and at least one of $k^1$, $k^2$, $a^3$ and $a^4$ is not equal to zero; and wherein the linking group is selected from —O—, —CO, —CO—O—, —O—CO—,

—NR$^1$—, —NR$^1$—CO—, —CO—NR$^1$—, —NR$^1$—CO—O—, —O—CO—NR$^1$, —NR$^1$—CO—NR$^1$—, —CH=CH—, —C≡C—, —O—CO—O—, and —Si(CH$_3$)$_2$—O—Si(CH$_3$)$_2$—, and wherein:

$R^1$ represents a hydrogen atom or $C_1$-$C_6$alkyl, and the bridging group is selected from —CH(OH)—, —CO—, —CH$_2$(CO)—, —SO—, —CH$_2$(SO)—, —CH$_2$(SO$_2$)—, —COO—, —OCO—, —COCF$_2$—, —CF$_2$CO, —S—CO—, —CO—S—, —SOO—, —OSO—, —SOS—, —O—CO—O, —CH$_2$—CH$_2$—, —OCH$_2$—, —CH$_2$O—, —CH=CH—, —C≡C—, —CH=CH—COO—, —OCO—CH=CH—, —CH=N—, —C(CH$_3$)=N—, —N=N— or a single bond; or a cyclic, straight-chain or branched, substituted or unsubstituted $C_1$-$C_{24}$alkylene, wherein one or more —CH$_2$— group may independently from each other be replaced by a linking group selected from —O—, —CO, —CO—O—, —O—CO—,

—NR$^1$—, —NR$^1$—CO—, —CO—NR$^1$, —NR$^1$—CO—O—, —O—CO—NR$^1$—, —NR$^1$CO—NR$^1$, —CH=CH—, —C≡C—, —O—CO—O—, and —Si(CH$_3$)$_2$—O—Si(CH$_3$)$_2$—, and wherein:

$R^1$ represents a hydrogen atom or $C_1$-$C_6$alkyl.

6. Diamine compound according to claim 5, wherein the side chain, T, represents a substituted or unsubstituted straight-chain or branched $C_1$-$C_{20}$alkylene group, in which one or more —CH$_2$— group(s) may independently from each other be replaced by a non-aromatic, aromatic, unsubstituted or substituted carbocyclic or heterocyclic group, or a heteroatom and/or by a bridging group, which is at least once linked to at least one group $S^1$ in formula (I).

7. Diamine compound according to claim 5, wherein $C^3$, $C^4$ independently from each other are selected from a compound of group $G^2$, wherein $G^2$ is:

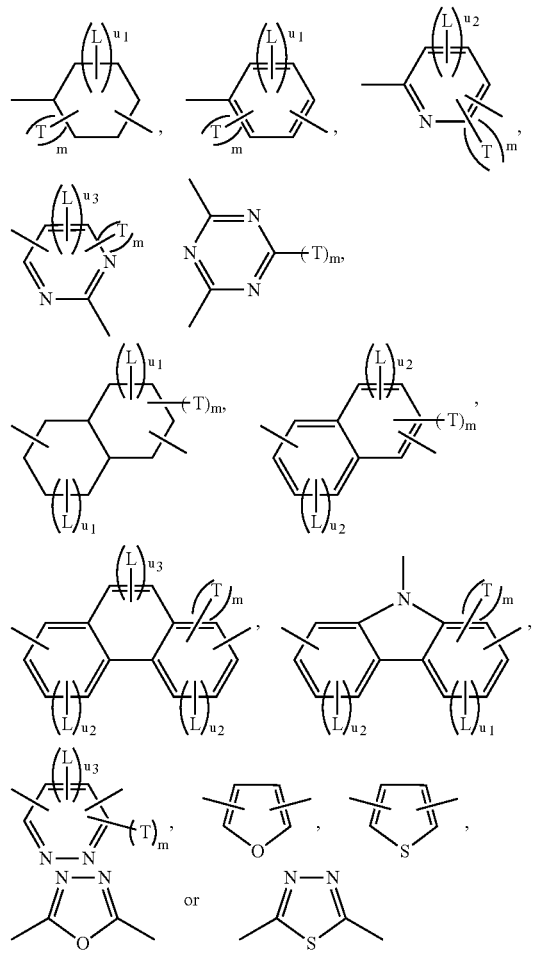

wherein:

"—" denotes the connecting bonds of $C^3$ and $C^4$ to the adjacent groups of compound of formula (III); and L is —CH$_3$, —COCH$_3$, —OCH$_3$, nitro, cyano, halogen, CH$_2$=CH—, CH$_2$=C(CH$_3$)—, CH$_2$=CH—(CO)O—, CH$_2$=CH—O—, —NR$^5$R$^6$, CH$_2$=C(CH$_3$)—(CO)O—, CH$_2$=C(CH$_3$)—O—, wherein:

$R^5$, $R^6$ each independently from each other represents a hydrogen atom or $C_1$-$C_6$alkyl;

T represents a substituted or unsubstituted straight-chain or branched $C_1$-$C_{20}$alkylene group, in which one or more —CH$_2$— group may independently from each other be replaced by a non-aromatic, aromatic, unsubstituted or substituted carbocyclic or heterocyclic group, or a heteroatom and/or by a bridging group;

m is an integer from 0 to 2;

$u_1$ is an integer from 0 to 4, with the proviso that m+$u_1$ is $\leq 4$; and $u_2$ is an integer from 0 to 3; with the proviso that m+$u_2$ is $\leq 3$; and $u_3$ is an integer from 0 to 2; with the proviso that m+$u_3$ is $\leq 2$.

8. Diamine compound according to claim 1, wherein D is selected from the following compounds:

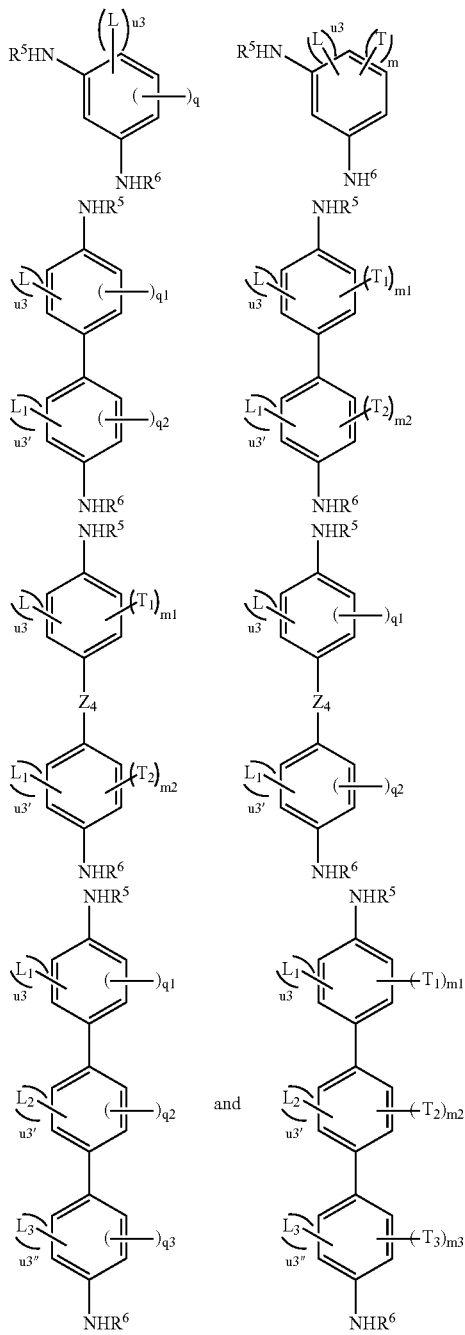

wherein

L, L₁, L₂ and L₃ are independently from each other —CH₃, —COCH₃, —OCH₃, nitro, cyano, halogen, CH₂=CH—, CH₂=C(CH₃)—, CH₂=CH—(CO)O—, CH₂=CH—O—, —NR⁵R⁶, CH₂=C(CH₃)—(CO)O— or CH₂=C(CH₃)—O—, T, T₁, T₂ and T₃ are independently from each other a substituted or unsubstituted straight-chain or branched $C_1$-$C_{20}$alkylene group, in which one or more —CH₂— group(s) may independently from each other be replaced by a non-aromatic, aromatic, unsubstituted or substituted carbocyclic or heterocyclic group, and/or a heteroatom and/or by a bridging group;

"—" is a single bond, q is an integer of 1 or 2; and q1, q2 and q3 are independently from each other an integer from 0 to 2;

m is an integer of 1 or 2;

m1, m2 and m3 are independently from each other an integer from 0 to 2;

u3, u3' and u3" are independently from each other an integer from 0 to 2;

$R^5$, $R^6$ each independently from each other represents a hydrogen atom or $C_1$-$C_6$alkyl and $Z^4$ represents a substituted or unsubstituted straight-chain or branched $C_1$-$C_6$alkylene group, in which one or more —CH₂— group may independently from each other be replaced by a non-aromatic, aromatic, unsubstituted or substituted carbocyclic or heterocyclic group; and/or a heteroatom and/or by a bridging group; and wherein D is at least once linked to at least one group $S^1$ in formula (I) via a single bond "—"; or via a side chain T, $T_1$, $T_2$ or $T_3$; or via group $Z^4$;

with the proviso that u3+q, or u3+m is $\leq 4$;

u3+q1 and/or u3'+q2 or/and u3+m1, or/and u3'+m2, or/and u3"+q3, or/and u3"+m3 is $\leq 4$;

q1+q2, and m1+m2; and q1+q2+q3, and m1+m2+m3 is $\geq 1$.

9. Diamine compound according to claim 1, wherein the following compound residue of a compound of formula (I)

represents a straight-chain or branched $C_1$-$C_{16}$fluoroalkyl group with terminal units selected from —CF₂H and —CF₃.

10. Diamine compound according to any claim 1, wherein $S^1$, $S^2$ each independently from each other represents a single bond or a cyclic, straight-chain or branched, substituted or unsubstituted $C_1$-$C_{24}$alkylene, in which one or more —CH₂— group may independently from each other be replaced by a linking group, and/or a non-aromatic, aromatic, unsubstituted or substituted carbocyclic or heterocyclic group of formula (IV):

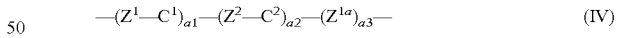

wherein:

$C^1$, $C^2$ each independently represents a non-aromatic, aromatic, unsubstituted or substituted carbocyclic or heterocyclic group, and $Z^1$, $Z^2$, $Z^{1a}$ each independently represents a bridging group, and $a_1$, $a_2$, $a_3$ each independently represents an integer from 0 to 3, $a_1+a_2+a_3 \leq 6$, wherein the bridging groups $Z^1$, $Z^{1a}$ and $Z^2$ are selected from —CH(OH)—, —CO—, —CH₂(CO)—, —SO—, —CH₂(SO)—, —SO₂—, —CH₂(SO₂)—, —COO—, —OCO—, —COCF₂—, —CF₂CO—, —S—CO—, —CO—S—, —SOO—, —OSO—, —SOS—, —O—CO—O, —CH₂—CH₂—, —OCH₂—, —CH₂O—, —CH=CH—, —C≡C—, —CH=CH—COO—, —OCO—CH=CH—, —CH=N—, —C(CH₃)=N—, —N=N— or a single bond; or a cyclic, straight-chain or branched, substituted or unsubstituted $C_1$-$C_{24}$alkylene, wherein one or more —$CH_2$— group may independently from each other be replaced by a linking group selected from —O—, —CO—, —CO—O—, —O—CO—,

—$NR^1$, —$NR^1$—CO—, —CO—$NR^1$—, —$NR^1$—CO—O—, —O—CO—$NR^1$—, —$NR^1$—CO—$NR^1$—, —CH=CH—, —C≡C—, —O—CO—O—, and —Si($CH_3$)$_2$—O—Si($CH_3$)$_2$—, and wherein:

$R^1$ represents a hydrogen atom or $C_1$-$C_6$alkyl.

11. Diamine compound according to claim 1, which is a compound of formulae (VI), (VII), (VIII), (IX), (X), (XI), (XIa) and (XIb)

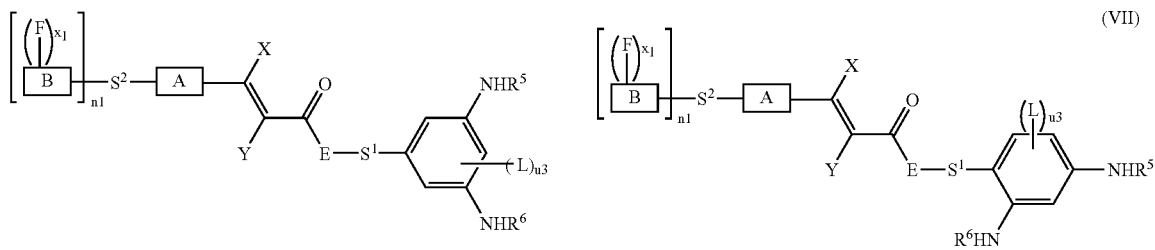

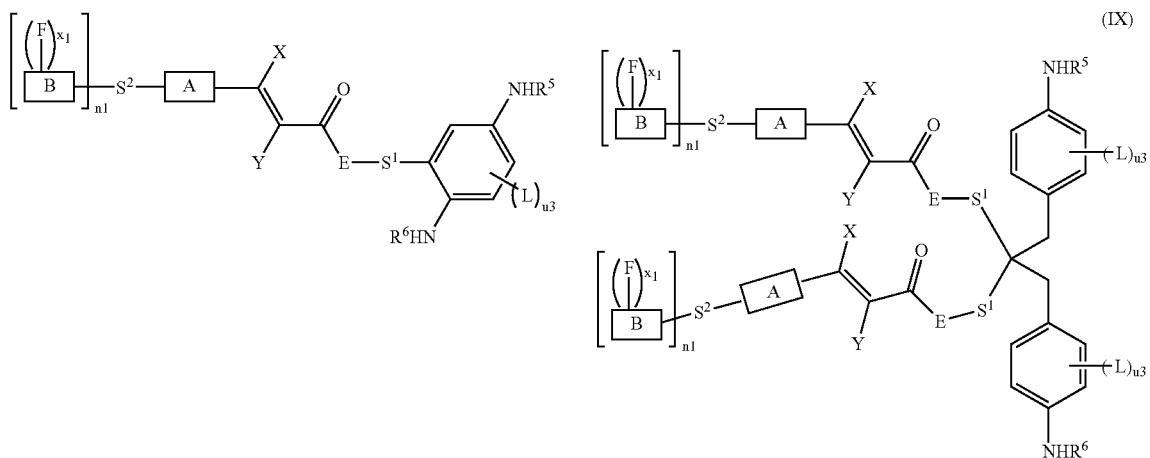

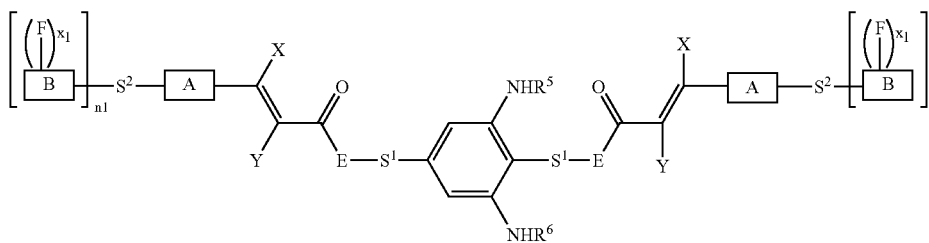

(XI)

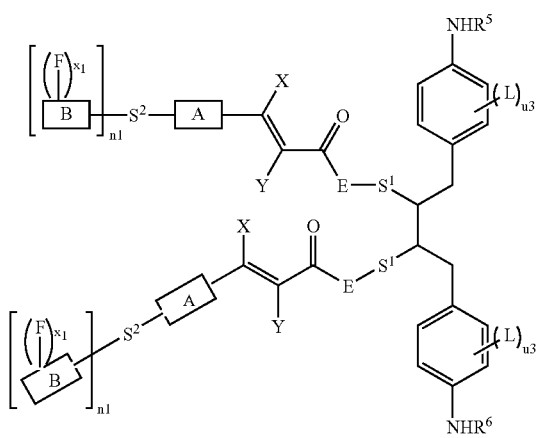

(XIa)

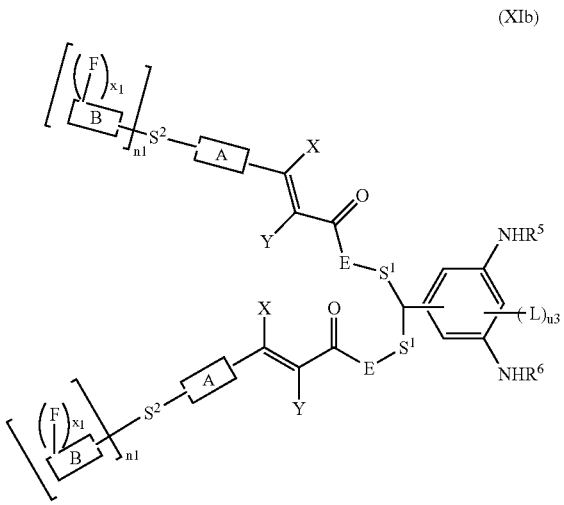

(XIb)

wherein

A, B, $x_1$, n, n1, D, E, $S^2$, $S^1$, X and Y have the above given meanings as in claim 1 and $R^5$, $R^6$ each independently from each other represents a hydrogen atom or $C_1$-$C_6$alkyl and $Z^4$ represents a substituted or unsubstituted straight-chain or branched $C_1$-$C_{20}$alkylene group, in which one or more —$CH_2$— group may independently from each other be replaced by a non-aromatic, aromatic, unsubstituted or substituted carbocyclic or heterocyclic group; and/or a heteroatom and/or by a bridging group;

L is —$CH_3$, —$OCH_3$, —$COCH_3$, nitro, cyano, halogen, $CH_2$=CH—, $CH_2$=C($CH_3$)—, $CH_2$=CH—(CO)O—, $CH_2$=CH—O—, $CH_2$=C($CH_3$)—(CO)O—, or $CH_2$=C($CH_3$)—O—, $u_3$ is an integer from 0 to 2.

12. Diamine compound according to claim 1, which is a compound of formula (XII)

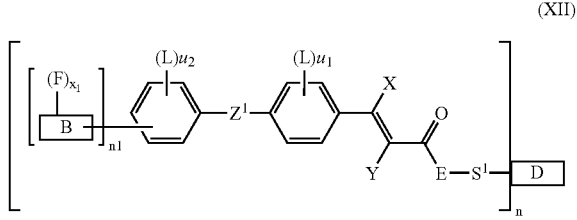

(XII)

wherein $x_1$, B, n, n1, D, E, $S^1$, X and Y have the above given meanings as in claim 1, $Z^1$ represents a bridging group, L is —$CH_3$, —$COCH_3$, —$OCH_3$, nitro, cyano, halogen, $CH_2$=CH—, $CH_2$=C($CH_3$), $CH_2$=CH—(CO)O—, $CH_2$=CH—O—, —$NR^5R^6$, $CH_2$=C($CH_3$)—(CO)O—, $CH_2$=C($CH_3$)—O—, wherein:

$R^5$, $R^6$ each independently from each other represents a hydrogen atom or $C_1$-$C_6$alkyl, and $u_1$ is an integer of 0 to 4 and $u_2$ is an integer of 0 to 3.

13. Diamine compound according to claim 1, selected from

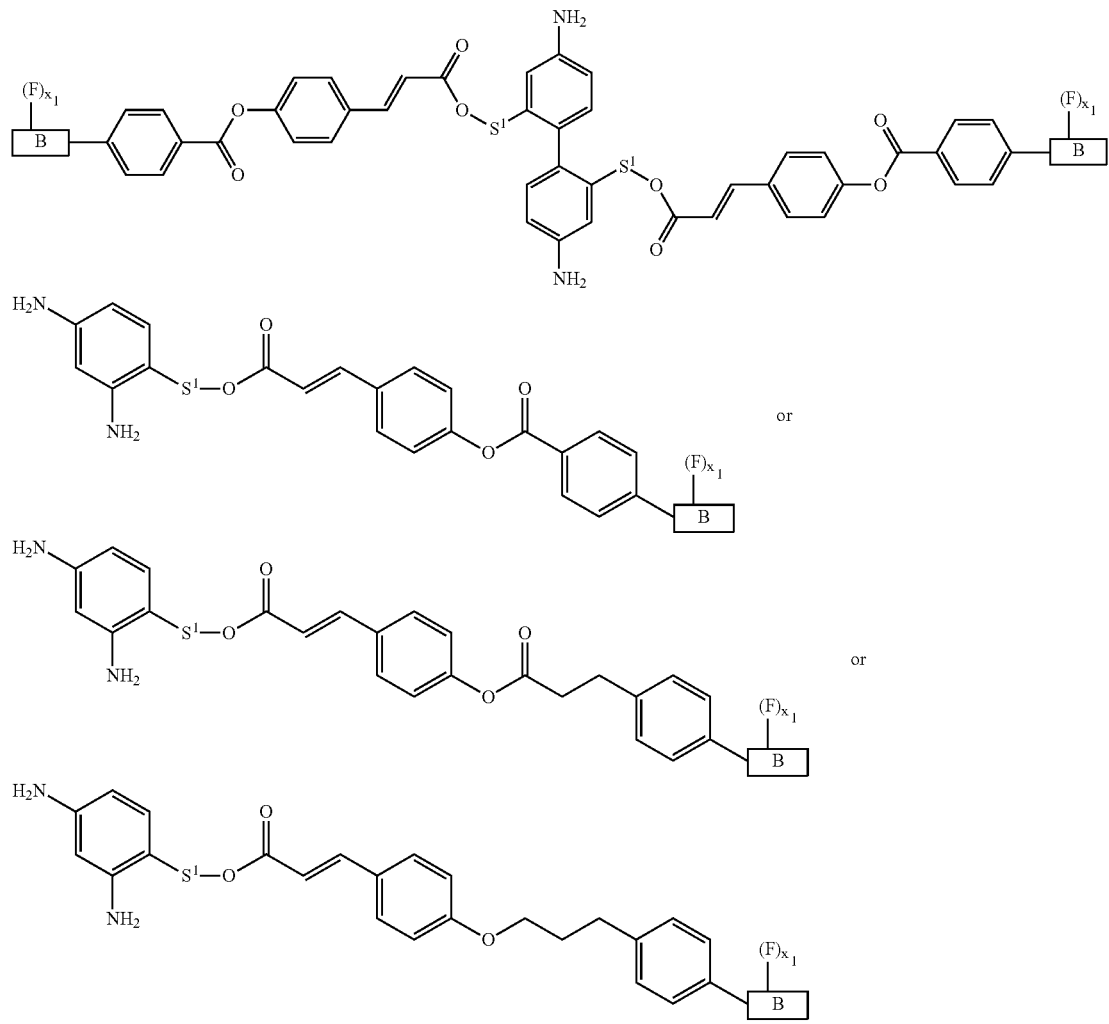

wherein $S^1$ has the above given meaning as in claim 1 and wherein the following compound residue

[structure shown]

represents a straight-chain or branched $C_1$-$C_8$fluoroalkyl group, wherein

F is fluorine, and $X_1$ is an integer from 1 to 9,

B represents a straight-chain or branched $C_1$-$C_8$alkyl group, which is unsubstituted or in addition to its fluorine substituent(s) substituted by di-($C_1$-$C_{16}$alkyl)amino, $C_1$-$C_6$alkyloxy, nitro, cyano and/or chlorine; and wherein one or more —$CH_2$— group may independently be replaced by a linking group selected from —O—, —CO—, —CO—O—, —O—CO—, —$NR^1$, —$NR^1$—CO—, —CO—$NR^1$— and —CH=CH—, wherein:

$R^1$ represents a hydrogen atom or $C_1$-$C_6$alkyl;

with the proviso that oxygen atoms are not directly linked to each other;

and wherein the $C_1$-$C_8$-fluoroalkyl group has terminal units selected from —$CF_2H$ and —$CF_3$.

14. A process for the preparation of diamine compound (XII) as defined in claim 12 comprising contacting a compound of formula (XIV)

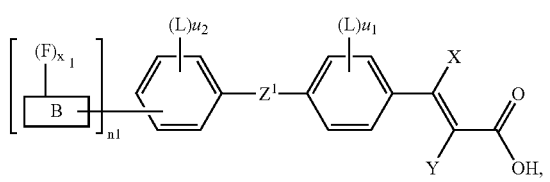

(XIV)

121 with a dinitro compound of formula (XVI)

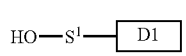
(XVI)

and then converting the obtained dinitro compound of formula (XVIa)

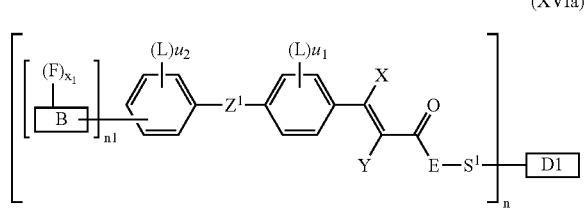
(XVIa)

122 to the corresponding diamino compound of formula (XII)

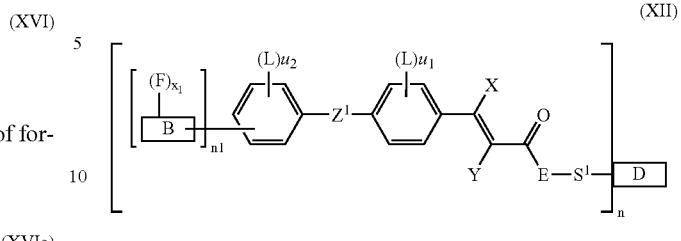
(XII)

wherein $F, X_1, n_1, n, B, D, E, X, Y, Z^1, L, u_1, u_2$ and $S^1$ have the same meaning as in claim 12, and wherein D1 has the same meaning as D as in claim 12, with the proviso that the two amino groups of D are replaced by two nitro groups.

15. Composition comprising at least one diamine compound of formula (I) according to claim 1 and optionally at least one further diamine, which is different from the diamine compound of formula (I), or/and an additive.

* * * * *